(12) United States Patent
Picataggio et al.

(10) Patent No.: US 9,133,465 B2
(45) Date of Patent: *Sep. 15, 2015

(54) PRODUCTION OF POLYUNSATURATED FATTY ACIDS IN OLEAGINOUS YEASTS

(71) Applicant: E I DU PONT DE NEMOURS AND COMPANY, Wilmington, DE (US)

(72) Inventors: Stephen K Picataggio, Solana Beach, CA (US); Narendra S Yadav, Wilmington, DE (US); Quinn Qun Zhu, West Chester, PA (US)

(73) Assignee: E. I. DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/677,911

(22) Filed: Nov. 15, 2012

(65) Prior Publication Data

US 2013/0143305 A1 Jun. 6, 2013

Related U.S. Application Data

(60) Continuation of application No. 12/469,467, filed on May 20, 2009, now Pat. No. 8,399,242, which is a division of application No. 11/714,377, filed on Mar. 5, 2007, now Pat. No. 7,553,628, which is a division of application No. 10/840,579, filed on May 6, 2004, now Pat. No. 7,238,482.

(60) Provisional application No. 60/468,677, filed on May 7, 2003.

(51) Int. Cl.
*C12N 1/19* (2006.01)
*C12N 15/81* (2006.01)
*C12P 7/64* (2006.01)

(52) U.S. Cl.
CPC ............ *C12N 15/815* (2013.01); *C12P 7/6427* (2013.01); *C12P 7/6472* (2013.01)

(58) Field of Classification Search
CPC .................................... C12N 1/00; C12N 1/16
USPC ............................................. 435/254.2, 255.1
See application file for complete search history.

(56) References Cited

U.S. PATENT DOCUMENTS

| | | |
|---|---|---|
| 4,758,592 A | 7/1988 | Horrobin et al. |
| 4,826,877 A | 5/1989 | Stewart et al. |
| 4,880,741 A | 11/1989 | Davidow et al. |
| 5,057,419 A | 10/1991 | Martin et al. |
| 5,071,764 A | 12/1991 | Davidow et al. |
| 5,116,871 A | 5/1992 | Horrobin et al. |
| 5,244,921 A | 9/1993 | Kyle et al. |
| 5,407,957 A | 4/1995 | Kyle et al. |
| 5,443,974 A | 8/1995 | Hitz et al. |
| 5,492,938 A | 2/1996 | Kyle et al. |
| 5,658,767 A | 8/1997 | Kyle |
| 5,968,809 A | 10/1999 | Knutzon et al. |
| 5,972,664 A | 10/1999 | Knutzon et al. |
| 6,075,183 A | 6/2000 | Knutzon et al. |
| 6,136,574 A | 10/2000 | Knutzon et al. |
| 6,677,145 B2 | 1/2004 | Mukerji et al. |
| 2003/0196217 A1 | 10/2003 | Mukerji et al. |

FOREIGN PATENT DOCUMENTS

| | | |
|---|---|---|
| EP | 0005277 B1 | 1/1982 |
| WO | 199113972 A1 | 9/1991 |
| WO | 9311245 | 6/1993 |
| WO | 9411516 A1 | 5/1994 |
| WO | 0012720 A2 | 3/2000 |
| WO | 02090493 A2 | 11/2002 |
| WO | 03099216 A2 | 12/2003 |

OTHER PUBLICATIONS

Triboli et al. Influence of the temperature on batch cultivation. Biotech. Letters 16(4): 385-388, 1994.*
Dyerberg, J. et al., Fatty Acid Composition of the plasma lipids in Greenland Eskimos, Amer. J. Clin Nutr. 28: pp. 958-966, 1975.
Dyerberg, J. et al., Eicosapentaenoic Acid and Prevention of Thrombosis and Atherosclerosis?, Lancet 2(8081): pp. 117-119, Jul. 15, 1978.
Shimokawa, H., Beneficial Effects of Eicosapentaenoic Acid on Endothelial Vasodilator Functions in Animals and Humans, World Rev. Nutr. Diet, 88: pp. 100-108, 2001.
Von Schacky et al.,Fatty Acids from Eskimos to Clical Cardiology—What Took Us So Long?, World Rev. Nutr. Diet, 88: pp. 90-99, 2001.
Domergue et al., Cloning and functional characterization of Phaeodactylum tricornutuim front-end desaturases involved in eicosapentaenoic acid biosynthesis, Eur. J. Biochem. 269: 4105-4113, 2002.
Beaudoin et al., Heterologous reconstitution in yeast of the polyunsaturated fatty acid biosynthetic pathway, Proc. Natl. Acad. Sci. U.S.A. 97(12): 6421-6, 2000.
Dyer et al.,Metabolic engineering of Saccharomyces cerevisiae for production of novel lipid compounds, Appl. Eniv. Microbiol., 59: pp. 224-230, 2002.
Ratledge, Microbial Oils and Fats: An Assessment of their Commercial Potential, C., Prog. Ind. Microbiol. 16: 119-206, 1982.
Brenner et al., Regulatory function of Delta6 Desaturase—Key Enzyme of Polyunsaturated Fatty Acid Synthesis, Adv. Exp. Med. Biol. 83: pp. 85-101, 1976.
Horrobin et al., Fatty acid metabolism in health and sisease: the role of delta-6-desaturase Am. J. Clin. Nutr. 57, (Suppl.) 732S-737S,1993.
Kris-Etherton, P.M. et al., Polyunsaturated fatty acids in the food chain in the United States, Am. J. Clin. Nutr. 71(1 Suppl.): 179S-88S, 2000.

(Continued)

*Primary Examiner* — Michele K Joike

(57) ABSTRACT

The present invention relates to methods for the production of ω-3 and/or ω-6 fatty acids in oleaginous yeast. Thus, desaturases and elongases able to catalyze the conversion of linoleic acid (LA) to γ-linolenic acid (GLA); α-linoleic acid (ALA) to stearidonic acid (STA); GLA to dihomo-γ-linoleic acid (DGLA); STA to eicosatetraenoic acid (ETA); DGLA to arachidonic acid (ARA); ETA to eicosapentaenoic acid (EPA); DGLA to ETA; EPA to docosapentaenoic acid (DPA); and ARA to EPA have been introduced into the genome of *Yarrowia* for synthesis of ARA and EPA.

13 Claims, 28 Drawing Sheets

(56) References Cited

OTHER PUBLICATIONS

Simopoulos, A. P. et al., Essentiality of an Recommended Dietary Intakes for Omega-6 and Omega-3 Fatty Acids, Ann. Nutr. Metab. 43: pp. 127-130, 1999.

Krauss, R.M. et al., Revision 2000: A Statement for Healthcare Professionals From the Nutrition Committee of the American Heart Association, AHA Circulation 102: 2284-2299, 2000.

Chen et al., One-step transformation of the dimorphic yeast Yarrowia lipolytica, Appl. Microbiol. Biotechnol. 48(2), pp. 232-235, 1997.

Passorn, Supapon et al., Heterologous Expression of Mucor rouxii Delta 12-Desaturase Gene in Saccharomyces cerevisiae, Biochemical and Biophysical Research Communications, 1999, pp. 47-51, vol. 263, Academic Press.

Sakuradani et al., Eur. J. Biochem, 261, 812-820 (1999).

Meesapyodsuk et al. Biochemical Society Transactions (2000) vol. 28, Part 6.

Supplemental EP Search Report, dated Oct. 17, 2008 for corresponding EP Patent Appln. 04751769.3.

\* cited by examiner

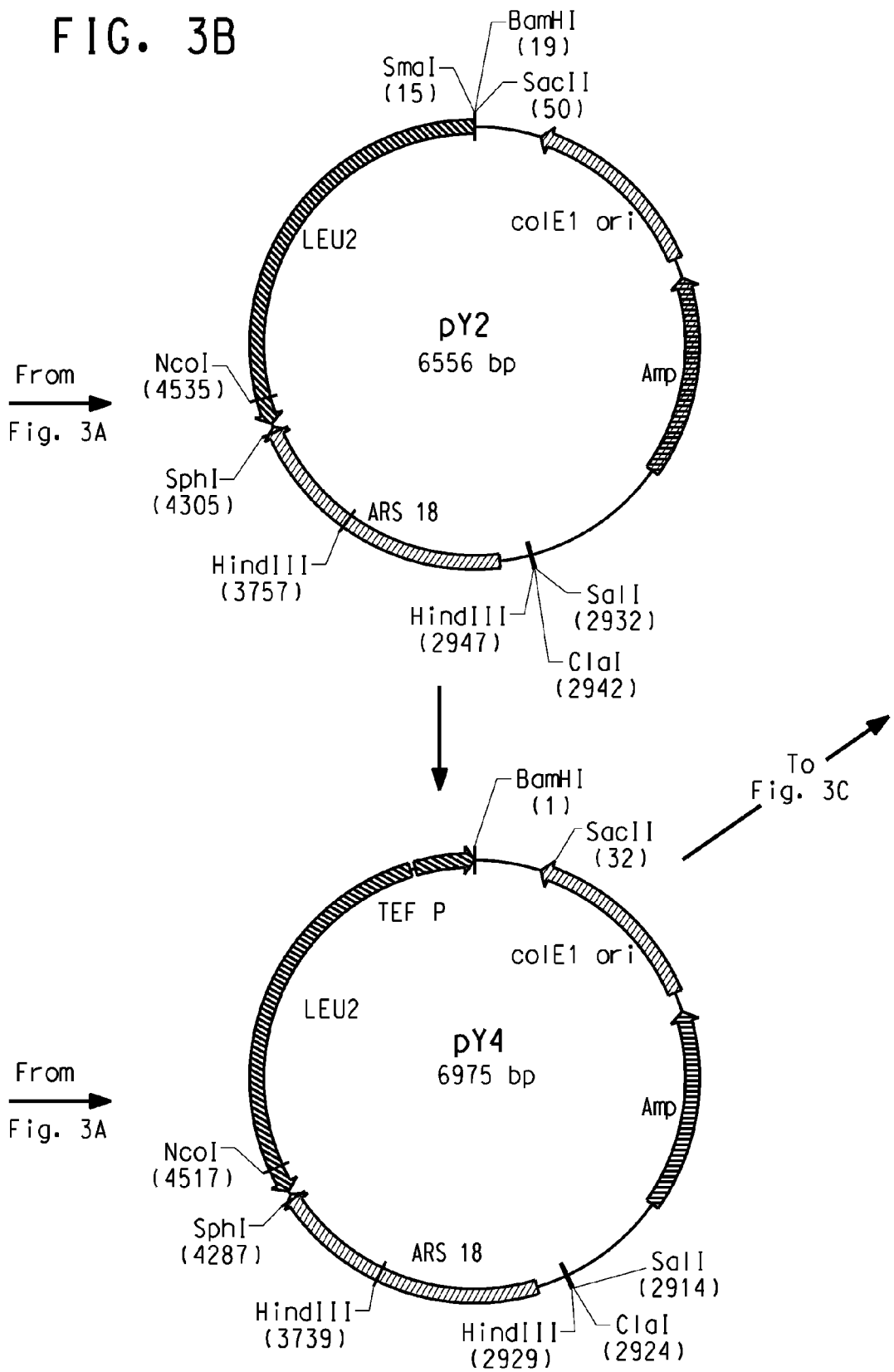

FIG. 6A

```
                                                  T T
CTCACATACTCGCTCCGCTCTTGCCGTCATGGGCCTTCTACTACTATGCCCGTCTTTGTCTTTGCTTCGT    700
 L  T  Y  S  L  G  F  A  V  M  G  L  Y  Y  Y  A  P  L  F  V  F  A  S
                    T           T     T T C     T
TCCTCGTCATTACGACCTTCTTGCACCACAACGACGAAGCGACGCCTGGTACGGCGACTCCGAGTGGAC    770
 F  L  V  I  T  T  F  L  H  H  N  D  E  A  T  P  W  Y  G  D  S  E  W  T
 C           GAGCTC       A       A  T           TCT
GTACGTCAAGGGCAACCTCTCGAGCGTCGACCGCTCGTACGGCGCGTTCGTGTGGACAACCTGAGCCACCAC    840
 Y  V  K  G  N  L  S  S  V  D  R  S  Y  G  A  P  V  D  N  L  S  H  H
         C     T        T       C
ATTGGCACGCACCAGGTTCCACCACTTGTTCCCGATCATTCCGCACTACAAGCTCAACGAAGCCACCAAGC    910
 I  G  T  H  Q  V  H  L  F  P  I  I  P  H  Y  K  L  N  E  A  T  K
            T  T T                     A  AC T
ACTTTGCGGCCGCTACCCGCACCTGTGCCGCAGGAACGACGAGCCATCATCACGGCCTTCTTCAAGAC    980
 H  F  A  A  A  Y  P  H  L  V  R  R  N  D  E  P  I  I  T  A  F  F  K  T
            A           T         T    C           T  T
CGGCGCACCTTCTTGTCAACTACGGCGCCGTGCCCGAGACGGCGCAGATCTTCACGCTCAAAGAGTCGGCC    1050
 A  H  L  F  V  N  Y  G  A  V  P  E  T  A  Q  I  F  T  L  K  E  S  A
 T  A                    AGC
GCGGCCGCCAAGGCCAAGTCGGACTAA    1077
 A  A  K  A  K  S  D
```

FIG. 6B cAAAATGNCtG [SEQ ID NO:126]
A CC       TC
           A

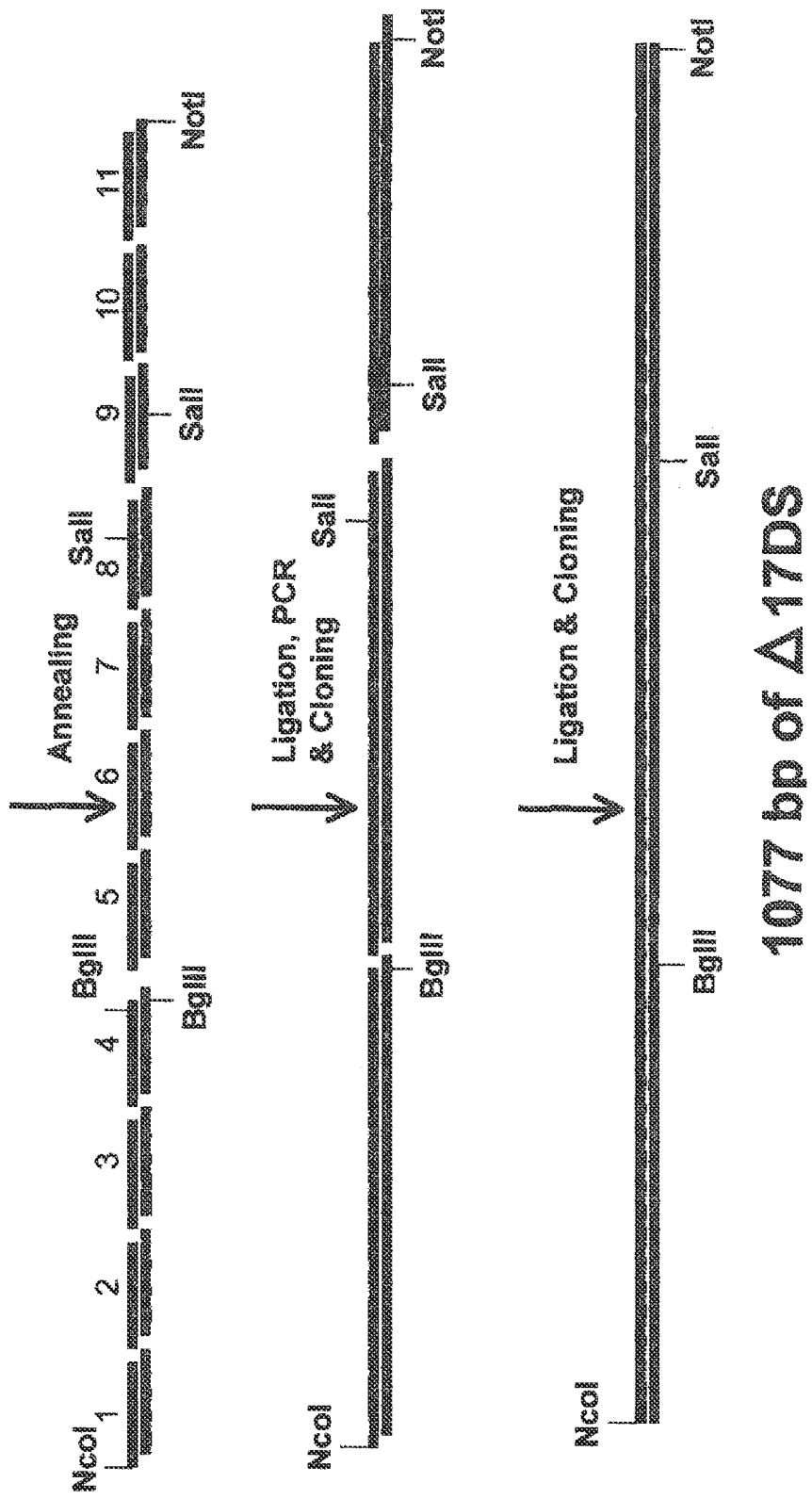
F I G. 8

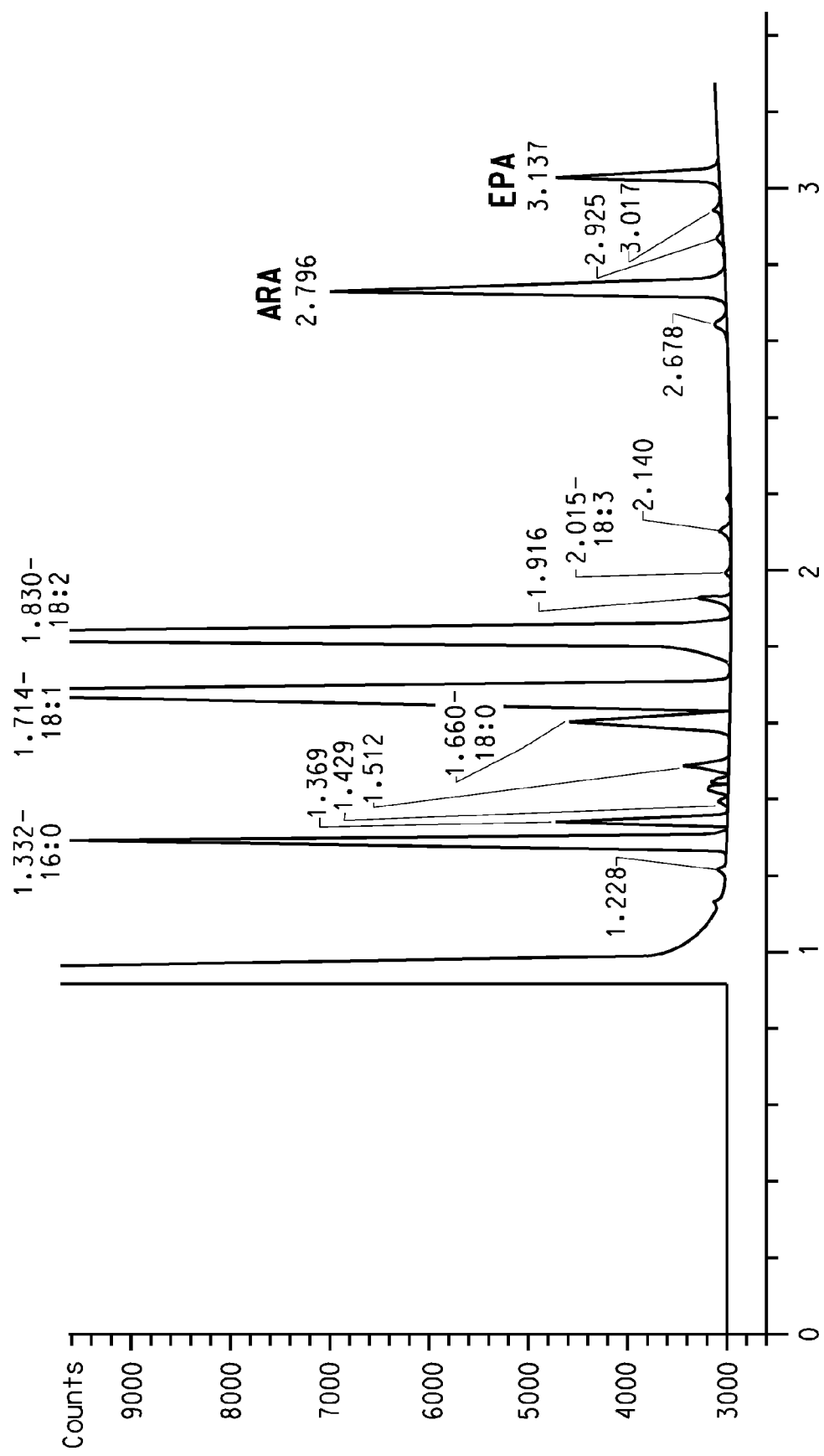

PRODUCTION OF POLYUNSATURATED FATTY ACIDS IN OLEAGINOUS YEASTS

This application is a continuation of pending application Ser. No. 12/469,467, filed May 20, 2009, which is a divisional application of application Ser. No. 11/714,377, filed Mar. 5, 2007 (now U.S. Pat. No. 7,553,628), which is a divisional application of application Ser. No. 10/840,579, filed May 6, 2004 (now U.S. Pat. No. 7,238,482), which claims the benefit of U.S. Provisional Application No. 60/468,677, filed May 7, 2003. The disclosures of all these prior applications are herein incorporated by reference in their entirety.

FIELD OF THE INVENTION

This invention is in the field of biotechnology. More specifically, this invention pertains to the production of long chain polyunsaturated fatty acids (PUFAs) in oleaginous yeasts.

BACKGROUND OF THE INVENTION

It has long been recognized that certain polyunsaturated fatty acids, or PUFAs, are important biological components of healthy cells. For example, such PUFAs are recognized as:
  "Essential" fatty acids that can not be synthesized de novo in mammals and instead must be obtained either in the diet or derived by further desaturation and elongation of linoleic acid (LA) or α-linolenic acid (ALA);
  Constituents of plasma membranes of cells, where they may be found in such forms as phospholipids or triglycerides;
  Necessary for proper development, particularly in the developing infant brain, and for tissue formation and repair; and,
  Precursors to several biologically active eicosanoids of importance in mammals, including prostacyclins, eicosanoids, leukotrienes and prostaglandins.

In the 1970's, observations of Greenland Eskimos linked a low incidence of heart disease and a high intake of long-chain ω-3 PUFAs (Dyerberg, J. et al., *Amer. J. Clin Nutr.* 28:958-966 (1975); Dyerberg, J. et al., *Lancet* 2(8081):117-119 (Jul. 15, 1978)). More recent studies have confirmed the cardiovascular protective effects of ω-3 PUFAs (Shimokawa, H., *World Rev Nutr Diet,* 88:100-108 (2001); von Schacky, C., and Dyerberg, J., *World Rev Nutr Diet,* 88:90-99 (2001)). Further, it has been discovered that several disorders respond to treatment with ω-3 fatty acids, such as the rate of restenosis after angioplasty, symptoms of inflammation and rheumatoid arthritis, asthma, psoriasis and eczema. γ-linolenic acid (GLA, an ω-6 PUFA) has been shown to reduce increases in blood pressure associated with stress and to improve performance on arithmetic tests. GLA and dihomo-γ-linolenic acid (DGLA, another ω-6 PUFA) have been shown to inhibit platelet aggregation, cause vasodilation, lower cholesterol levels and inhibit proliferation of vessel wall smooth muscle and fibrous tissue (Brenner et al., *Adv. Exp. Med. Biol.* 83:85-101 (1976)). Administration of GLA or DGLA, alone or in combination with eicosapentaenoic acid (EPA, an ω-3 PUFA), has been shown to reduce or prevent gastrointestinal bleeding and other side effects caused by non-steroidal anti-inflammatory drugs (U.S. Pat. No. 4,666,701). Further, GLA and DGLA have been shown to prevent or treat endometriosis and premenstrual syndrome (U.S. Pat. No. 4,758,592) and to treat myalgic encephalomyelitis and chronic fatigue after viral infections (U.S. Pat. No. 5,116,871). Other evidence indicates that PUFAs may be involved in the regulation of calcium metabolism, suggesting that they may be useful in the treatment or prevention of osteoporosis and kidney or urinary tract stones. Finally, PUFAs can be used in the treatment of cancer and diabetes (U.S. Pat. No. 4,826,877; Horrobin et al., *Am. J. Clin. Nutr.* 57 (Suppl.): 732S-737S (1993)).

PUFAs are generally divided into two major classes (consisting of the ω-6 and the ω-3 fatty acids) that are derived by desaturation and elongation of the essential fatty acids, linoleic acid (LA) and α-linolenic acid (ALA), respectively. Despite this common derivation from "essential" fatty acids, it is becoming increasingly apparent that the ratio of ω-6 to ω-3 fatty acids in the diet is important for maintenance of good health. Due to changes in human dietary habits, the current ratio of ω-6 to ω-3 fatty acids is approximately 10:1, whereas the preferred ratio is 2:1 (Kris-Etherton, P. M. et al., *Am. J. Clin. Nutr.* 71 (1 Suppl.):179S-88S (2000); Simopoulos, A. P. et al., *Ann. Nutr. Metab.* 43:127-130 (1999); Krauss, R. M. et al. *AHA Circulation* 102:2284-2299 (2000)).

The main sources of ω-6 fatty acids are vegetable oils (e.g., corn oil, soy oil) that contain high amounts of LA. GLA is found in the seeds of a number of plants, including evening primrose (*Oenothera biennis*), borage (*Borago officinalis*) and black currants (*Ribes nigrum*). Microorganisms in the genera *Mortierella* (filamentous fungus), *Entomophthora, Pythium* and *Porphyridium* (red alga) can be used for commercial production of the ω-6 fatty acid, arachidonic acid (ARA). The fungus *Mortierella alpina*, for example, is used to produce an oil containing ARA, while U.S. Pat. No. 5,658,767 (Martek Corporation) teaches a method for the production of an oil containing ARA comprising cultivating *Pythium insidiuosum* in a culture medium containing a carbon and nitrogen source.

The ω-3 PUFAs of importance include EPA and docosahexaenoic acid (DHA), both of which are found in different types of fish oil and marine plankton. U.S. Pat. No. 5,244,921 (Martek Corporation) describes a process for producing an edible oil containing EPA by cultivating heterotrophic diatoms in a fermentor, specifically *Cyclotella* sp. and *Nitzschia* sp. DHA can be obtained from cold water marine fish, egg yolk fractions and by cultivation of certain heterotrophic microalgae of the class Dinophyceae, specifically, *Crypthecodinium* sp. such as *C. cohnii* (U.S. Pat. No. 5,492,938 and U.S. Pat. No. 5,407,957). Stearidonic acid (STA), a precursor to EPA and DHA, can be found in marine oils and plant seeds; its commercial sources include production in the genera *Trichodesma* and *Echium*. Other sources of ω-3 acids are found in flaxseed oil and walnut oil, each containing predominantly ALA.

Despite a variety of commercial sources of PUFAs from natural sources, there are several disadvantages associated with these methods of production. First, natural sources such as fish and plants tend to have highly heterogeneous oil compositions. The oils obtained from these sources therefore can require extensive purification to separate or enrich one or more of the desired PUFAs. Fish oils commonly have unpleasant tastes and odors, which may be impossible to separate economically from the desired product and can render such products unacceptable as food supplements. Unpleasant tastes and odors can make medical regimens based on ingestion of high dosages undesirable, and may inhibit compliance by the patient. Furthermore, fish may accumulate environmental pollutants and ingestion of fish oil capsules as a dietary supplement may result in ingestion of undesired contaminants. Natural sources are also subject to uncontrollable fluctuations in availability (e.g., due to weather, disease, or over-fishing in the case of fish stocks); and, crops that produce PUFAs often are not competitive economically with hybrid crops developed for food production. Large-scale fermentation of some organisms that naturally produce PUFAs (e.g., *Porphyridium, Mortierella*) can also be expensive and/or difficult to cultivate on a commercial scale.

As a result of the limitations described above, extensive work has been conducted toward: 1.) the development of recombinant sources of PUFAs that are easy to produce commercially; and 2.) modification of fatty acid biosynthetic pathways, to enable production of desired PUFAs.

Advances in the isolation, cloning and manipulation of fatty acid desaturase and elongase genes from various organisms have been made over the last several years. Knowledge of these gene sequences offers the prospect of producing a desired fatty acid and/or fatty acid composition in novel host organisms that do not naturally produce PUFAs. The literature reports a number of examples in *Saccharomyces cerevisiae*, such as:

1. Domergue, F. et al. (*Eur. J. Biochem.* 269:4105-4113 (2002)), wherein two desaturases from the marine diatom *Phaeodactylum tricornutum* were cloned into *S. cerevisiae*, leading to the production of EPA;
2. Beaudoin F., et al. (*Proc. Natl. Acad. Sci. U.S.A.* 97(12): 6421-6 (2000)), wherein the ω-3 and ω-6 PUFA biosynthetic pathways were reconstituted in *S. cerevisiae*, using genes from *Caenorhabditis elegans*;
3. Dyer, J. M. et al. (*Appl. Env. Microbiol.*, 59:224-230 (2002)), wherein plant fatty acid desaturases (FAD2 and FAD3) were expressed in *S. cerevisiae*, leading to the production of ALA; and
4. U.S. Pat. No. 6,136,574 (Knutzon et al., Abbott Laboratories), wherein one desaturase from *Brassica napus* and two desaturases from the fungus *Mortierella alpina* were cloned into *S. cerevisiae*, leading to the production of LA, GLA, ALA and STA.

There remains a need, however, for an appropriate microbial system in which these types of genes can be expressed to provide for economical production of commercial quantities of one or more PUFAs. Additionally, a need exists for oils enriched in specific PUFAs, notably EPA and DHA.

Many microorganisms (including algae, bacteria, molds and yeasts) can synthesize oils in the ordinary course of cellular metabolism. Thus, oil production involves cultivating the microorganism in a suitable culture medium to allow for oil synthesis, followed by separation of the microorganism from the fermentation medium and treatment for recovery of the intracellular oil. Attempts have been made to optimize production of fatty acids by fermentive means involving varying such parameters as microorganisms used, media and conditions that permit oil production. However, these efforts have proved largely unsuccessful in improving yield of oil or the ability to control the characteristics of the oil composition produced.

One class or microorganisms that has not been previously examined as a production platform for PUFAs, however, are the oleaginous yeasts. These organisms can accumulate oil up to 80% of their dry cell weight. The technology for growing oleaginous yeast with high oil content is well developed (for example, see EP 0 005 277B1; Ratledge, C., *Prog. Ind. Microbiol.* 16:119-206 (1982)), and may offer a cost advantage compared to commercial micro-algae fermentation for production of ω-3 or ω-6 PUFAs. Whole yeast cells may also represent a convenient way of encapsulating ω-3 or ω-6 PUFA-enriched oils for use in functional foods and animal feed supplements.

Despite the advantages noted above, oleaginous yeast are naturally deficient in ω-6 and ω-3 PUFAs, since naturally produced PUFAs in these organisms are limited to 18:2 fatty acids (and less commonly, 18:3 fatty acids). Thus, the problem to be solved is to develop an oleaginous yeast that accumulates oils enriched in ω-3 and/or ω-6 fatty acids. Toward this end, it is necessary to introduce desaturases and elongases that allow for the synthesis and accumulation of ω-3 and/or ω-6 fatty acids in oleaginous yeasts. Although advances in the art of genetic engineering have been made, such techniques have not been developed for oleaginous yeasts. Thus, one must overcome problems associated with the use of these particular host organisms for the production of PUFAs.

Applicants have solved the stated problem by demonstrating production of PUFAs in the host *Yarrowia lipolytica*, following the introduction of a heterologous ω-6 and/or ω-3 biosynthetic pathway. Specifically, ARA (representative of ω-6 fatty acids) and EPA (representative of ω-3 fatty acids) were produced herein, to exemplify the techniques of the invention.

SUMMARY OF THE INVENTION

The present invention provides methods for the expression of enzymes comprising the ω-3/ω-6 fatty acid biosynthetic pathway in an oleaginous yeast host for the production of ω-3 and/or ω-6 fatty acids. Accordingly, the invention provides a method for the production of ω-3 and/or ω-6 fatty acids comprising:

a) providing an oleaginous yeast comprising a functional ω-3/ω-6 fatty acid biosynthetic pathway;
b) growing the yeast of step (a) in the presence of a fermentable carbon source whereby an ω-3 or ω-6 fatty acid is produced; and
c) optionally recovering the ω-3 or ω-6 fatty acid.

In one specific embodiment the invention provides a method for the production of linoleic acid comprising:

a) providing an oleaginous yeast comprising:
   (i) a gene encoding a Δ12 desaturase polypeptide; and
   (ii) an endogenous source of oleic acid;
b) growing the yeast of step (a) in the presence of a suitable fermentable carbon source wherein the gene encoding a Δ12 desaturase polypeptide is expressed and the oleic acid is converted to linoleic acid; and
c) optionally recovering the linoleic acid of step (b).

In specific embodiments the invention provides for the production of specific ω-6 fatty acids such as linoleic acid (LA), γ-linolenic acid (GLA), dihomo-γ-linoleic acid (DGLA) and arachidonic acid (ARA) by de novo biosynthesis or single step enzymatic reactions from the appropriate precursors. Similarly the invention provides for the production of specific ω-3 fatty acids such as α-linoleic acid (ALA), stearidonic acid (STA), eicosatetraenoic acid (ETA), eicosapentaenoic acid (EPA), docosapentaenoic acid (DPA) and docosahexaenoic acid by single step enzymatic reactions from the appropriate precursors.

BRIEF DESCRIPTION OF THE DRAWINGS AND SEQUENCE DESCRIPTIONS

FIG. 6 show a comparison between the DNA sequence of the *Saprolegnia diclina* Δ17 desaturase gene and the synthetic gene codon-optimized for expression in *Y. lipolytica*.

FIG. 7 illustrates the favored consensus sequences around the translation initiation codon 'ATG' in *Y. lipolytica*.

FIG. 8 illustrates the strategy utilized for in vitro synthesis of the codon-optimized Δ17 desaturase gene.

FIGS. 10A and 10B show the results of gas chromatographic analysis of fatty acids produced in *Y. lipolytica* transformed with the wildtype and synthetic codon-optimized Δ17 desaturase genes, respectively.

Figure 1:
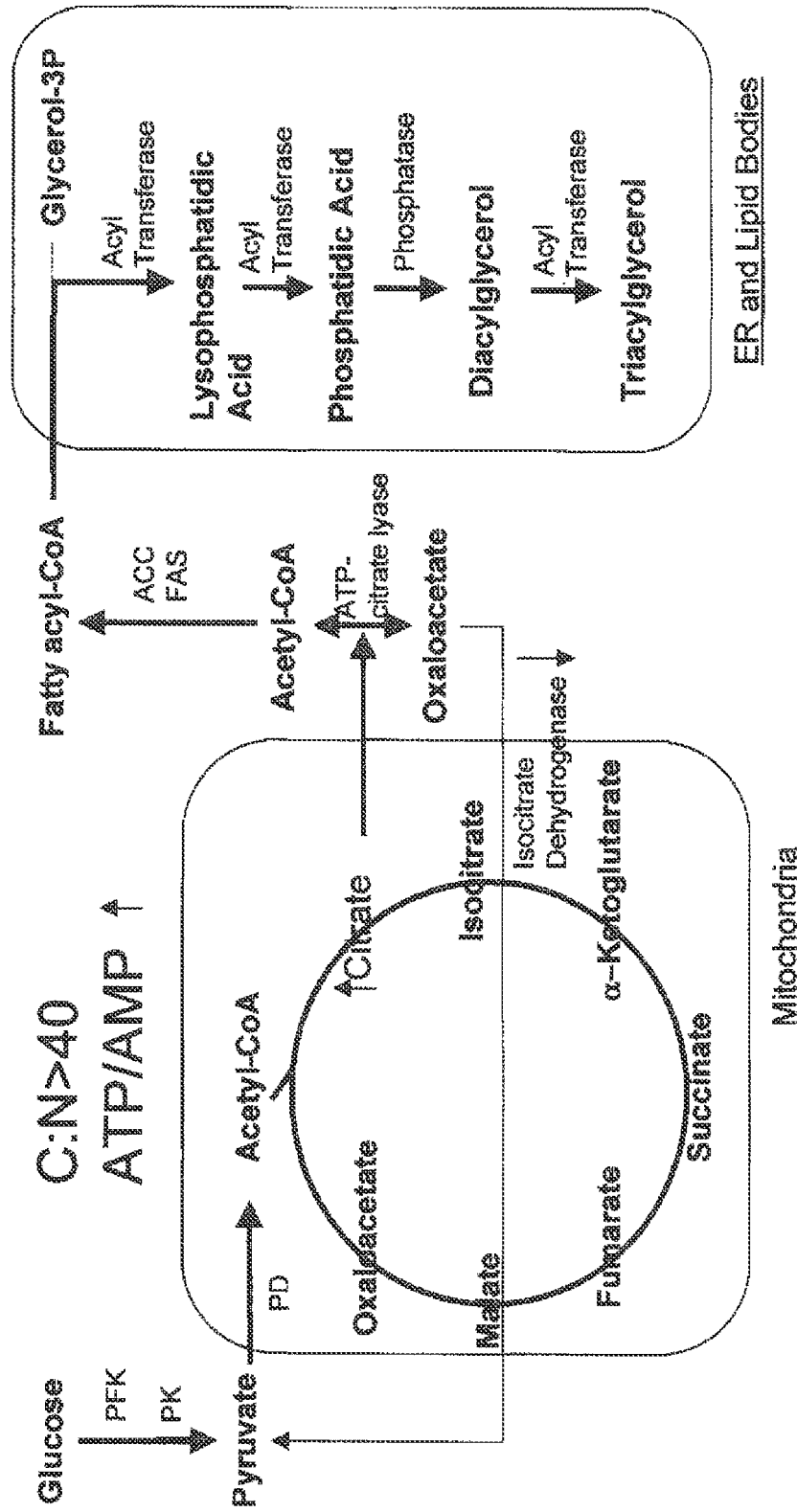
FIG. 1 shows a schematic illustration of the biochemical mechanism for lipid accumulation in oleaginous yeast.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 shows the DNA sequence of the *Mortierella alpina* Δ6 desaturase gene, while SEQ ID NO:2 shows the amino acid sequence of the *M. alpina* Δ6 desaturase.

SEQ ID NO:3 shows the DNA sequence of the *Mortierella alpina* Δ5 desaturase gene, while SEQ ID NO:4 shows the amino acid sequence of the *M. alpina* Δ5 desaturase.

SEQ ID NO:5 shows the DNA sequence of the *Saprolegnia diclina* Δ17 desaturase gene, while SEQ ID NO:6 shows the corresponding amino acid sequence of the *S. diclina* Δ17 desaturase.

SEQ ID NO:7 shows the DNA sequence of the *Mortierella alpina* high affinity elongase gene, while SEQ ID NO:8 shows the amino acid sequence of the *M. alpina* high affinity elongase.

SEQ ID NO:9 shows the DNA sequence of the synthetic Δ17 desaturase gene codon-optimized for expression in *Yarrowia lipolytica*.

SEQ ID NOs:10-31 correspond to the 11 pairs of oligonucleotides that together comprise the entire codon-optimized coding region of the *S. diclina* Δ17 desaturase gene (e.g., D17-1A, D17-1B, D17-2A, D17-2B, D17-3A, D17-3B, D17-4A, D17-4B, D17-5A, D17-5B, D17-6A, D17-6B, D17-7A, D17-7B, D17-8A, D17-8B, D17-9A, D17-9B, D17-10A, D17-10B, D17-11A and D17-11B, respectively).

SEQ ID NOs:32-37 correspond to primers D17-1, D17-4R, D17-5, D17-8D, D17-8U and D17-11, respectively, used for PCR amplification during synthesis of the codon-optimized Δ17 desaturase gene.

SEQ ID NOs:38 and 39 correspond to primers TEF5' and TEF3', respectively, used to isolate the TEF promoter.

SEQ ID NOs:40 and 41 correspond to primers XPR5' and XPR3', respectively, used to isolate the XPR2 transcriptional terminator.

SEQ ID NOs:42 and 43 correspond to primers YL21A and YL22, used for amplifying the wild type Δ17 desaturase gene of *S. diclina* from plasmid pRSP19.

SEQ ID NOs:44 and 45 correspond to primers YL53 and YL54, respectively, used for site-directed mutagenesis to generate pYSD17M.

SEQ ID NOs:46 and 47 correspond to primers KU5 and KU3, respectively, used for amplifying a 1.7 kB DNA fragment (SEQ ID NO:48; amino acid sequence provided as SEQ ID NO:49) containing the *Yarrowia* URA3 gene.

SEQ ID NOs:50 and 51 correspond to primers KI5 and KI3, respectively, used for amplifying a 1.1 kB DNA fragment (SEQ ID NO:52; amino acid sequence provided as SEQ ID NO:53) containing the conjugase gene of *Impatients balsama*.

SEQ ID NOs:54 and 55 correspond to primers KTI5 and KTI3, respectively, used for amplifying a 1.7 kB DNA fragment (SEQ ID NO:56; amino acid sequence provided as SEQ ID NO:57) containing a TEF::conjugase::XPR chimeric gene.

SEQ ID NOs:58 and 59 correspond to primers KH5 and KH3, respectively, used for amplifying a 1 kB DNA fragment (SEQ ID NO:60; amino acid sequence provided as SEQ ID NO:61) containing the *E. coli* hygromycin resistance gene.

SEQ ID NOs:62 and 63 correspond to primers KTH5 and KTH3, respectively, used for amplifying a 1.6 kB DNA fragment (SEQ ID NO:64; amino acid sequence provided as SEQ ID NO:65) containing the TEF::HPT::XPR fusion gene.

SEQ ID NOs:66 and 67 correspond to the 401 bp of 5'-sequence and 568 bp of 3'-sequence of the *Yarrowia lipolytica* URA3 gene, respectively, used to direct integration of expression cassettes into the Ura loci of the *Yarrowia* genome.

SEQ ID NOs:68-71 correspond to primers YL63, YL64, YL65 and YL66, respectively, used for site-directed mutagenesis to generate pY24-4.

SEQ ID NOs:72 and 73 correspond to primers YL11 and YL12, respectively, used for amplifying the *M. alpina* Δ5 desaturase.

SEQ ID NOs:74-77 correspond to primers YL81, YL82, YL83 and YL84, respectively, used for site-directed mutagenesis to generate pYZM5CH.

SEQ ID NOs:78 and 79 correspond to primers YL105 and YL106, respectively, used for site-directed mutagenesis to generate pYZM5CHPP.

SEQ ID NOs:80 and 81 correspond to primers YL119 and YL120, respectively, used for site-directed mutagenesis to generate pYZMSCHPPA.

SEQ ID NOs:82 and 83 correspond to primers YL121 and YL122, respectively, used for amplifying 440 bp of 5'-noncoding DNA sequence (SEQ ID NO:84) upstream from the *Y. lipolytica* URA3 gene.

SEQ ID NOs:85 and 86 correspond to primers YL114 and YL115, respectively, used for site-directed mutagenesis to generate pYZV5 and pYZV5P.

SEQ ID NO:87 corresponds to a 5.2 kB DNA fragment suitable for integration and expression of the *M. alpina* Δ5 desaturase gene in the *Yarrowia lipolytica* genome.

SEQ ID NOs:88-91 correspond to primers YL61, YL62, YL69 and YL70, respectively, used for site-directed mutagenesis to generate pY58BH.

SEQ ID NOs:92-95 correspond to primers YL77, YL78, YL79A and YL80A, respectively, used for site-directed mutagenesis to generate pY54PC.

SEQ ID NO:96 corresponds to a 8.9 kB DNA fragment suitable for integration and coordinate expression of the *M. alpina* Δ6 desaturase, *M. alpina* elongase and *M. alpina* Δ5 desaturase genes in the *Yarrowia lipolytica* genome.

SEQ ID NOs:97-100 correspond to primers YL101, YL102, YL103 and YL104, respectively, used for site-directed mutagenesis to generate pYSD17SPC.

SEQ ID NO:101 corresponds to a 10.3 kB DNA fragment suitable for integration and coordinate expression of the *M. alpina* Δ6 desaturase, *M. alpina* elongase, *M. alpina* Δ5 desaturase and codon-optimized Δ17 desaturase genes in the *Yarrowia lipolytica* genome.

SEQ ID NOs:102-113 correspond to primers YL1, YL2, YL3, YL4, YL5, YL6, YL7, YL8, YL9, YL10, YL23 and YL24, respectively, used for plasmid construction.

SEQ ID NO:114 shows the DNA sequence of the *Saprolegnia diclina* Δ5 desaturase gene, while SEQ ID NO:115 shows the amino acid sequence of the *S. diclina* Δ5 desaturase.

SEQ ID NOs:116, 117, 120, 121, 124 and 125 correspond to primers YL13A, YL14, YL19A, YL20, YL15 and YL16B, respectively, used for cloning various Δ5 desaturases.

SEQ ID NO:118 shows the DNA sequence of the *Isochrysis galbana* Δ5 desaturase gene, while SEQ ID NO:119 shows the amino acid sequence of the *I. galbana* Δ5 desaturase.

SEQ ID NO:122 shows the DNA sequence of the *Thraustochytrium aureum* Δ5 desaturase gene, while SEQ ID NO:123 shows the amino acid sequence of the *T. aureum* Δ5 desaturase.

SEQ ID NO:126 corresponds to the codon-optimized translation initiation site for genes optimally expressed in *Yarrowia* sp.

DETAILED DESCRIPTION OF THE INVENTION

In accordance with the subject invention, Applicants provide methods for the production of ω-3 and/or ω-6 fatty acids in oleaginous yeasts. Specifically, Applicants provide methods for production of linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid and docosahexaenoic acid. This is accomplished by introduction of functional ω-3/ω-6 fatty acid biosynthetic pathway encoded by genes conferring Δ17 desaturase, Δ6 desaturase, Δ5 desaturase, Δ9 desaturase, Δ12 desaturase, Δ15 desaturase, Δ4 desaturase and elongase activities into oleaginous yeast hosts for recombinant expression. Thus, this disclosure demonstrates that oleaginous yeasts can be engineered to enable production of any PUFA composition that is desired.

The subject invention finds many applications. PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with arachidonic acid (ARA) can result not only in increased levels of ARA, but also downstream products of ARA such as prostaglandins. Complex regulatory mechanisms can make it desirable to combine various PUFAs, or add different conjugates of PUFAs, in order to prevent, control or overcome such mechanisms to achieve the desired levels of specific PUFAs in an individual.

Definitions

In this disclosure, a number of terms and abbreviations are used. The following definitions are provided.

"Open reading frame" is abbreviated ORF.
"Polymerase chain reaction" is abbreviated PCR.
"American Type Culture Collection" is abbreviated ATCC.
"Polyunsaturated fatty acid(s)" is abbreviated PUFA(s).

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" are cis-isomers that have "double bonds" along their carbon backbones. "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

"PUFAs" can be classified into two major families (depending on the position (n) of the first double bond nearest the methyl end of the fatty acid carbon chain). Thus, the "ω-6 fatty acids" (ω-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "ω-3 fatty acids" (ω-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

For the purposes of the present disclosure, the omega-reference system will be used to indicate the number of carbons, the number of double bonds and the position of the double bond closest to the omega carbon, counting from the omega carbon (which is numbered 1 for this purpose). This nomenclature is shown below in Table 1, in the column titled "Shorthand Notation". The remainder of the Table summarizes the common names of ω-3 and ω-6 fatty acids, the abbreviations that will be used throughout the specification and each compounds' chemical name.

TABLE 1

Nomenclature of Polyunsaturated Fatty Acids

| Common Name | Abbreviation | Chemical Name | Shorthand Notation |
|---|---|---|---|
| Linoleic | LA | cis-9,12-octadecadienoic | 18:2 ω-6 |
| γ-Linoleic | GLA | cis-6, 9, 12-octadecatrienoic | 18:3 ω-6 |
| Dihomo-γ-Linoleic | DGLA | cis-8, 11, 14-eicosatrienoic | 20:3 ω-6 |
| Arachidonic | ARA | cis-5, 8, 11, 14-eicosatetraenoic | 20:4 ω-6 |
| α-Linolenic | ALA | cis-9, 12, 15-octadecatrienoic | 18:3 ω-3 |
| Stearidonic | STA | cis-6, 9, 12, 15-octadecatetraenoic | 18:4 ω-3 |
| Eicosa-tetraenoic | ETA | cis-8, 11, 14, 17-eicosatetraenoic | 20:4 ω-3 |
| Eicosa-pentaenoic | EPA | cis-5, 8, 11, 14, 17-eicosapentaenoic | 20:5 ω-3 |
| Docosa-pentaenoic | DPA | cis-7, 10, 13, 16, 19-docosapentaenoic | 22:5 ω-3 |
| Docosa-hexaenoic | DHA | cis-4, 7, 10, 13, 16, 19-docosahexaenoic | 22:6 ω-3 |

The term "essential fatty acid" refers to a particular PUFA that an organism must ingest in order to survive, being unable to synthesize the particular essential fatty acid de novo. For example, mammals can not synthesize the essential fatty acid LA (18:2, ω-6). Other essential fatty acids include GLA (ω-6), DGLA (ω-6), ARA (ω-6), EPA (ω-3) and DHA (ω-3).

The term "fat" refers to a lipid substance that is solid at 25° C. and usually saturated.

The term "oil" refers to a lipid substance that is liquid at 25° C. and usually polyunsaturated. PUFAs are found in the oils of some algae, oleaginous yeasts and filamentous fungi. "Microbial oils" or "single cell oils" are those oils naturally produced by microorganisms during their lifespan. Such oils can contain long chain PUFAs.

The term "PUFA biosynthetic pathway enzyme" refers to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase and/or an elongase.

Figure 2:
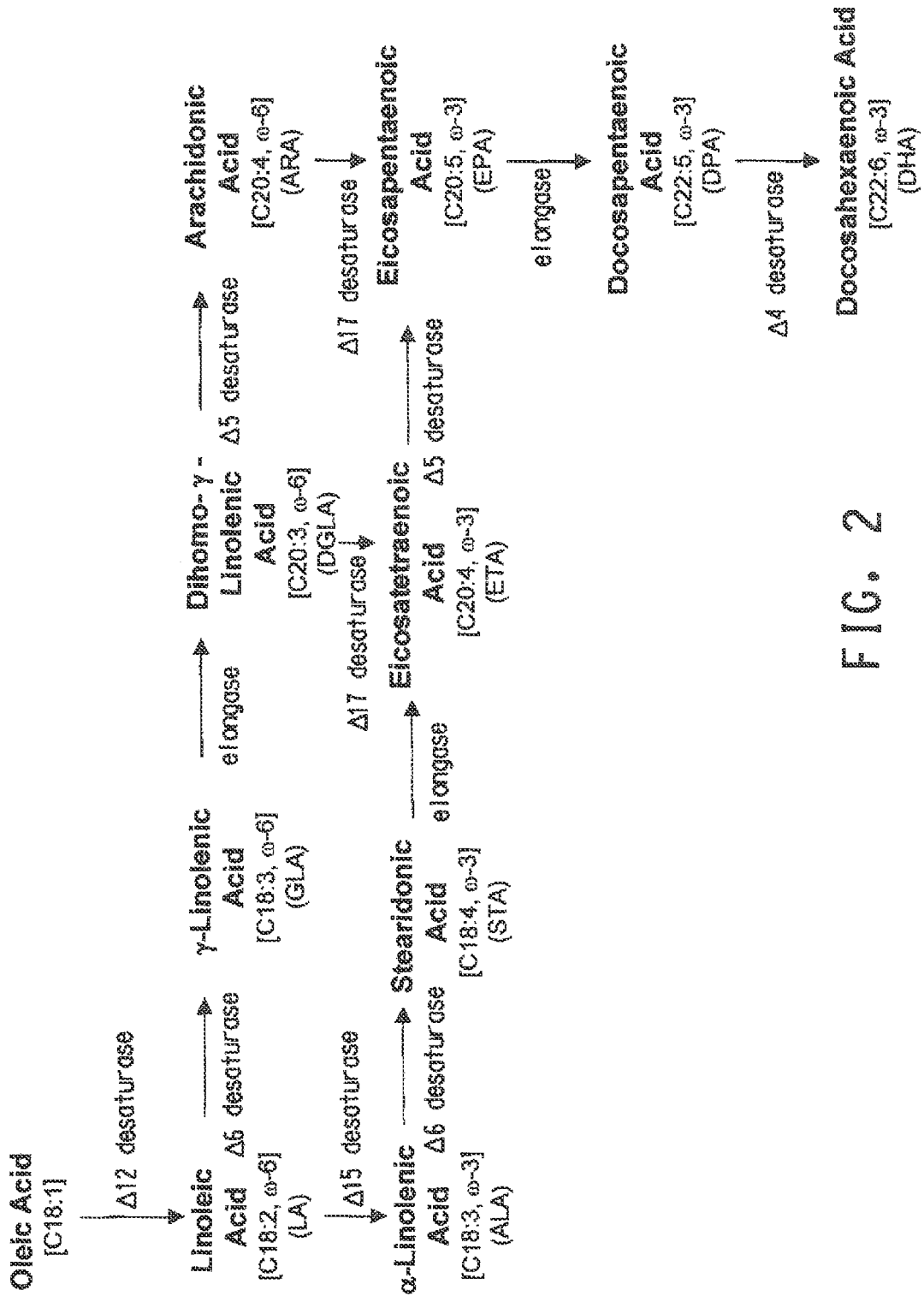
FIG. 2 illustrates the ω-3/ω-6 fatty acid biosynthetic pathway.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode some or all of the following enzymes: Δ12 desaturase, Δ6 desaturase, elongase, Δ5 desaturase, Δ17 desaturase, Δ15 desaturase, Δ9 desaturase and Δ4 desaturase. A representative pathway is illustrated in FIG. 2, which demonstrates how both ω-3 and ω-6 fatty acids may be produced from a common source. The term "functional" as used herein in context with the ω-3/ω-6 fatty acid biosynthetic pathway means that some or all of the genes in the pathway express active enzymes. It should be understood that "ω-3/ω-6 fatty acid biosynthetic pathway" or "functional ω-3/ω-6 fatty acid biosynthetic pathway" does not imply that all the genes listed in this paragraph are required as a number of fatty acid products will only require the expression of a subset of the genes of this pathway.

The term "desaturase" refers to a polypeptide component of a multi-enzyme complex that can desaturate one or more fatty acids to produce a mono- or polyunsaturated fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are: 1.) Δ17 desaturases that desaturate a fatty acid between the 17th and 18th carbon atom numbered from the carboxyl-terminal end of the molecule and which, for example, catalyze the conversion of ARA to EPA and/or DGLA to ETA; 2.) Δ6 desaturases that catalyze the conversion of LA to GLA and/or ALA to STA; 3.) Δ5 desaturases that catalyze the conversion of DGLA to ARA and/or ETA to EPA; 4.) Δ4 desaturases that catalyze the conversion of DPA to DHA; 5.) Δ12 desaturases that catalyze the conversion of oleic acid to LA; 6.) Δ15 desaturases that catalyze the conversion of LA to ALA; and 7.) Δ9 desaturases that catalyze the conversion of palmitate to palmitoleic acid (16:1) and/or stearate to oleic acid (18:1).

The term "elongase" refers to a polypeptide component of a multi-enzyme complex that can elongate a fatty acid carbon chain to produce a mono- or polyunsaturated fatty acid that is 2 carbons longer than the fatty acid substrate that the elongase acts upon. This process of elongation occurs in a multi-step mechanism in association with fatty acid synthase, whereby CoA is the acyl carrier (Lassner et al., *The Plant Cell* 8:281-292 (1996)). Briefly, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongases are the conversion of GLA to DGLA, STA to ETA and EPA to DPA. Accordingly, elongases can have different specificities (e.g., a $C_{16/18}$ elongase will prefer a $C_{16}$ substrate, a $C_{18/20}$ elongase will prefer a $C_{18}$ substrate and a $C_{20/22}$ elongase will prefer a $C_{20}$ substrate).

The term "high affinity elongase" refers to an elongase whose substrate specificity is preferably for GLA (with DGLA as a product of the elongase reaction). One such elongase is described in WO 00/12720.

The terms "conversion efficiency" and "percent substrate conversion" refer to the efficiency by which a particular enzyme (e.g., a desaturase or elongase) can convert substrate to product. The conversion efficiency is measured according to the following formula: ([product]/[substrate+product])*100, where 'product' includes the immediate product and all products in the pathway derived from it.

The term "oleaginous" refers to those organisms that tend to store their energy source in the form of lipid (Weete, In: Fungal Lipid Biochemistry, $2^{nd}$ Ed., Plenum, 1980). Generally, the cellular PUFA content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)).

The term "oleaginous yeast" refers to those microorganisms classified as yeasts that can accumulate at least 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "fermentable carbon source" means a carbon source that a microorganism will metabolize to derive energy. Typical carbon sources of the invention include, but are not limited to: monosaccharides, oligosaccharides, polysaccharides, alkanes, fatty acids, esters of fatty acids, monoglycerides, diglycerides, triglycerides, carbon dioxide, methanol, formaldehyde, formate and carbon-containing amines.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "complementary" is used to describe the relationship between nucleotide bases that are capable of hybridizing to one another. For example, with respect to DNA, adenosine is complementary to thymine and cytosine is complementary to guanine.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures; or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense"

RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragments of the invention. Expression may also refer to translation of mRNA into a polypeptide.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, 2nd ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Microbial Biosynthesis of Fatty Acids

In general, lipid accumulation in oleaginous microorganisms is triggered in response to the overall carbon to nitrogen ratio present in the growth medium (FIG. 1). When cells have exhausted available nitrogen supplies (e.g., when the carbon to nitrogen ratio is greater than about 40), the depletion of cellular adenosine monophosphate (AMP) leads to the cessation of AMP-dependent isocitrate dehydrogenase activity in the mitochondria and the accumulation of citrate, transport of citrate into the cytosol and subsequent cleavage of the citrate by ATP-citrate lyase to yield acetyl-CoA and oxaloacetate. Acetyl-CoA is the principle building block for de novo biosynthesis of fatty acids. Although any compound that can effectively be metabolized to produce acetyl-CoA can serve as a precursor of fatty acids, glucose is the primary source of carbon in this type of reaction (FIG. 1). Glucose is converted to pyruvate via glycolysis and pyruvate is then transported into the mitochondria where it can be converted to acetyl-CoA by pyruvate dehydrogenase ("PD"). Since acetyl-CoA cannot be transported directly across the mitochondrial membrane into the cytoplasm, the two carbons from acetyl-CoA condense with oxaloacetate to yield citrate (catalyzed by citrate synthase). Citrate is transported directly into the cytoplasm, where it is cleaved by ATP-citrate lyase to regenerate acetyl-CoA and oxaloacetate. The oxaloacetate reenters the tricarboxylic acid cycle, via conversion to malate.

The synthesis of malonyl-CoA is the first committed step of fatty acid biosynthesis, which takes place in the cytoplasm. Malonyl-CoA is produced via carboxylation of acetyl-CoA by acetyl-CoA carboxylase ("ACC"). Fatty acid synthesis is catalyzed by a multi-enzyme fatty acid synthase complex ("FAS") and occurs by the condensation of eight two-carbon fragments (acetyl groups from acetyl-CoA) to form a 16-carbon saturated fatty acid, palmitate. More specifically, FAS catalyzes a series of 7 reactions, which involve the following (Smith, S. *FASEB J.*, 8(15):1248-59 (1994)):

1. Acetyl-CoA and malonyl-CoA are transferred to the acyl carrier peptide (ACP) of FAS. The acetyl group is then transferred to the malonyl group, forming β-ketobutyryl-ACP and releasing $CO_2$.
2. The β-ketobutyryl-ACP undergoes reduction (via β-ketoacyl reductase) and dehydration (via β-hydroxyacyl dehydratase) to form a trans-monounsaturated fatty acyl group.
3. The double bond is reduced by NADPH, yielding a saturated fatty-acyl group two carbons longer than the initial one. The butyryl-group's ability to condense with a new malonyl group and repeat the elongation process is then regenerated.

4. When the fatty acyl group becomes 16 carbons long, a thioesterase activity hydrolyses it, releasing free palmitate.

Palmitate (16:0) is the precursor of longer chain saturated and unsaturated fatty acids (e.g., stearic (18:0), palmitoleic (16:1) and oleic (18:1) acids) through the action of elongases and desaturases present in the endoplasmic reticulum membrane. Palmitate and stearate are converted to their unsaturated derivatives, palmitoleic (16:1) and oleic (18:1) acids, respectively, by the action of a Δ9 desaturase.

Triacylglycerols (the primary storage unit for fatty acids) are formed by the esterification of two molecules of acyl-CoA to glycerol-3-phosphate to yield 1,2-diacylglycerol phosphate (commonly identified as phosphatidic acid) (FIG. 1). The phosphate is then removed, by phosphatidic acid phosphatase, to yield 1,2-diacylglycerol. Triacylglycerol is formed upon the addition of a third fatty acid by the action of a diacylglycerol-acyl transferase.

Biosynthesis of Omega-3 and Omega-6 Fatty Acids

Simplistically, the metabolic process that converts LA to GLA, DGLA and ARA (the ω-6 pathway) and ALA to STA, ETA, EPA and DHA (the ω-3 pathway) involves elongation of the carbon chain through the addition of carbon atoms and desaturation of the molecule through the addition of double bonds (FIG. 2). This requires a series of special desaturation and elongation enzymes present in the endoplasmic reticulim membrane.

ω-6 Fatty Acids

Oleic acid is converted to LA (18:2), the first of the ω-6 fatty acids, by the action of a Δ12 desaturase. Subsequent ω-6 fatty acids are produced as follows: 1.) LA is converted to GLA by the activity of a Δ6 desaturase; 2.) GLA is converted to DGLA by the action of an elongase; and 3.) DGLA is converted to ARA by the action of a Δ5 desaturase.

ω-3 Fatty Acids

Linoleic acid (LA) is converted to ALA, the first of the ω-3 fatty acids, by the action of a Δ15 desaturase. Subsequent ω-3 fatty acids are produced in a series of steps similar to that for the ω-6 fatty acids. Specifically: 1.) ALA is converted to STA by the activity of a Δ6 desaturase; 2.) STA is converted to ETA by the activity of an elongase; and 3.) ETA is converted to EPA by the activity of a Δ5 desaturase. Alternatively, ETA and EPA can be produced from DGLA and ARA, respectively, by the activity of a Δ17 desaturase. EPA can be further converted to DHA by the activity of an elongase and a Δ4 desaturase.

Genes Involved in Omega Fatty Acid Production

Many microorganisms, including algae, bacteria, molds and yeasts, can synthesize PUFAs and omega fatty acids in the ordinary course of cellular metabolism. Particularly well-studied are fungi including *Schizochytrium aggregatm*, species of the genus *Thraustochytrium* and *Mortierella alpina*. Additionally, many dinoflagellates (Dinophyceaae) naturally produce high concentrations of PUFAs. As such, a variety of genes involved in oil production have been identified through genetic means and the DNA sequences of some of these genes are publicly available (non-limiting examples are shown below in Table 2):

TABLE 2

Some Publicly Available Genes Involved In PUFA Production

| Genbank Accession No. | Description |
|---|---|
| AY131238 | *Argania spinosa* Δ6 desaturase |
| Y055118 | *Echium pitardii var. pitardii* Δ6 desaturase |
| AY055117 | *Echium gentianoides* Δ6 desaturase |
| AF296076 | *Mucor rouxii* Δ6 desaturase |
| AF007561 | *Borago officinalis* Δ6 desaturase |
| L11421 | *Synechocystis* sp. Δ6 desaturase |
| NM_031344 | *Rattus norvegicus* Δ6 fatty acid desaturase |
| AF465283, AF465281, AF110510 | *Mortierella alpina* Δ6 fatty acid desaturase |
| AF465282 | *Mortierella isabellina* Δ6 fatty acid desaturase |
| AF419296 | *Pythium irregulare* Δ6 fatty acid desaturase |
| AB052086 | *Mucor circinelloides* D6d mRNA for Δ6 fatty acid desaturase |
| AJ250735 | *Ceratodon purpureus* mRNA for Δ6 fatty acid desaturase |
| AF126799 | *Homo sapiens* Δ6 fatty acid desaturase |
| AF126798 | *Mus musculus* Δ6 fatty acid desaturase |
| AF199596, AF226273 | *Homo sapiens* Δdesaturase |
| AF320509 | *Rattus norvegicus* liver Δ5 desaturase |
| AB072976 | *Mus musculus* D5D mRNA for Δ5 desaturase |
| AF489588 | *Thraustochytrium* sp. ATCC21685 Δ5 fatty acid desaturase |
| AJ510244 | *Phytophthora megasperma* mRNA for Δ5 fatty acid desaturase |
| AF419297 | *Pythium irregulare* Δ5 fatty acid desaturase |
| AF07879 | *Caenorhabditis elegans* Δ5 fatty acid desaturase |
| AF067654 | *Mortierella alpina* Δ5 fatty acid desaturase |
| AB022097 | *Dictyostelium discoideum* mRNA for Δ5 fatty acid desaturase |
| AF489589.1 | *Thraustochytrium* sp. ATCC21685 Δ4 fatty acid desaturase |
| AY332747 | *Pavlova lutheri* Δ4 fatty acid desaturase (des1) mRNA |
| AAG36933 | *Emericella nidulans* oleate Δ12 desaturase |
| AF110509, AB020033 | *Mortierella alpina* Δ12 fatty acid desaturase mRNA |
| AAL13300 | *Mortierella alpina* Δ12 fatty acid desaturase |
| AF417244 | *Mortierella alpina* ATCC 16266 Δ12 fatty acid desaturase |
| AF161219 | *Mucor rouxii* Δ12 desaturase mRNA |
| X86736 | *Spiruline platensis* Δ12 desaturase |
| AF240777 | *Caenorhabditis elegans* Δ12 desaturase |
| AB007640 | *Chlamydomonas reinhardtii* Δ12 desaturase |
| AB075526 | *Chlorella vulgaris* Δ12 desaturase |
| AP002063 | *Arabidopsis thaliana* microsomal Δ12 desaturase |
| NP_441622, BAA18302, BAA02924 | *Synechocystis sp.* PCC 6803 Δ15 desaturase |
| AAL36934 | *Perilla frutescens* Δ15 desaturase |
| AF338466 | *Acheta domesticus* Δ9 desaturase 3 mRNA |
| AF438199 | *Picea glauca* desaturase Δ9 (Des9) mRNA |
| E11368 | *Anabaena* Δ9 desaturase |
| E11367 | *Synechocystis* Δ9 desaturase |
| D83185 | *Pichia angusta* DNA for Δ9 fatty acid desaturase |
| U90417 | *Synechococcus vulcanus* Δ9 acyl-lipid fatty acid desaturase (desC) gene |
| AF085500 | *Mortierella alpina* Δ9 desaturase mRNA |
| AY504633 | *Emericella nidulans* Δ9 stearic acid desaturase (sdeB) gene |
| NM_069854 | *Caenorhabditis elegans* essential fatty acid desaturase, stearoyl-CoA desaturase (39.1 kD) (fat-6) complete mRNA |
| AF230693 | *Brassica oleracea* cultivar Rapid Cycling stearoyl-ACP desaturase (Δ9-BO-1) gene, exon sequence |
| AX464731 | *Mortierella alpina* elongase gene (also WO 02/08401) |
| NM_119617 | *Arabidopsis thaliana* fatty acid elongase 1 (FAE1) (At4g34520) mRNA |
| NM_134255 | *Mus musculus* ELOVL family member 5, elongation of long chain fatty acids (yeast) (Elovl5), mRNA |
| NM_134383 | *Rattus norvegicus* fatty acid elongase 2 (rELO2), mRNA |
| NM_134382 | *Rattus norvegicus* fatty acid elongase 1 (rELO1), mRNA |
| NM_068396, NM_068392, NM_070713, NM_068746, NM_064685 | *Caenorhabditis elegans* fatty acid ELOngation (elo-6), (elo-5), (elo-2), (elo-3), and (elo-9) mRNA |

Additionally, the patent literature provides many additional DNA sequences of genes (and/or details concerning several of the genes above and their methods of isolation) involved in PUFA production. See, for example: U.S. Pat. No. 5,968,809 (Δ6 desaturases); U.S. Pat. No. 5,972,664 and U.S. Pat. No. 6,075,183 (Δ5 desaturases); WO 91/13972 and U.S. Pat. No. 5,057,419 (Δ9 desaturases); WO 93/11245 (Δ15 desaturases); WO 94/11516, U.S. Pat. No. 5,443,974 and WO 03/099216 (Δ12 desaturases); U.S. 2003/0196217 A1 (Δ17 desaturase); WO 02/090493 (Δ4 desaturases); and, WO 00/12720 and U.S. 2002/0139974A1 (elongases). Each of these patents and applications are herein incorporated by reference in their entirety.

As will be obvious to one skilled in the art, the particular functionalities required to be introduced into a host organism for production of a particular PUFA final product will depend on the host cell (and its native PUFA profile and/or desaturase profile), the availability of substrate and the desired end product(s). As shown in FIG. 2, LA, GLA, DGLA, ARA, ALA, STA, ETA, EPA, DPA and DHA may all be produced in oleaginous yeasts, by introducing various combinations of the following PUFA enzyme functionalities: a Δ4 desaturase, a Δ5 desaturase, a Δ6 desaturase, a Δ12 desaturase, a Δ15 desaturase, a Δ17 desaturase, a Δ9 desaturase and/or an elongase. One skilled in the art will be able to identify various candidate genes encoding each of the above enzymes, according to publicly available literature (e.g., GenBank), the patent literature, and experimental analysis of microorganisms having the ability to produce PUFAs. The sequences may be derived from any source, e.g., isolated from a natural source (from bacteria, algae, fungi, plants, animals, etc.), produced via a semi-synthetic route or synthesized de novo. In some embodiments, manipulation of genes endogenous to the host is preferred; for other purposes, it is necessary to introduce heterologous genes.

Although the particular source of the desaturase and elongase genes introduced into the host is not critical to the invention, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or 4.) co-factors required by the polypeptide. The expressed polypeptide preferably has parameters compatible with the biochemical environment of its location in the host cell. For example, the polypeptide may have to compete for substrate with other enzymes in the host cell. Analyses of the $K_M$ and specific activity of the polypeptide are therefore considered in determining the suitability of a given polypeptide for modifying PUFA production in a given host cell. The polypeptide used in a particular host cell is one that can function under the biochemical conditions present in the intended host cell but otherwise can be any polypeptide having desaturase or elongase activity capable of modifying the desired PUFA.

Endogenous PUFA Genes

In some cases, the host organism in which it is desirable to produce PUFAs will possess endogenous genes encoding some PUFA biosynthetic pathway enzymes. For example, oleaginous yeast can typically produce 18:2 fatty acids (and some have the additional capability of synthesizing 18:3 fatty acids); thus, oleaginous yeast typically possess native Δ12 desaturase activity and may also have Δ15 desaturases. In some embodiments, therefore, expression of the native desaturase enzyme is preferred over a heterologous (or "foreign") enzyme since: 1.) the native enzyme is optimized for interaction with other enzymes and proteins within the cell; and 2.) heterologous genes are unlikely to share the same codon preference in the host organism. Additionally, advantages are incurred when the sequence of the native gene is known, as it permits facile disruption of the endogenous gene by targeted disruption.

Heterologous PUFA Genes

In many instances, the appropriate desaturases and elongases are not present in the host organism of choice to enable production of the desired PUFA products. Thus, it is necessary to introduce heterologous genes.

For the purposes of the present invention herein, it was desirable to demonstrate an example of the introduction of an ω-3 and/or ω-6 biosynthetic pathway into an oleaginous host organism; and thus, a *Mortierella alpina* Δ5 desaturase, *M. alpina* Δ6 desaturase, *Saprolegnia diclina* Δ17 desaturase and *M. alpina* elongase were introduced into *Yarrowia lipolytica*. However, the specific enzymes (and genes encoding those enzymes) introduced into the host organism and the specific PUFAs produced are by no means limiting to the invention herein.

If one desired to produce EPA, as demonstrated herein, it will be obvious to one skilled in the art that numerous other genes derived from different sources would be suitable to introduce Δ5 desaturase, Δ6 desaturase, Δ17 desaturase and elongase activity into the preferred microbial host. Thus, in one embodiment of the present invention, other DNAs which are substantially identical to the *M. alpina* Δ6 desaturase, Δ5 desaturase and high-affinity PUFA elongase and the *S. diclina* Δ17 desaturase also can be used for production of ω-6 and/or ω-3 fatty acids (e.g., EPA) in oleaginous yeast. By "substantially identical" is intended an amino acid sequence or nucleic acid sequence exhibiting in order of increasing preference at least 80%, 90% or 95% homology to the selected polypeptides, or nucleic acid sequences encoding the amino acid sequence. For polypeptides, the length of comparison sequences generally is at least 16 amino acids, preferably at least 20 amino acids or most preferably 35 amino acids. For nucleic acids, the length of comparison sequences generally is at least 50 nucleotides, preferably at least 60 nucleotides, more preferably at least 75 nucleotides, and most preferably 110 nucleotides.

Homology typically is measured using sequence analysis software, wherein the term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc., Madison, Wis.); and 4.) the FASTA program incorporating the Smith-Waterman algorithm (W. R. Pearson, Comput. Methods Genome Res., [Proc. Int. Symp.] (1994), Meeting Date 1992, 111-20. Suhai, Sandor, Ed. Plenum: New York, N.Y.). Within the context of this application it will be understood that where sequence analysis software is used for analysis, the results of the analysis will be based on the "default values" of the program referenced, unless otherwise specified. As used herein "default values" will mean any set of values or parameters that originally load with the software when first initialized. In general, such computer software matches similar sequences by assigning degrees of homology to various substitutions, deletions, and other modifications.

Additionally it will be appreciated by one of skill in the art that polypeptides may have amino acids conservatively substituted in a manner such that the function of the polypeptide is not altered or compromised. Polypeptides having the desaturase and elongase activities as described herein and possessing such conservative substitutions are considered within the scope of the present invention. Conservative substitutions typically include substitutions within the following groups: 1.) glycine and alanine; 2.) valine, isoleucine and leucine; 3.) aspartic acid, glutamic acid, asparagine and glutamine; 4.) serine and threonine; 5.) lysine and arginine; and 6.) phenylalanine and tyrosine. Substitutions may also be made on the basis of conserved hydrophobicity or hydrophilicity (Kyte and Doolittle, *J. Mol. Biol.* 157:105-132 (1982)), or on the basis of the ability to assume similar polypeptide secondary structure (Chou and Fasman, *Adv. Enzymol.* 47:45-148 (1978)).

In alternate embodiments of the invention, other DNAs which, although not substantially identical to the *M. alpina* Δ6 desaturase, Δ5 desaturase and high-affinity PUFA elongase and the *S. diclina* Δ17 desaturase, also can be used for the purposes herein (e.g., for production of ω-3 and/or ω-6 PUFAs such as ARA and EPA). For example, DNA sequences encoding Δ6 desaturase polypeptides that would be useful for introduction into an oleaginous yeast according to the teachings of the present invention may be obtained from microorganisms having an ability to produce GLA or STA. Such microorganisms include, for example, those belonging to the genera *Mortierella, Conidiobolus, Pythium, Phytophathora, Penicillium, Porphyridium, Coidosporium, Mucor, Fusarium, Aspergillus, Rhodotorula* and *Entomophthora*. Within the genus *Porphyridium*, of particular interest is *P. cruentum*. Within the genus *Mortierella*, of particular interest are *M. elongata, M. exigua, M. hygrophila, M. ramanniana* var. *angulispora* and *M. alpina*. Within the genus *Mucor*, of particular interest are *M. circinelloides* and *M. javanicus*.

Alternatively, a related desaturase that is not substantially identical to the *M. alpina* Δ6 desaturase, but which can desaturate a fatty acid molecule at carbon 6 from the carboxyl end of the molecule would also useful in the present invention as a Δ6 desaturase, assuming the desaturase can still effectively convert LA to GLA and/or ALA to STA. As such, related desaturases and elongases can be identified by their ability of function substantially the same as the desaturases and elongase disclosed herein.

In summary, genes encoding PUFA biosynthetic pathway enzymes suitable for the purposes herein may be isolated from a variety of sources. Desaturases for the purposes herein are characterized by the ability to: 1.) desaturate a fatty acid between the $17^{th}$ and $18^{th}$ carbon atom numbered from the carboxyl-terminal end of the molecule and catalyze the conversion of ARA to EPA and DGLA to ETA (Δ17 desaturases); 2.) catalyze the conversion of LA to GLA and/or ALA to STA (Δ6 desaturases); 3.) catalyze the conversion of DGLA to ARA and/or ETA to EPA (Δ5 desaturases); 4.) catalyze the conversion of DPA to DHA (Δ4 desaturases); 5.) catalyze the conversion of oleic acid to LA (Δ12 desaturases); 6.) catalyze the conversion of LA to ALA (Δ15 desaturases); and/or 7.) catalyze the conversion of palmitate to palmitoleic acid and/or stearate to oleic acid (Δ9 desaturases). In like manner, suitable elongases for the purposes herein are not limited to those from a specific source; instead, the enzymes having use for the purposes herein are characterized by their ability to elongate a fatty acid carbon chain by 2 carbons relative to the substrate the elongase acts upon, to thereby produce a mono- or polyunsaturated fatty acid.

Optimization of Omega Fatty Acid Genes for Expression in Particular Organisms

Although the particular source of a PUFA desaturase or elongase is not critical in the invention herein, it will be obvious to one of skill in the art that heterologous genes will be expressed with variable efficiencies in an alternate host. Thus, ω-3 and/or ω-6 PUFA production may be optimized by selection of a particular desaturase or elongase whose level of expression in a heterologous host is preferred relative to the expression of an alternate desaturase or elongase in the host organism of interest. Furthermore, it may be desirable to modify the expression of particular PUFA biosynthetic pathway enzymes to achieve optimal conversion efficiency of each, according to the specific PUFA product composition of interest. A variety of genetic engineering techniques are available to optimize expression of a particular enzyme. Two such techniques include codon optimization and gene mutation, as described below. Genes produced by. e.g., either of these two methods, having desaturase and/or elongase activity(s) would be useful in the invention herein for synthesis of ω-3 and/or ω-6 PUFAs.

Codon Optimization

As will be appreciated by one skilled in the art, it is frequently useful to modify a portion of the codons encoding a particular polypeptide that is to be expressed in a foreign host, such that the modified polypeptide uses codons that are preferred by the alternate host. Use of host-preferred codons can substantially enhance the expression of the foreign gene encoding the polypeptide.

In general, host-preferred codons can be determined within a particular host species of interest by examining codon usage in proteins (preferably those expressed in the largest amount) and determining which codons are used with highest frequency. Then, the coding sequence for a polypeptide of interest having desaturase or elongase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

In the present invention, it was desirable to modify a portion of the codons encoding the polypeptide having Δ17 desaturase activity, to enhance the expression of the gene in *Yarrowia lipolytica*. The nucleic acid sequence of the native gene (e.g., the *Saprolegnia diclina* Δ17 desaturase) was modified to employ host-preferred codons. The skilled artisan will appreciate that this optimization method will be equally applicable to other genes in the ω-3/ω-6 fatty acids biosynthetic pathway (see for example, co-pending U.S. Provisional Application No. 60/468,718, herein incorporated entirely by reference). Furthermore, modulation of the *S. diclina* Δ17 desaturase is only exemplary.

Gene Mutation

Methods for synthesizing sequences and bringing sequences together are well established in the literature. For example, in vitro mutagenesis and selection, site-directed mutagenesis, error prone PCR (Melnikov et al., *Nucleic Acids Research*, 27(4):1056-1062 (Feb. 15, 1999)), "gene shuffling" or other means can be employed to obtain mutations of naturally occurring desaturase or elongase genes. This would permit production of a polypeptide having desaturase or elongase activity, respectively, in vivo with more desirable physical and kinetic parameters for function in the host cell such as a longer half-life or a higher rate of production of a desired PUFA.

If desired, the regions of a polypeptide of interest (i.e., a desaturase or an elongase) important for enzymatic activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after the 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR, while point mutations are made through techniques such as site-directed mutagenesis or mutagenic PCR.

Chemical mutagenesis also can be used for identifying regions of a desaturase or elongase polypeptide important for activity. A mutated construct is expressed, and the ability of the resulting altered protein to function as a desaturase or elongase is assayed. Such structure-function analysis can determine which regions may be deleted, which regions tolerate insertions, and which point mutations allow the mutant protein to function in substantially the same way as the native desaturase or native elongase. All such mutant proteins and nucleotide sequences encoding them that are derived from the codon-optimized gene described herein are within the scope of the present invention.

In the present invention, it was desirable to modify a portion of the codons encoding the polypeptide having $\Delta 17$ desaturase activity, to enhance the expression of the gene in Yarrowia lipolytica. The nucleic acid sequence of the native gene (e.g., the S. diclina $\Delta 17$ desaturase) was modified to employ host preferred codons. The skilled artisan will appreciate that these optimization methods will be equally applicable to other genes in the $\omega$-3/$\omega$-6 fatty acids biosynthetic pathway and that modulation of the S. diclina $\Delta 17$ desaturase and M. alpina $\Delta 6$ desaturase, $\Delta 5$ desaturase are only exemplary.

Microbial Production of $\omega$-3 and/or $\omega$-6 Fatty Acids

Microbial production of $\omega$-3 and/or $\omega$-6 fatty acids has several advantages over purification from natural sources such as fish or plants. For example:

1.) Many microbes are known with greatly simplified oil compositions compared with those of higher organisms, making purification of desired components easier;
2.) Microbial production is not subject to fluctuations caused by external variables, such as weather and food supply;
3.) Microbially produced oil is substantially free of contamination by environmental pollutants;
4.) Microbes can provide PUFAs in particular forms which may have specific uses; and
5.) Microbial oil production can be manipulated by controlling culture conditions, notably by providing particular substrates for microbially expressed enzymes, or by addition of compounds/genetic engineering to suppress undesired biochemical pathways.

In addition to these advantages, production of $\omega$-3 and/or $\omega$-6 fatty acids from recombinant microbes provides the ability to alter the naturally occurring microbial fatty acid profile by providing new biosynthetic pathways in the host or by suppressing undesired pathways, thereby increasing levels of desired PUFAs, or conjugated forms thereof, and decreasing levels of undesired PUFAs. For example, it is possible to modify the ratio of $\omega$-3 to $\omega$-6 fatty acids so produced, produce either $\omega$-3 or $\omega$-6 fatty acids exclusively while eliminating production of the alternate omega fatty acid, or engineer production of a specific PUFA without significant accumulation of other PUFA downstream or upstream products.

Expression Systems, Cassettes and Vectors

The genes and gene products described herein may be produced in heterologous microbial host cells, particularly in the cells of oleaginous yeasts (e.g., Yarrowia lipolytica). Expression in recombinant microbial hosts may be useful for the production of various PUFA pathway intermediates, or for the modulation of PUFA pathways already existing in the host for the synthesis of new products heretofore not possible using the host.

Microbial expression systems and expression vectors containing regulatory sequences that direct high level expression of foreign proteins are well known to those skilled in the art. Any of these could be used to construct chimeric genes for production of any of the gene products of the preferred desaturase and/or elongase sequences. These chimeric genes could then be introduced into appropriate microorganisms via transformation to provide high-level expression of the encoded enzymes.

Accordingly, it is expected that introduction of chimeric genes encoding a PUFA biosynthetic pathway (e.g., the $\Delta 5$ desaturase, $\Delta 6$ desaturase, $\Delta 17$ desaturase and elongase described herein), under the control of the appropriate promoters will result in increased production of $\omega$-3 and/or $\omega$-6 fatty acids. It is contemplated that it will be useful to express various combinations of these PUFA desaturase and elongase genes together in a host microorganism. It will be obvious to one skilled in the art that the particular genes included within a particular expression cassette(s) will depend on the host cell, its ability to synthesize PUFAs using native desaturases and elongases, the availability of substrate and the desired end product(s). For example, it may be desirable for an expression cassette to be constructed comprising genes encoding one or more of the following enzymatic activities: a $\Delta 4$ desaturase, a $\Delta 5$ desaturase, a $\Delta 6$ desaturase, a $\Delta 12$ desaturase, a $\Delta 15$ desaturase, a $\Delta 17$ desaturase, a $\Delta 9$ desaturase and/or an elongase. As such, the present invention encompasses a method of producing PUFAs comprising exposing a fatty acid substrate to the PUFA enzyme(s) described herein, such that the substrate is converted to the desired fatty acid product. Thus, each PUFA gene and corresponding enzyme product described herein (e.g., a wildtype, codon-optimized, synthetic and/or mutant enzyme having appropriate desaturase or elongase activity) can be used directly or indirectly for the production of PUFAs. Direct production of PUFAs occurs wherein the fatty acid substrate is converted directly into the desired fatty acid product without any intermediate steps or pathway intermediates. For example, production of ARA would occur in a host cell which produces or which is provided DLGA, by adding or introducing into said cell an expression cassette that provides $\Delta 5$ desaturase activity.

In contrast, multiple genes encoding the PUFA biosynthetic pathway may be used in combination, such that a series of reactions occur to produce a desired PUFA. For example, expression cassette(s) encoding elongase, Δ5 desaturase, Δ17 desaturase and Δ4 desaturase activity would enable a host cell that naturally produces GLA, to instead produce DHA (such that GLA is converted to DGLA by an elongase; DGLA may then be converted to ARA by a Δ5 desaturase; ARA is then converted to EPA by a Δ17 desaturase, which may in turn be converted to DPA by an elongase; and DPA would be converted to DHA by a Δ4 desaturase). In a preferred embodiment, wherein the host cell is an oleaginous yeast, expression cassettes encoding each of the enzymes necessary for PUFA biosynthesis will need to be introduced into the organism, since naturally produced PUFAs in these organisms are limited to 18:2 fatty acids (i.e., LA), and less commonly, 18:3 fatty acids (i.e., ALA). Alternatively, substrate feeding may be required.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Initiation control regions or promoters which are useful to drive expression of desaturase and/or elongase ORFs in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species. The transcriptional initiation regulatory regions can be obtained, for example, from: 1.) genes in the glycolytic pathway, such as alcohol dehydrogenase, glyceraldehyde-3-phosphate-dehydrogenase (see U.S. Patent Application No. 60/482,263, incorporated herein by reference), phosphoglycerate mutase (see U.S. Patent Application No. 60/482,263, incorporated herein by reference), fructose-bisphosphate aldolase (see U.S. Patent Application No. 60/519,971, incorporated herein by reference), phosphoglucose-isomerase, phosphoglycerate kinase, etc.; or, 2.) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, as demonstrated in the invention herein in *Yarrowia lipolytica*, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of the PUFA biosynthetic pathway enzymes.

Transformation of Microbial Hosts

Once the DNA encoding a desaturase or elongase polypeptide suitable for expression in an oleaginous yeast has been obtained, it is placed in a plasmid vector capable of autonomous replication in a host cell or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other constructs to maintain stable expression and prevent reassortment of elements among constructs. Judicious choice of regulatory regions, selection means and method of propagation of the introduced construct can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology*, 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. Nos. 4,880,741 and 5,071,764 and Chen, D. C. et al. (*Appl Microbiol Biotechnol.* 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β-galactosidase can convert the substrate X-gal [5-bromo-4-chloro-3-indolyl-β-D-galactopyranoside] to a colored product; luciferase can convert luciferin to a light-emitting product); or 2.) its light-producing or modifying characteristics (e.g., the green fluorescent protein of *Aequorea victoria* fluoresces when illuminated with blue light). Alternatively, antibodies may be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Preferred for use herein are resistance to kanamycin, hygromycin and the amino glycoside G418, as well as ability to grow on media lacking uracil or leucine.

Following transformation, substrates suitable for the recombinantly expressed desaturases and/or elongases (and optionally other PUFA enzymes that are expressed within the host cell) may be produced by the host either naturally or transgenically, or they may be provided exogenously.

Metabolic Engineering of ω-3 and/or ω-6 Fatty Acid Biosynthesis in Microbes

Methods for manipulating biochemical pathways are well known to those skilled in the art; and, it is expected that numerous manipulations will be possible to maximize ω-3 and/or ω-6 fatty acid biosynthesis in oleaginous yeasts, and particularly, in *Yarrowia lipolytica*. This may require metabolic engineering directly within the PUFA biosynthetic pathway or additional manipulation of pathways that contribute carbon to the PUFA biosynthetic pathway.

In the case of manipulations within the PUFA biosynthetic pathway, it may be desirable to increase the production of LA to enable increased production of ω-6 and/or ω-3 fatty acids. This may be accomplished by introducing and/or amplifying genes encoding Δ9 and/or Δ12 desaturases.

To maximize production of ω-6 unsaturated fatty acids, such as ARA, it is well known to one skilled in the art that production is favored in a host microorganism that is substantially free of ALA. Thus, preferably, the host is selected or obtained by removing or inhibiting Δ15 or ω-3 type desaturase activity that permits conversion of LA to ALA. The endogenous desaturase activity can be reduced or eliminated by, for example: 1.) providing a cassette for transcription of antisense sequences to the Δ15 desaturase transcription product; 2.) disrupting the Δ15 desaturase gene through insertion, substitution and/or deletion of all or part of the target gene; or 3.) using a host cell which naturally has [or has been mutated to have] low or no Δ15 desaturase activity. Inhibition of undesired desaturase pathways can also be accomplished through the use of specific desaturase inhibitors such as those described in U.S. Pat. No. 4,778,630.

Alternatively, it may be desirable to maximize production of ω-3 fatty acids (and minimize synthesis of ω-6 fatty acids). Thus, one could utilize a host microorganism wherein the Δ12 desaturase activity that permits conversion of oleic acid to LA is removed or inhibited, using any of the means described above (see also, for example, co-pending U.S. Provisional Application No. 60/484,209, herein incorporated entirely by reference). Subsequently, appropriate expression cassettes would be introduced into the host, along with appropriate substrates (e.g., ALA) for conversion to ω-3 fatty acid derivatives of ALA (e.g., STA, ETA, EPA, DPA, DHA).

Beyond the immediate PUFA biosynthetic pathway, it is expected that manipulation of several other enzymatic pathways leading to the biosynthesis of precursor fatty acids may contribute to the overall net biosynthesis of specific PUFAs. Identification and manipulation of these related pathways will be useful in the future.

Techniques to Up-Regulate Desirable Biosynthetic Pathways

Additional copies of desaturase and elongase genes may be introduced into the host to increase the output of ω-3 and/or ω-6 fatty acid biosynthetic pathways. Expression of the desaturase or elongase genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Yet another approach to increase expression of the desaturase or elongase genes, as demonstrated in the instant invention, is to increase the translational efficiency of the encoded mRNAs by replacement of codons in the native gene with those for optimal gene expression in the selected host microorganism.

Techniques to Down-Regulate Undesirable Biosynthetic Pathways

Conversely, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA). For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al. *J. Bacteriol.* 171:4617-4622 (1989); Balbas et al. *Gene* 136:211-213 (1993); Gueldener et al. *Nucleic Acids Res.* 24:2519-2524 (1996); and Smith et al. *Methods Mol. Cell. Biol.* 5:270-277 (1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of anti-sense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frame-shift mutations). Specific methods for creating mutants using radiation or chemical agents are well documented in the art. See, for example: Thomas D. Brock in *Biotechnology: A Textbook of Industrial Microbiology*, $2^{nd}$ ed. (1989) Sinauer Associates: Sunderland, M A; or Deshpande, Mukund V., *Appl. Biochem. Biotechnol.*, 36:227 (1992).

Another non-specific method of gene disruption is the use of transposable elements or transposons. Transposons are genetic elements that insert randomly into DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available [see, for example: 1.) The Primer Island Transposition Kit, available from Perkin Elmer Applied Biosystems, Branchburg, N.J., based upon the yeast Ty1 element; 2.) The Genome Priming System, available from New England Biolabs, Beverly, Mass., based upon the bacterial transposon Tn7; and 3.) the EZ::TN Transposon Insertion Systems, available from Epicentre Technologies, Madison, Wis., based upon the Tn5 bacterial transposable element].

Within the context of the present invention, it may be useful to modulate the expression of the fatty acid biosynthetic pathway by any one of the methods described above. For example, the present invention provides methods whereby genes encoding key enzymes in the biosynthetic pathways are introduced into oleaginous yeasts for the production of ω-3 and/or ω-6 fatty acids. These genes encode one or more of the following: Δ6 desaturase, Δ5 desaturase, Δ12 desaturase, Δ15 desaturase, Δ4 desaturase, Δ17 desaturase, Δ9 desaturase and PUFA elongase. It will be particularly useful to express these genes in oleaginous yeasts that do not naturally possess ω-3 and/or ω-6 fatty acid biosynthetic pathways and coordinate the expression of these genes, to maximize production of preferred PUFA products using various means for metabolic engineering of the host organism.

Preferred Microbial Hosts for Recombinant Production of ω-3 and/or ω-6 Fatty Acids Host cells for production of omega fatty acids may include microbial hosts that grow on a variety of feedstocks, including simple or complex carbohydrates, organic acids and alcohols, and/or hydrocarbons over a wide range of temperature and pH values.

Preferred microbial hosts, however, are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia*, *Candida*, *Rhodotorula*, *Rhodosporidium*, *Cryptococcus*, *Trichosporon* and *Lipomyces*. More specifically, illustrative oil-synthesizing yeasts include: *Rhodosporidium toruloides*, *Lipomyces starkeyii*, *L. lipoferus*, *Candida revkaufi*, *C. pulcherrima*, *C. tropicalis*, *C. utilis*, *Trichosporon pullans*, *T. cutaneum*, *Rhodotorula glutinus*, *R. graminis*, and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)).

Historically, various strains of *Y. lipolytica* have been used for the manufacture and production of: isocitrate lyase (DD259637); lipases (SU1454852, WO2001083773, DD279267); polyhydroxyalkanoates (WO2001088144); citric acid (RU2096461, RU2090611, DD285372, DD285370, DD275480, DD227448, PL160027); erythritol (EP770683); 2-oxoglutaric acid (DD267999); γ-decalactone (U.S. Pat. No. 6,451,565, FR2734843); γ-dodecalatone (EP578388); and pyruvic acid (JP09252790).

Fermentation Processes for PUFA Production

The transformed microbial host cell is grown under conditions that optimize desaturase and elongase activities and produce the greatest and the most economical yield of the preferred PUFAs. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon source may include one-carbon sources (e.g., carbon dioxide, methanol, formaldehyde, formate and carbon-containing amines) for which metabolic conversion into key biochemical intermediates has been demonstrated. Hence it is contemplated that the source of carbon utilized in the present invention may encompass a wide variety of carbon-containing sources and will only be limited by the choice of the host organism. Although all of the above mentioned carbon sources and mixtures thereof are expected to be suitable in the present invention, preferred carbon sources are sugars and/or fatty acids. Most preferred is glucose and/or fatty acids containing between 10-22 carbons.

Nitrogen may be supplied from an inorganic (e.g., $(NH_4)_2SO_4$) or organic source (e.g., urea or glutamate). In addition to appropriate carbon and nitrogen sources, the fermentation media must also contain suitable minerals, salts, cofactors, buffers, vitamins and other components known to those skilled in the art suitable for the growth of the microorganism and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of oil.

Although cells are typically grown at about 30° C., some studies have shown increased synthesis of unsaturated fatty acids at lower temperatures (Yongmanitchai and Ward, *Appl. Environ. Microbiol.* 57:419-25 (1991)). Based on process economics, this temperature shift should likely occur after the first phase of the two-stage fermentation, when the bulk of the organisms' growth has occurred.

It is contemplated that a variety of fermentation process designs may be applied, where commercial production of omega fatty acids using recombinant expression of desaturase and/or elongase genes is desired. For example, commercial production of PUFAs from a recombinant microbial host may be produced by a batch, fed-batch or continuous fermentation process.

A batch fermentation process is a closed system wherein the media composition is fixed at the beginning of the process and not subject to further additions beyond those required for maintenance of pH and oxygen level during the process. Thus, at the beginning of the culturing process the media is inoculated with the desired organism and growth or metabolic activity is permitted to occur without adding additional sources (i.e., carbon and nitrogen sources) to the medium. In batch processes the metabolite and biomass compositions of the system change constantly up to the time the culture is terminated. In a typical batch process, cells proceed through a static lag phase to a high-growth log phase and finally to a stationary phase, wherein the growth rate is diminished or halted. Left untreated, cells in the stationary phase will eventually die. A variation of the standard batch process is the fed-batch process, wherein the carbon source is continually added to the fermentor over the course of the fermentation process. A fed-batch process is also suitable in the present invention. Fed-batch processes are useful when catabolite repression is apt to inhibit the metabolism of the cells or where it is desirable to have limited amounts of carbon source in the media at any one time. Measurement of the carbon source concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Thomas D. Brock in *Biotechnology: A Textbook of Industrial Microbiology*, $2^{nd}$ ed., (1989) Sinauer Associates Sunderland, Mass.; or Deshpande, Mukund V., *Appl. Biochem. Biotechnol.*, 36:227 (1992), herein incorporated by reference.

Commercial production of omega fatty acids using recombinant expression of desaturase and/or elongase genes may also be accomplished by a continuous fermentation process wherein a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

Purification of PUFAs

The PUFAs may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-491 (1992)). A brief review of downstream processing is also available by A. Singh and O. Ward (*Adv. Appl. Microbiol.* 45:271-312 (1997)).

In general, means for the purification of PUFAs may include extraction with organic solvents, sonication, supercritical fluid extraction (e.g., using carbon dioxide), saponification and physical means such as presses, or combinations thereof. Of particular interest is extraction with methanol and chloroform in the presence of water (E. G. Bligh & W. J. Dyer, *Can. J. Biochem. Physiol.* 37:911-917 (1959)). Where desirable, the aqueous layer can be acidified to protonate negatively-charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high-speed centrifugation or distillation, or combinations of these techniques. Protection of reactive groups, such as the acid or alkenyl groups, may be done at any step through known techniques (e.g., alkylation, iodination). Methods used include methylation of the fatty acids to produce methyl esters. Similarly, protecting groups may be removed at any step. Desirably, purification of fractions containing GLA, STA, ARA, DHA and EPA may be accomplished by treatment with urea and/or fractional distillation.

DESCRIPTION OF PREFERRED EMBODIMENTS

The present invention demonstrates the feasibility of introducing an ω-3 and/or ω-6 biosynthetic pathway into oleaginous yeast for the production of PUFAs. Toward this end, ARA (representative of ω-6 fatty acids) and EPA (representative of ω-3 fatty acids) were selected as desirable products to produce in the oleaginous yeast, *Yarrowia lipolytica*. Thus, the synthesis of ARA required the introduction of genes encoding Δ6 desaturase, elongase and Δ5 desaturase activities into *Yarrowia*, whereas the synthesis of EPA required the introduction of genes encoding Δ6 desaturase, elongase, Δ5 desaturase and Δ17 desaturase activities into *Yarrowia*.

A variety of publicly available Δ5 desaturases from different organisms having the ability to convert DGLA to ARA and ETA to EPA were expressed in *Yarrowia lipolytica* and screened for activity, in order to identify the gene demonstrating the highest level of activity in the alternate host. On this basis, a *Mortierella alpina* Δ5 desaturase (SEQ ID NO:4) was selected as the preferred gene for expression in oleaginous yeast, based on its ability to convert ~30% of intracellular DGLA to ARA in a substrate feeding trial.

Additional substrate feeding trials were conducted to verify the enzymatic activities encoded by the following genes:

A *M. alpina* Δ6 desaturase (SEQ ID NO:2) converts LA to GLA and ALA to STA (wherein the percent substrate conversion of LA to GLA in *Y. lipolytica* was ~30%);

A *Saprolegnia diclina* Δ17 desaturase (SEQ ID NO:6) converts DGLA to ETA and ARA to EPA (wherein the percent substrate conversion of ARA to EPA in *Y. lipolytica* was ~23%); and A *M. alpina* high affinity PUFA elongase (SEQ ID NO:8) converts GLA to DGLA, STA to ETA and EPA to DPA (wherein the percent substrate conversion of GLA to DGLA in *Y. lipolytica* was ~30%).

Based on the lower percent substrate conversion of the *S. diclina* Δ17 desaturase (relative to the Δ6 and Δ5 desaturase and the elongase), this particular gene was codon-optimized to enhance its expression in *Yarrowia*. This was accomplished by determining the codon usage and signature of structural genes in *Yarrowia lipolytica*, designing a codon-optimized Δ17 desaturase gene, and then synthesizing the gene in vitro to enable its increased efficiency in the alternate host (with respect to the wildtype gene).

To enable synthesis of ARA or EPA (and thereby demonstrate proof-of-concept for the ability of oleaginous hosts to be engineered for production of ω-6 and ω-3 fatty acids (i.e., ARA and EPA)), two different DNA expression constructs were subsequently prepared: 1.) the first contained the Δ6 desaturase, Δ5 desaturase and high-affinity PUFA elongase; and 2.) the second contained the Δ6 desaturase, Δ5 desaturase, high-affinity PUFA elongase and codon-optimized Δ17 desaturase. Both constructs were separately transformed into *Yarrowia lipolytica* and integrated into the chromosomal URA3 gene encoding the enzyme orotidine-5'-phosphate decarboxylase (EC 4.1.1.23). GC analysis of the host cells fed with appropriate substrates detected production of ARA (Example 5) and EPA (Example 6), respectively. Thus, this is the first demonstration of PUFA biosynthesis in an oleaginous yeast whereby the ω-3 and/or ω-6 biosynthetic pathways have been introduced into an oleaginous yeast.

On the basis of the teachings and results described herein, it is expected that one skilled in the art will recognize the feasability and commercial utility created by using oleaginous yeast as a production platform for the synthesis of a variety of ω-3 and/or ω-6 PUFAs.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, *Experiments with Gene Fusions*; Cold Spring Harbor Laboratory: Cold Spring Harbor, N.Y. (1984); and 3.) Ausubel, F. M. et al., *Current Protocols in Molecular Biology*, published by Greene Publishing Assoc. and Wiley-Interscience (1987).

Materials and Methods suitable for the maintenance and growth of microbial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, 2$^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

*E. coli* (XL1-Blue) competent cells were purchased from the Stratagene Company (San Diego, Calif.). *E. coli* strains were typically grown at 37° C. on Luria Bertani (LB) plates.

General molecular cloning was performed according to standard methods (Sambrook et al., supra). Oligonucleotides were synthesized by Sigma-Genosys (Spring, Tex.). Site-directed mutagenesis was performed using Stratagene's QuickChange™ Site-Directed Mutagenesis kit, per the manufacturers' instructions. When polymerase chain reaction (PCR) or site-directed mutagenesis was involved in sub-cloning, the constructs were sequenced to confirm that no errors had been introduced to the sequence. PCR products were cloned into Promega's pGEM-T-easy vector (Madison, Wis.).

DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNA Star, Inc.). Alternatively, manipulations of genetic sequences were accomplished using the suite of programs available from the Genetics Computer Group Inc. (Wisconsin Package Version 9.0, Genetics Computer Group (GCG), Madison, Wis.). The GCG program "Pileup" was used with the gap creation default value of 12, and the gap extension default value of 4. The GCG "Gap" or "Bestfit" programs were used with the default gap creation penalty of 50 and the default gap extension penalty of 3. Unless otherwise stated, in all other cases GCG program default parameters were used.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s), and "kB" means kilobase(s).

Cultivation of *Yarrowia lipolytica*

*Yarrowia lipolytica* strains ATCC #76982 and ATCC #90812 were purchased from the American Type Culture Collection (Rockville, Md.). *Y. lipolytica* strains were usually grown at 28° C. on YPD agar (1% yeast extract, 2% bactopeptone, 2% glucose, 2% agar). For selection of transformants, minimal medium (0.17% yeast nitrogen base (DIFCO Laboratories, Detroit, Mich.) without ammonium sulfate or amino acids, 2% glucose, 0.1% proline, pH 6.1) was used. Supplements of adenine, leucine, lysine and/or uracil were added as appropriate to a final concentration of 0.01%.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G., and Nishida I. *Arch Biochem Biophys.* 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

Example 1

Construction of Plasmids Suitable for Heterologous Gene Expression in *Yarrowia lipolytica*

The plasmid pY5, a derivative of pINA532 (a gift from Dr. Claude Gaillardin, Insitut National Agronomics, Centre de biotechnologie Agro-Industrielle, laboratoire de Genetique Moleculaire et Cellularie INRA-CNRS, F-78850 Thiverval-Grignon, France), was constructed for expression of heterologous genes in *Yarrowia lipolytica*, as diagrammed in FIG. 3.

First, the partially-digested 3598 bp EcoRI fragment containing the ARS18 sequence and LEU2 gene of pINA532 was subcloned into the EcoRI site of pBluescript (Strategene, San Diego, Calif.) to generate pY2. The TEF promoter (Muller S., et al. *Yeast*, 14: 1267-1283 (1998)) was amplified from *Yarrowia lipolytica* genomic DNA by PCR using TEF5' (SEQ ID NO:38) and TEF3' (SEQ ID NO:39) as primers. PCR amplification was carried out in a 50 μl total volume containing: 100 ng *Yarrowia* genomic DNA, PCR buffer containing 10 mM KCl, 10 mM (NH$_4$)$_2$SO$_4$, 20 mM Tris-HCl (pH 8.75), 2 mM MgSO$_4$, 0.1% Triton X-100, 100 μg/mL BSA (final concentration), 200 μM each deoxyribonucleotide triphosphate, 10 pmole of each primer and 1 μl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C. The 418 bp PCR product was ligated into pCR-Blunt to generate pIP-tef. The BamHI/EcoRV fragment of pIP-tef was subcloned into the BamHI/SmaI sites of pY2 to generate pY4.

The XPR2 transcriptional terminator was amplified by PCR using pINA532 as template and XPR5' (SEQ ID NO:40) and XPR3' (SEQ ID NO:41) as primers. The PCR amplification was carried out in a 50 μl total volume, using the components and conditions described above. The 179 bp PCR product was digested with SacII and then ligated into the SacII site of pY4 to generate pY5. Thus, pY5 (shown in FIGS. 3 and 4) is useful as a *Yarrowia-E. coli* shuttle plasmid containing:

1.) a *Yarrowia* autonomous replication sequence (ARS18);
2.) a ColE1 plasmid origin of replication;
3.) an ampicillin-resistance gene (AmpR), for selection in *E. coli;*
4.) a *Yarrowia* LEU2 gene (E.G. 4.2.1.33, encoding isopropylmalate isomerase), for selection in *Yarrowia;*
5.) the translation elongation promoter (TEF P), for expression of heterologous genes in *Yarrowia;* and 6.) the extracellular protease gene terminator (XPR2) for transcriptional termination of heterologous gene expression in *Yarrowia*.

pY5-13 (FIG. 4) was constructed as a derivative of pY5 to facilitate subcloning and heterologous gene expression in *Yarrowia lipolytica*. Specifically, pY5-13 was constructed by 6 rounds of site-directed mutagenesis using pY5 as template. Both SalI and ClaI sites were eliminated from pY5 by site-directed mutagenesis using oligonucleotides YL5 and YL6 (SEQ ID NOs:106 and 107) to generate pY5-5. A SalI site was introduced into pY5-5 between the Leu2 gene and the TEF promoter by site-directed mutagenesis using oligouncleotides YL9 and YL10 (SEQ ID NOs:110 and 111) to generate pY5-6. A PacI site was introduced into pY5-6 between the LEU2 gene and ARS18 using oligouncleotides YL7 and YL8 (SEQ ID NOs:108 and 109) to generate pY5-8. A NcoI site was introduced into pY5-8 around the translation start codon of the TEF promoter using oligonucleotides YL3 and YL4 (SEQ ID NOs:104 and 105) to generate pY5-9. The NcoI site inside the Leu2 gene of pY5-9 was eliminated using YL1 and YL2 oligonucleotides (SEQ ID NOs:102 and 103) to generate pY5-12. Finally, a BsiWI site was introduced into pY5-12 between the ColE1 and XPR2 region using oligouncleotides YL61 and YL62 (SEQ ID NOs:88 and 89) to generate pY5-13.

A second derivative of plasmid pY5 was constructed to facilitate subcloning. Specifically, pY5-4 (FIG. 4) was constructed by three rounds of site-directed mutagenesis using pY5 as template. A NcoI site located inside the Leu2 reporter gene was eliminated from pY5 using oligonucleotides YL1 and YL2 (SEQ ID NOs:102 and 103) to generate pY5-1. A NcoI site was introduced into pY5-1 between the TEF promoter and XPR2 transcriptional terminator by site-directed mutagenesis using oligonucleotides YL3 and YL4 (SEQ ID NOs:104 and 105) to generate pY5-2. A PacI site was then introduced into pY5-2 between the TEF promoter and XPR2 transcriptional terminator using oligonucleotides YL23 and YL24 (SEQ ID NOs:112 and 113) to generate pY5-4.

Example 2

Selection of Δ6 Desaturase, Δ5 Desaturase, Δ17 Desaturase and High Affinity PUFA Elongase Genes for Expression in *Yarrowia lipolytica*

Prior to the introduction of specific genes encoding an ω-3 and/or ω-6 biosynthetic pathway into oleaginous yeast, it was necessary to confirm the functionality of heterologous Δ6 desaturase, elongase, Δ5 desaturase and Δ17 desaturase genes expressed in *Yarrowia*. This was accomplished by measuring the conversion efficiency encoded by each wildtype gene in the alternate host. Specifically, four Δ5 desaturases, a *Mortierella alpina* Δ6 desaturase, a *Saprolegnia diclina* Δ17 desaturase and a *M. alpina* high affinity PUFA elongase were separately expressed and screened for activity in substrate-feeding trials. Based on these results, a *M. alpina* Δ5 desaturase gene was selected for use in conjunction with the Δ6 and Δ17 desaturase and high affinity PUFA elongase genes.

Construction of Expression Plasmids

In general, wildtype desaturase or elongase genes were either isolated by restriction digestion or amplified by PCR and inserted into appropriate vectors for expression. Each PCR amplification was carried out in a 50 µl total volume, comprising PCR buffer containing: 10 ng template, 10 mM KCl, 10 mM $(NH_4)_2SO_4$, 20 mM Tris-HCl (pH 8.75), 2 mM $MgSO_4$, 0.1% Triton X-100, 100 µg/mL BSA (final concentration), 200 µM each deoxyribonucleotide triphosphate, 10 pmole of each primer and 1 µl of PfuTurbo DNA polymerase (Stratagene, San Diego, Calif.). Amplification was carried out as follows (unless otherwise specified): initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C.

Wild Type *Mortierella alpina* (Accession #AF465281) Δ6 Desaturase

The 1384 bp NcoI/NotI fragment of pCGR5 (U.S. Pat. No. 5,968,809), which contains the *M. alpina* Δ6 desaturase gene (SEQ ID NO:1), was inserted into the NcoI/NotI sites of pY5-2 (Example 1) to generate pY54.

Wild Type *Mortierella alpina* (Accession #AF067654) Δ5 Desaturase

Figure 5A:
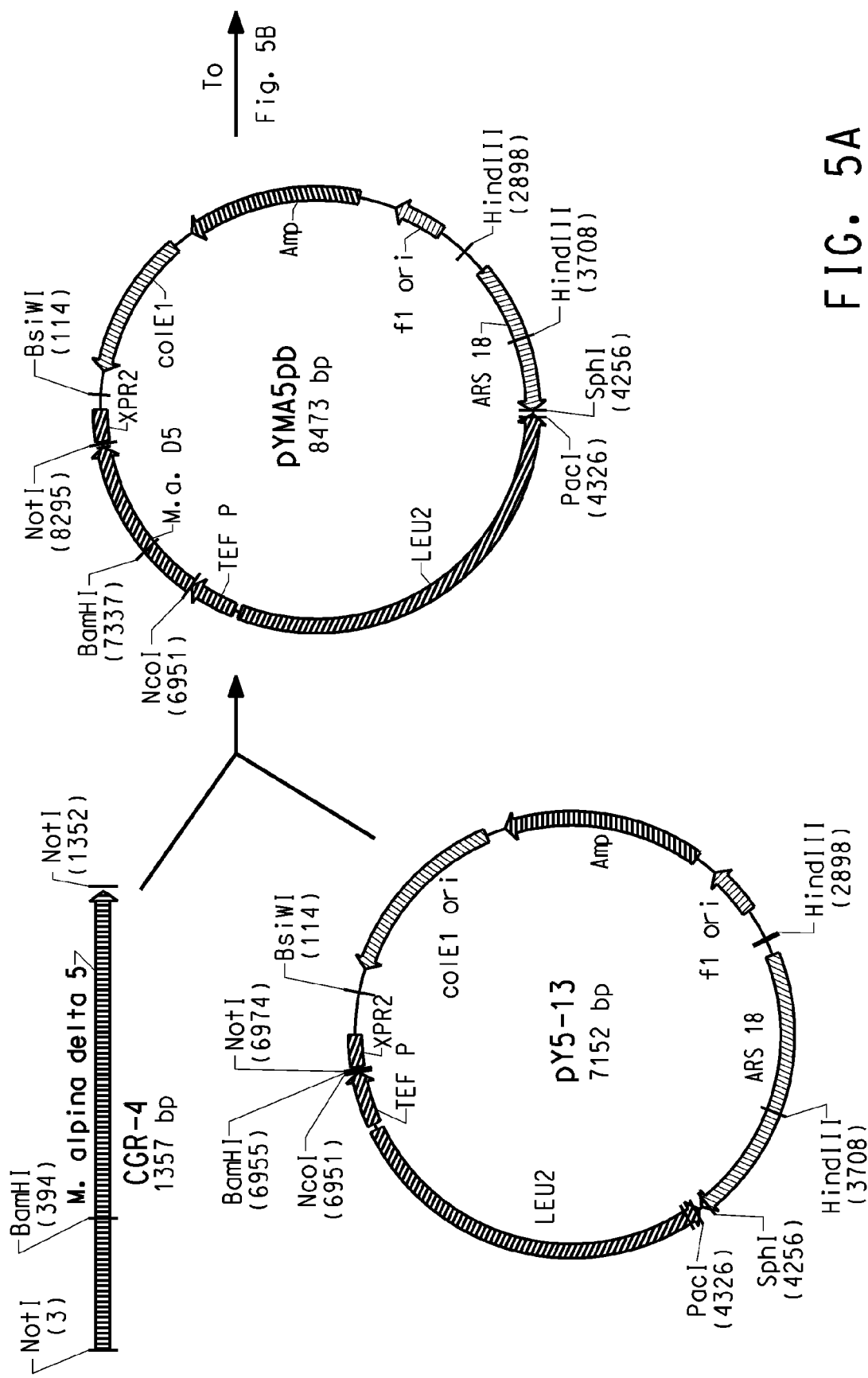
FIG. 5 is a schematic presentation of the construction of intermediate vector pYZM5CHPPA.
Figure 5B:
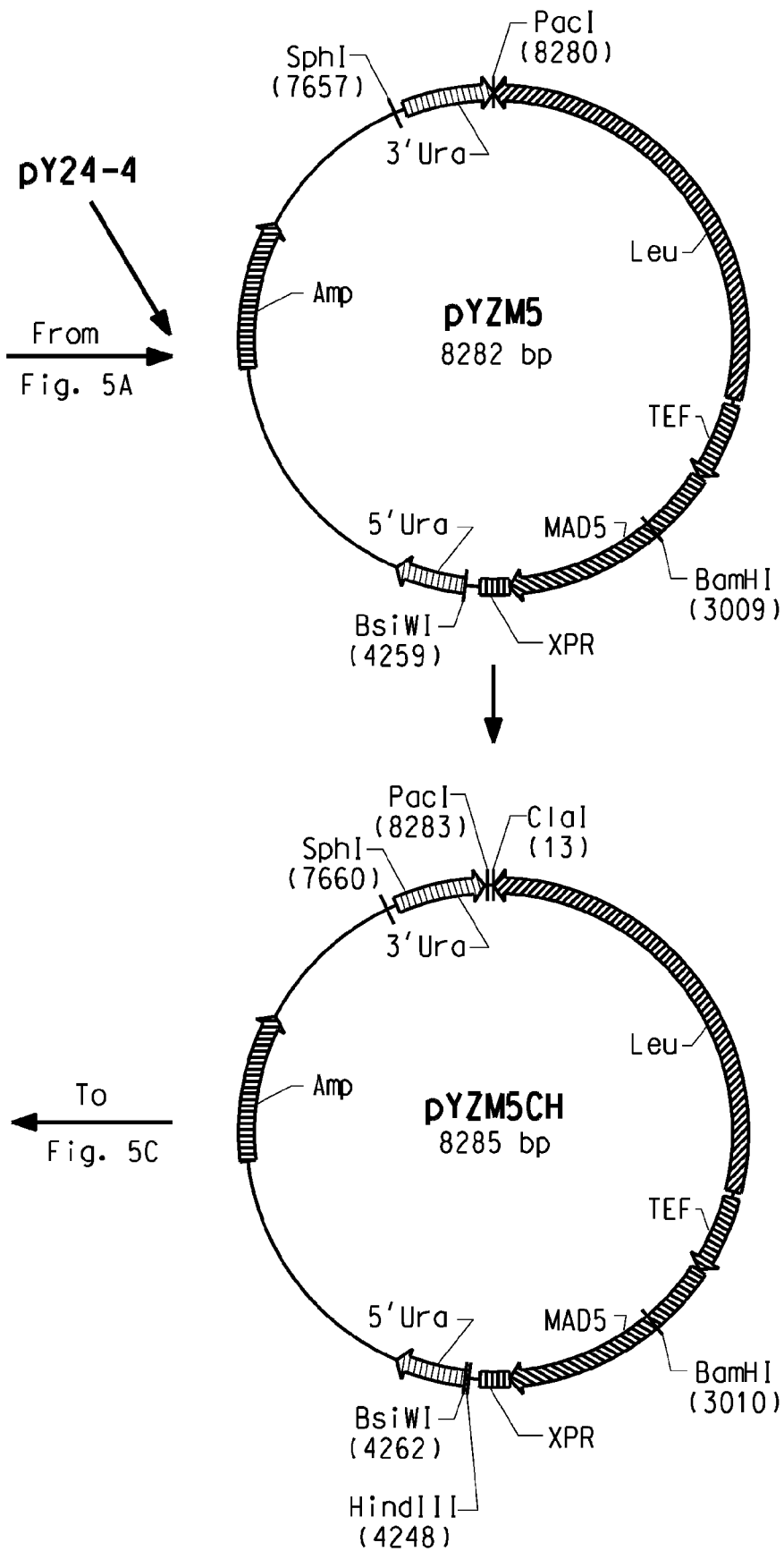
Figure 5C:
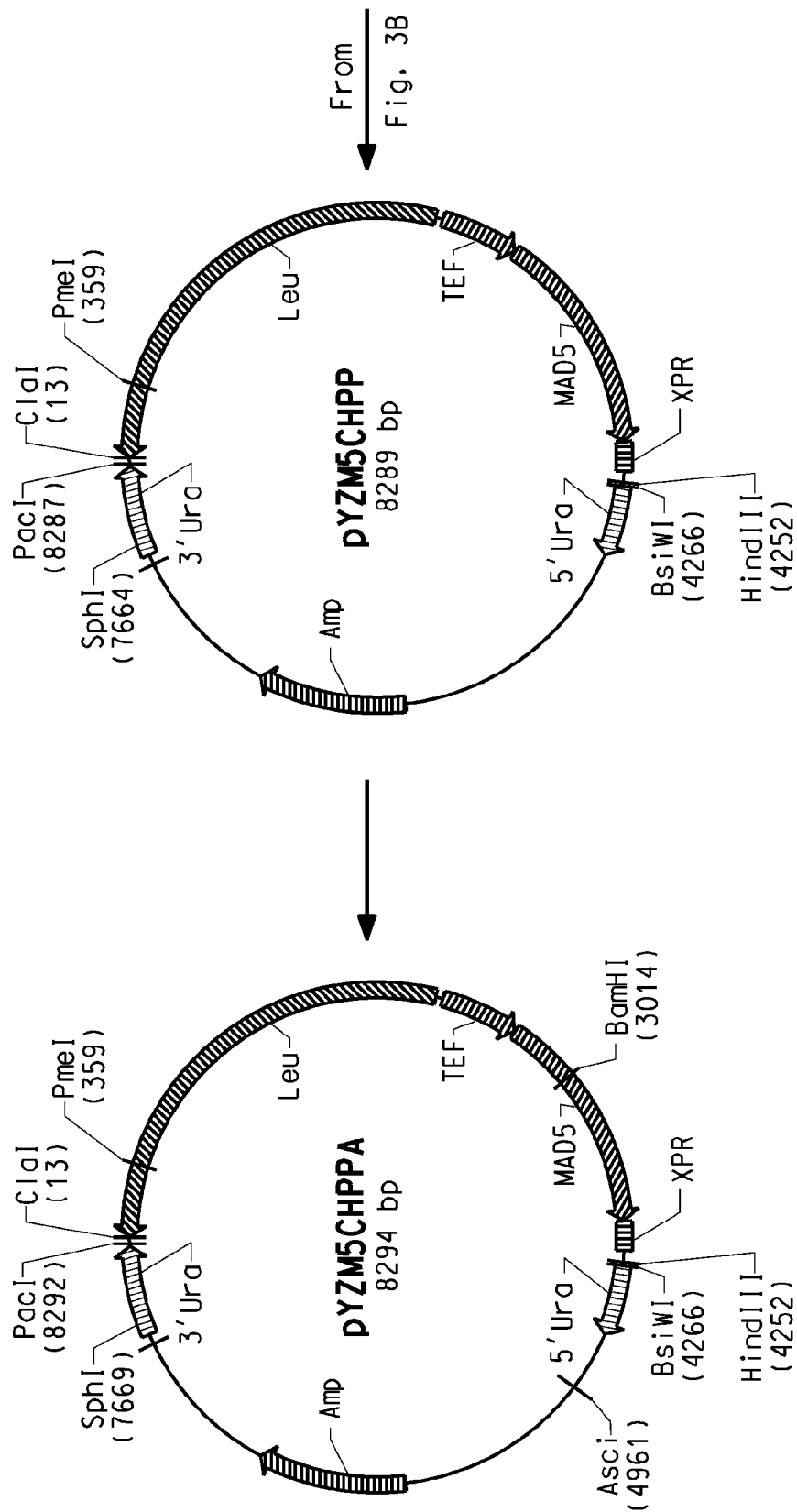

The *M. alpina* Δ5 desaturase gene (SEQ ID NO:3) was amplified by PCR using oligonucleotides YL11 and YL12 (SEQ ID NOs:72 and 73) as primers and plasmid pCGR-4 (U.S. Pat. No. 6,075,183) as template. PCR amplification was carried out as described above, with the exception that the elongation step was extended to 1.5 min (for cycles 1-35). The 1357 bp PCR product was digested with NcoI/NotI and ligated to NcoI/NotI-digested pY5-13 (described in Example 1) to generate pYMA5pb (FIG. 5).

Wild Type *Saprolegnia diclina* (ATCC #56851) Δ5 Desaturase

The *S. diclina* Δ5 desaturase gene (SEQ ID NO:114) was amplified by PCR using oligonucleotides YL13A and YL14 (SEQ ID NOs:116 and 117) as primers and plasmid pRSP3 (WO 02/081668) as template. PCR amplification was carried out as described above, with the exception that the elongation step was extended to 1.5 min (for cycles 1-35). The 1.4 kB PCR product was digested with NcoI/PacI and ligated to NcoI/PacI-digested pY5-4 (FIG. 4; described in Example 1) to generate pYSD5.

Wild Type *Isochrysis galbana* CCMP1323 Δ5 Desaturase

The *I. galbana* Δ5-desaturase gene (SEQ ID NO:118) was amplified by PCR using oligonucleotides YL19A and YL20 (SEQ ID NOs:120 and 121) as primers and plasmid pRIG-1 (WO 02/081668 A2) as template. PCR amplification was carried out as described above, with the exception that the elongation step was extended to 1.5 min (for cycles 1-35). The 1.4 kB PCR product was digested with BamHI/PacII and ligated to BamHI/PacII-digested pY5-4 (described in Example 1) to generate pYIG5.

Wild Type *Thraustochytrium aureum* (ATCC #34304) Δ5 Desaturase

The *T. aureum* Δ5-desaturase gene (SEQ ID NO:122) was amplified by PCR using oligonucleotides YL15 and YL16B (SEQ ID NOs:124 and 125) as primers and plasmid pRTA4 (WO 02/081668 A2) as template. PCR amplification was carried out as described above, with the exception that the elongation step was extended to 1.5 min (for cycles 1-35). The 1.4 kB PCR product was digested with NcoI/NotI and ligated to NcoI/NotI-digested pY5-2 (described in Example 1) to generate pYTA5.

Wild Type *Saprolegnia diclina* (ATCC #56851) Δ17 Desaturase

The wild type Δ17 desaturase gene of *S. diclina* was amplified from plasmid pRSP19 (US 2003/0196217 A1) by PCR using oligonucleotides YL21A (SEQ ID NO:42) and YL22 (SEQ ID NO:43) as primers. The PCR products were digested with NcoI/PacI and then ligated to NcoI/PacI-digested pY5-4 (FIG. 4; described in Example 1) to generate pYSD17.

Wild Type *Mortierella alpina* (Accession #AX464731) High Affinity Elongase

Figure 3A:
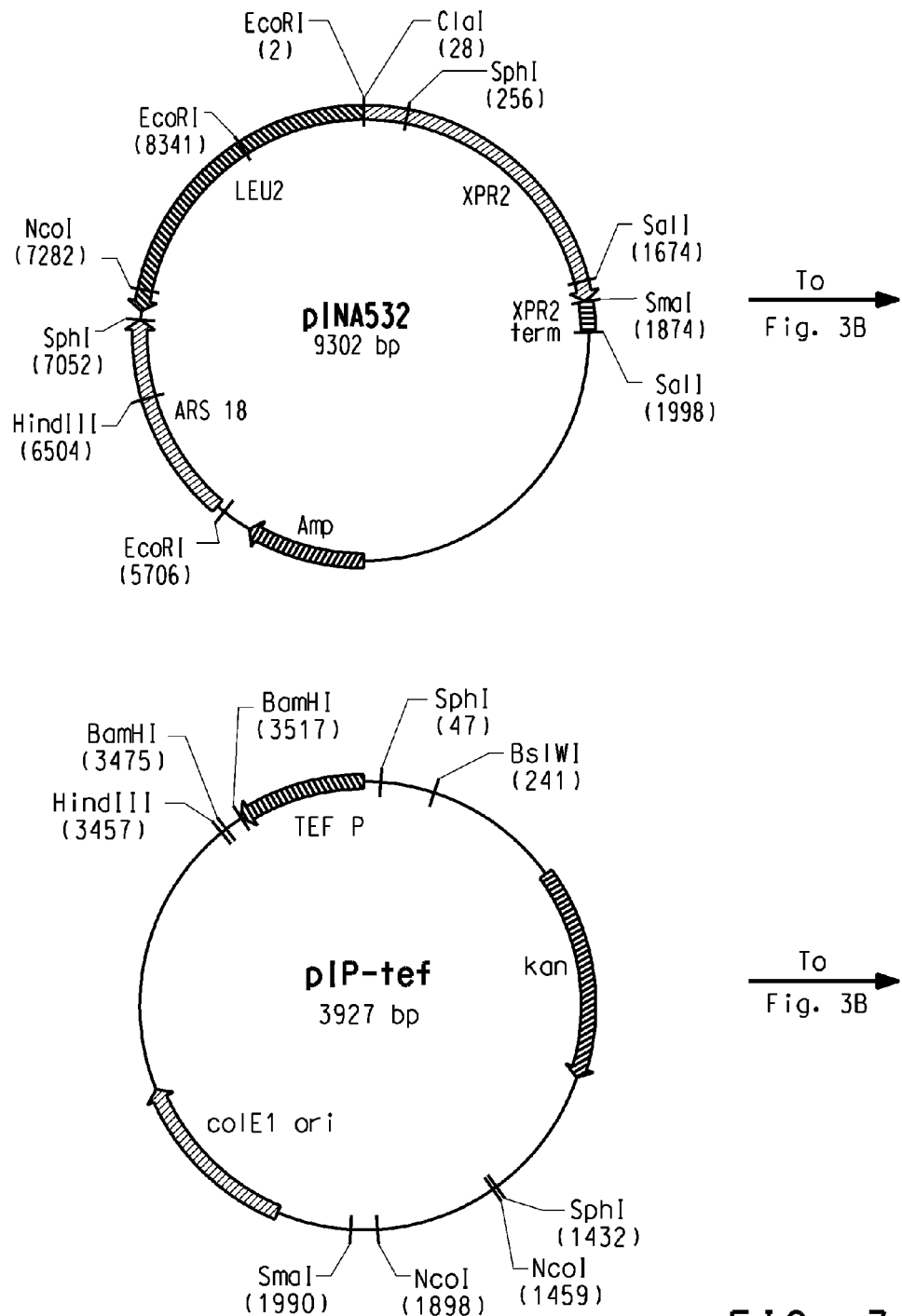
FIG. 3 illustrates the construction of plasmid vector pY5 for gene expression in *Yarrowia lipolytica*.
Figure 3C:
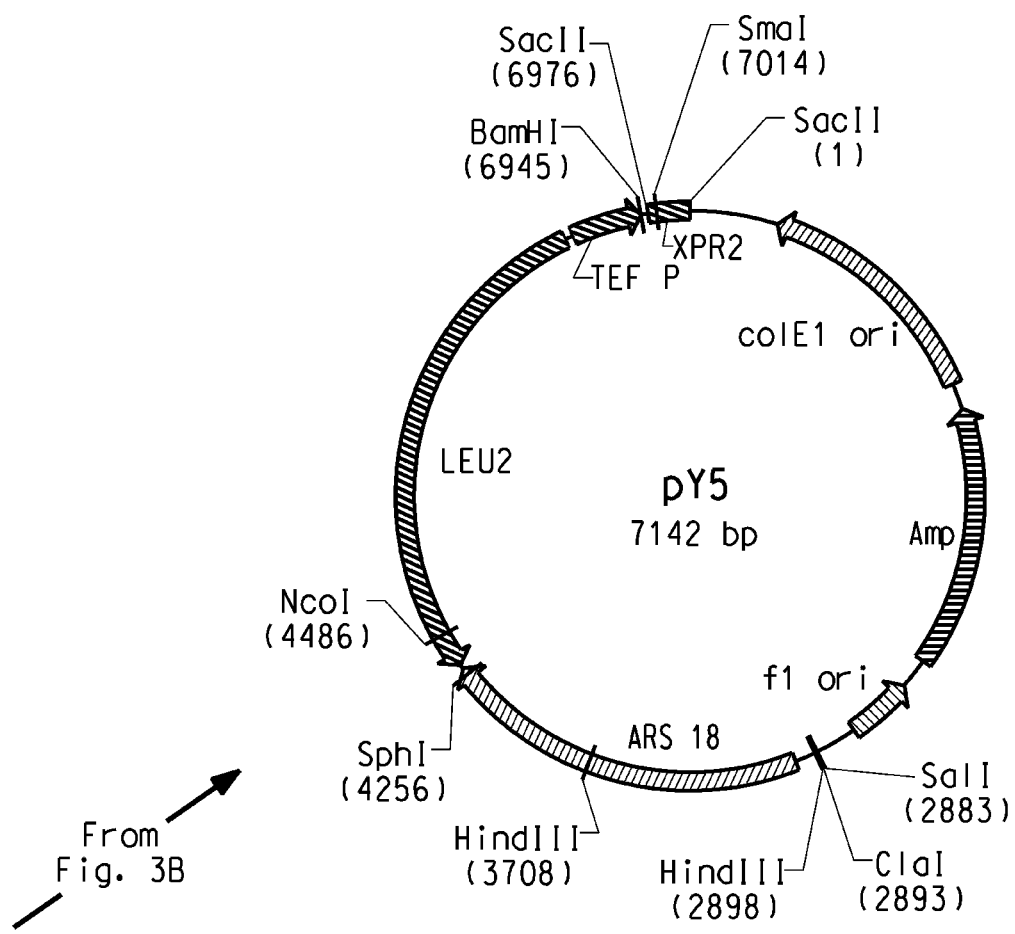
Figure 4:
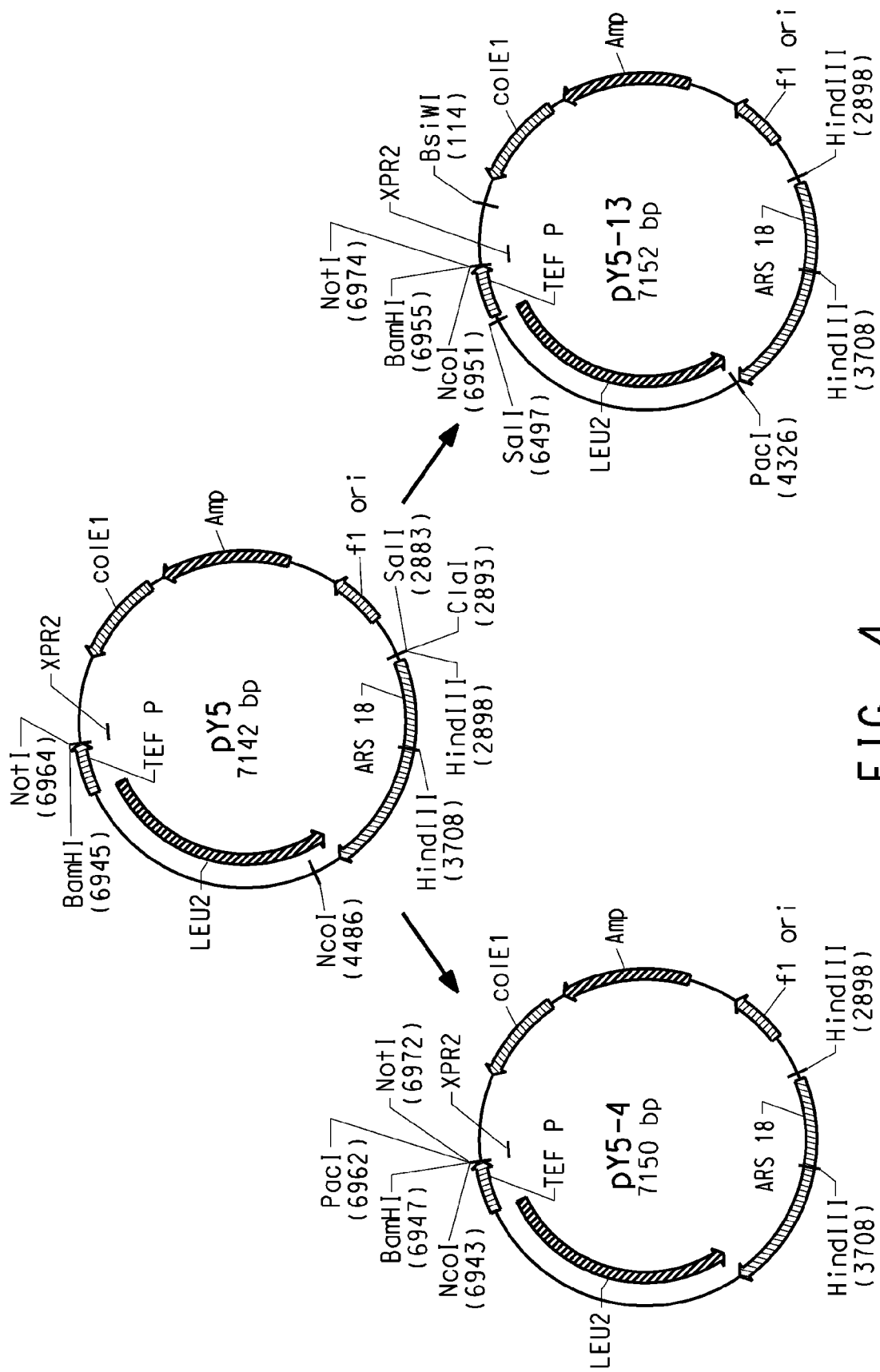
FIG. 4 illustrates the construction of plasmid vectors pY5-4 and pY5-13 for gene expression in *Y. lipolytica*.

The 973 bp NotI fragment of pRPB2 (WO 00/12720), containing the coding region of a *M. alpina* high affinity PUFA elongase gene (SEQ ID NO:7), was inserted into the NotI site of pY5 (described in Example 1; FIGS. 3 and 4) to generate pY58.

Transformation of *Yarrowia lipolytica*

The plasmids pY54, pYMA5pb, pYSD5, pYIG5, pYTA5, pYSD17 and pY58 were transformed separately into *Y. lipolytica* ATCC #76982 according to the method of Chen, D. C. et al. (*Appl Microbiol Biotechnol.* 48(2):232-235-(1997)).

Briefly, a leucine auxotroph of *Yarrowia* was streaked onto a YPD plate and grown at 30° C. for approximately 18 hr. Several large loopfuls of cells were scraped from the plate and resuspended in 1 mL of transformation buffer containing:

2.25 mL of 50% PEG, average MW 3350;
0.125 mL of 2 M Li acetate, pH 6.0;
0.125 mL of 2M DTT; and
50 µg sheared salmon sperm DNA.

About 500 ng of plasmid DNA were incubated in 100 µl of resuspended cells, and maintained at 39° C. for 1 hr with vortex mixing at 15 min intervals. The cells were plated onto minimal media plates lacking leucine and maintained at 30° C. for 2 to 3 days.

Determination of Percent Substrate Conversion

Single colonies of transformant *Y. lipolytica* containing pY54, pYMA5pb, pYSD5, pYIG5, pYTA5, pYSD17 or pY58 were each grown in 3 mL minimal media (20 g/L glucose, 1.7 g/L yeast nitrogen base without amino acids, 1 g/L L-proline, 0.1 g/L L-adenine, 0.1 g/L L-lysine, pH 6.1) at 30° C. to an $OD_{600}$~1.0. For substrate feeding, 100 µl of cells were then subcultured in 3 mL minimal media containing 10 µg of substrate for about 24 hr at 30° C. Cells were subsequently collected by centrifugation, the lipids were extracted, and fatty acid methyl esters were prepared by transesterification and subsequently analyzed by GC (as described in the General Methods). Percent substrate conversion was determined as:

[product/(substrate+product)]*100.

Percent Substrate Conversion by *M. alpina* Δ6 Desaturase

The *M. alpina* Δ6 desaturase converts LA to GLA and ALA to STA. *Y. lipolytica* strains containing pY54 were grown as described above (no substrate feeding required) and lipids were analyzed. The results showed that *Yarrowia* strains with pY54 converted about 30% LA to GLA.

Percent Substrate Conversion by *M. alpina, S. diclina, I. galbana* and *T. aureum* Δ5 Desaturases The Δ5 desaturases from *M. alpina, S. diclina, I. galbana* and *T. aureum* each convert DGLA to ARA and ETA to EPA. *Y. lipolytica* strains containing pYMA5pb, pYSD5, pYIG5 or pYTA5 were grown separately from single colonies, subcultured in minimal media containing 10 µg of DGLA, and then subjected to lipid analysis as described above. *Yarrowia* strains with pYMA5pb (*M. alpina*) converted about 30% of intracellular DGLA to ARA; the *Yarrowia* strains with pYSD5 (*S. diclina*) converted about 12%; the *Yarrowia* strains with pYIG5 (*I. galbana*) converted about 7%; and the *Yarrowia* strains with pYTA5 (*T. aureum*) converted about 23% of intracellular DGLA to ARA.

Percent Substrate Conversion by *S. diclina* Δ17 Desaturase

The *S. diclina* Δ17 desaturase converts ARA to EPA and DGLA to ETA. *Y. lipolytica* strains containing pYSD17 were grown from single colonies, subcultured in minimal media containing 10 µg of ARA, and subjected to lipid analysis as described above. The results of the ARA feeding experiments showed that *Yarrowia* strains with pYSD17 converted about 23% of intracellular ARA to EPA.

Percent Substrate Conversion of Wild Type *M. alpina* High Affinity Elongase

The *M. alpina* high affinity PUFA elongase converts GLA to DGLA, STA to ETA and EPA to DPA. *Y. lipolytica* strains containing pY58 were grown from single colonies, subcultured in minimal media containing 10 µg of GLA, and subjected to lipid analysis as described above. The results of the GLA feeding experiments showed that *Yarrowia* strains with pY58 converted about 30% of intracellular GLA to DGLA.

Example 3

Synthesis and Expression of a Codon-Optimized Δ17 Desaturase Gene in *Yarrowia lipolytica*

Based on the results of Example 2, genes encoding Δ6 desaturase, elongase and Δ5 desaturase activities were available that each enabled ~30% substrate conversion in *Yarrowia lipolytica*. The Δ17 desaturase from *S. diclina*, however, had a maximum percent substrate conversion of only 23%. Thus, a codon-optimized Δ17 desaturase gene was designed, based on the *Saprolegnia diclina* DNA sequence (SEQ ID NO:5), according to the *Yarrowia* codon usage pattern, the consensus sequence around the ATG translation initiation codon and the general rules of RNA stability (Guhaniyogi, G. and J. Brewer, *Gene* 265(1-2):11-23 (2001)).

Figure 6A:
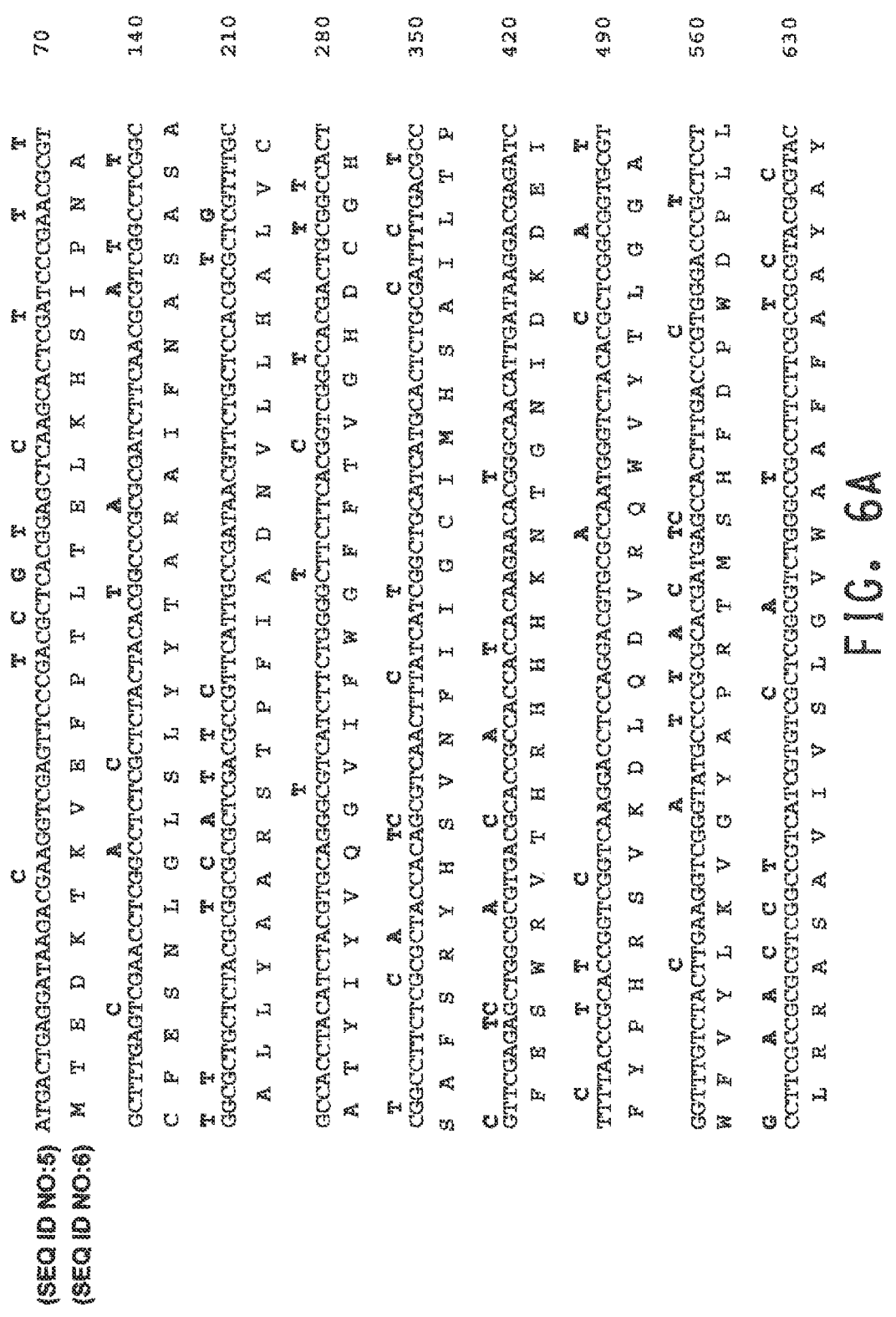

In addition to modification to the translation initiation site, 127 bp of the 1077 bp coding region (comprising 117 codons) were codon-optimized. A comparison between this codon-optimized DNA sequence (SEQ ID NO:9) and the *S. diclina* Δ17 desaturase gene DNA sequence (SEQ ID NO:5) is shown in FIG. 6, wherein nucleotides in bold text correspond to nucleotides that were modified in the codon-optimized gene. None of the modifications in the codon-optimized gene changed the amino acid sequence of the encoded protein (SEQ ID NO:6).

Determining the Preferred Codon Usage in *Yarrowia lipolytica*

Approximately 100 genes of *Y. lipolytica* were found in the National Center for Biotechnology Information public database. The coding regions of these genes, comprising 121,167 bp, were translated by the Editseq program of DNAStar to the corresponding 40,389 amino acids and were tabulated to determine the *Y. lipolytica* codon usage profile shown in Table 3. The column titled "No." refers to the number of times a given codon encodes a particular amino acid in the sample of 40,389 amino acids. The column titled "%" refers to the frequency that a given codon encodes a particular amino acid. Entries shown in bold text represent the codons favored in *Yarrowia lipolytica*.

TABLE 3

| Codon Usage In Yarrowia lipolytica | | | |
|---|---|---|---|
| Codon | Amino Acid | No. | % |
| GCA | Ala (A) | 359 | 11.4 |
| GCC | Ala (A) | 1523 | 48.1 |
| GCG | Ala (A) | 256 | 8.1 |
| GCU | Ala (A) | 1023 | 32.3 |
| AGA | Arg (R) | 263 | 13.2 |

TABLE 3-continued

Codon Usage In *Yarrowia lipolytica*

| Codon | Amino Acid | No. | % |
|---|---|---|---|
| AGG | Arg (R) | 91 | 4.6 |
| CGA | Arg (R) | 1133 | 56.8 |
| CGC | Arg (R) | 108 | 5.4 |
| CGG | Arg (R) | 209 | 1.0 |
| CGU | Arg (R) | 189 | 9.5 |
| AAC | Ans (N) | 1336 | 84.0 |
| AAU | Ans (N) | 255 | 16.0 |
| GAC | Asp (D) | 1602 | 66.8 |
| GAU | Asp (D) | 795 | 33.2 |
| UGC | Cys (C) | 268 | 53.2 |
| UGU | Cys (C) | 236 | 46.8 |
| CAA | Gln (Q) | 307 | 17.0 |
| CAG | Gln (Q) | 1490 | 83.0 |
| GAA | Glu (E) | 566 | 23.0 |
| GAG | Glu (E) | 1893 | 77.0 |
| GGA | Gly (G) | 856 | 29.7 |
| GGC | Gly (G) | 986 | 34.2 |
| GGG | Gly (G) | 148 | 5.1 |
| GGU | Gly (G) | 893 | 31.0 |
| CAC | His (H) | 618 | 65.5 |
| CAU | His (H) | 326 | 34.5 |
| AUA | Ile (I) | 42 | 2.1 |
| AUC | Ile (I) | 1106 | 53.7 |
| AUU | Ile (I) | 910 | 44.2 |
| CUA | Leu (L) | 166 | 4.7 |
| CUC | Leu (L) | 1029 | 29.1 |
| CUG | Leu (L) | 1379 | 38.9 |
| CUU | Leu (L) | 591 | 16.7 |
| UUA | Leu (L) | 54 | 1.5 |
| UUG | Leu (L) | 323 | 9.1 |
| AAA | Lys (K) | 344 | 14.8 |
| AAG | Lys (K) | 1987 | 85.2 |
| AUG | Met (M) | 1002 | 100 |
| UUC | Phe (F) | 996 | 61.1 |
| UUU | Phe (F) | 621 | 38.9 |
| CCA | Pro (P) | 207 | 9.6 |
| CCC | Pro (P) | 1125 | 52.0 |
| CCG | Pro (P) | 176 | 8.2 |
| CCU | Pro (P) | 655 | 30.2 |
| AGC | Ser (S) | 335 | 11.3 |
| AGU | Ser (S) | 201 | 6.8 |
| UCA | Ser (S) | 221 | 7.5 |
| UCC | Ser (S) | 930 | 31.5 |
| UCG | Ser (S) | 488 | 16.5 |
| UCU | Ser (S) | 779 | 26.4 |
| UAA | Term | 38 | 46.9 |
| UAG | Term | 30 | 37.0 |
| UGA | Term | 13 | 16.1 |
| ACA | Thr (T) | 306 | 12.7 |
| ACC | Thr (T) | 1245 | 51.6 |
| ACG | Thr (T) | 269 | 11.1 |
| ACU | Thr (T) | 595 | 24.6 |
| UGG | Trp (W) | 488 | 100 |
| UAC | Tyr (Y) | 988 | 83.2 |
| UAU | Tyr (Y) | 200 | 16.8 |
| GUA | Val (V) | 118 | 4.2 |
| GUC | Val (V) | 1052 | 37.3 |
| GUG | Val (V) | 948 | 33.6 |
| GUU | Val (V) | 703 | 24.9 |

Figure 7:
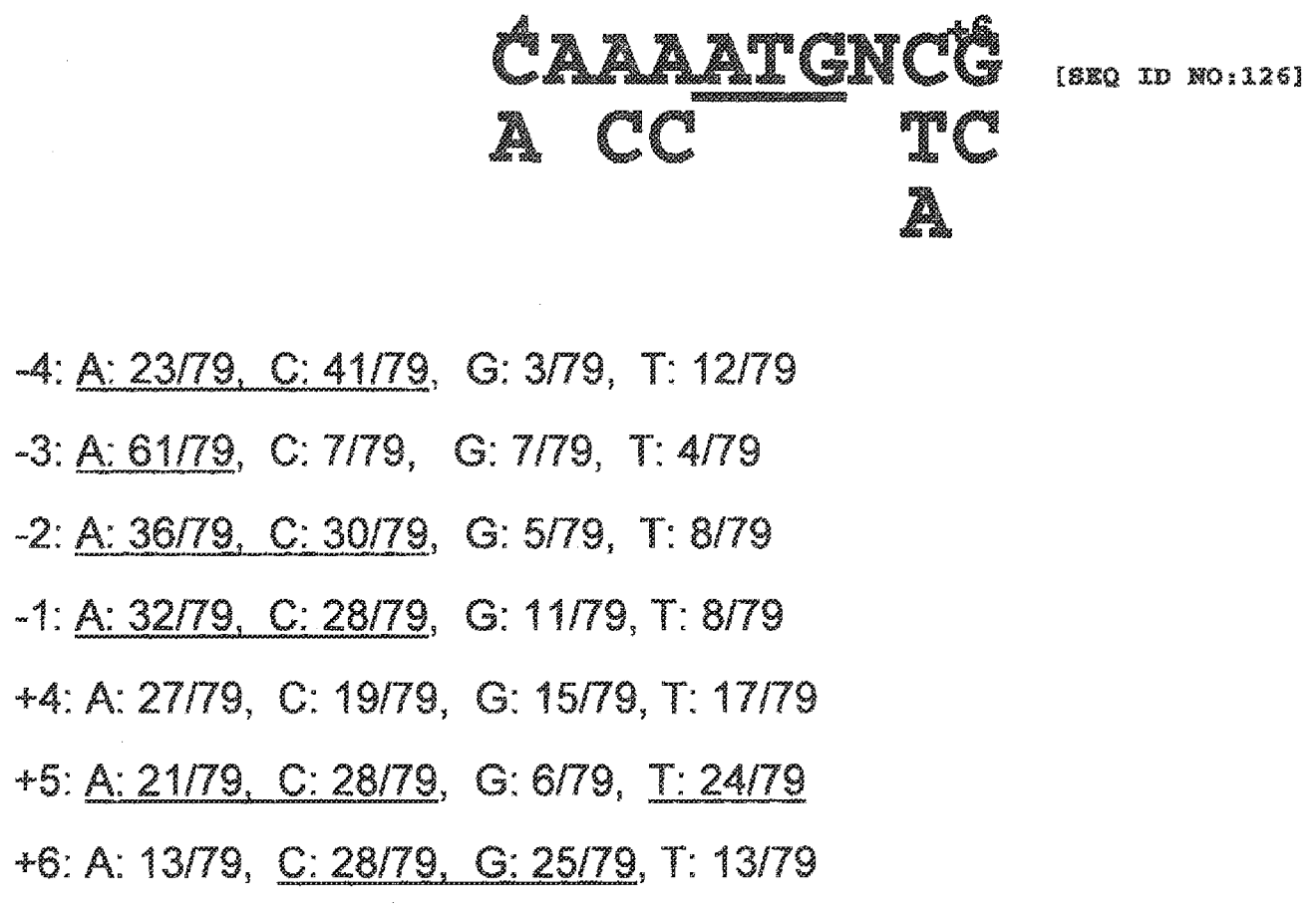

For further optimization of gene expression in *Y. lipolytica*, the consensus sequence around the 'ATG' initiation codon of 79 genes was examined. In FIG. 7, the first 'A' of the underlined ATG translation codon is considered to be +1. Seventy seven percent of the genes analyzed had an 'A' in the −3 position, indicating a strong preference for 'A' at this position. There was also preference for 'A' or 'C' at the −4, −2 and −1 positions, an 'A', 'C' or 'T' at position +5, and a 'G' or 'C' at position +6. Thus, the preferred consensus sequence of the codon-optimized translation initiation site for optimal expression of genes in *Y. lipolytica* is 'MAMMATGNHS' (SEQ ID NO:126), wherein the nucleic acid degeneracy code used is as follows: M=A/C; S=C/G; H=A/C/T; and N=A/C/G/T.

In Vitro Synthesis of a Codon-Optimized Gene

The method used to synthesize the codon-optimized Δ17 desaturase gene is illustrated in FIG. 8. First, eleven pairs of oligonucleotides were designed to extend the entire length of the codon-optimized coding region of the *S. diclina* Δ17 desaturase gene (e.g., D17-1A, D17-1B, D17-2A, D17-2B, D17-3A, D17-3B, D17-4A, D17-4B, D17-5A, D17-5B, D17-6A, D17-6B, D17-7A, D17-7B, D17-8A, D17-8B, D17-9A, D17-9B, D17-10A, D17-10B, D17-11A and D17-11B, corresponding to SEQ ID NOs:10-31). Each pair of sense (A) and anti-sense (B) oligonucleotides were complementary, with the exception of a 4 bp overhang at each 5'-end. Additionally, primers D17-1A, D17-4B, D17-5A, D17-8A and D17-8B also introduced NcoI, BglII and SalI restriction sites for subsequent subcloning, respectively.

100 ng of each oligonucleotide was phosphorylated at 37° C. for 1 hr in a volume of 20 µl containing 50 mM Tris-HCl (pH 7.5), 10 mM MgCl$_2$, 10 mM DTT, 0.5 mM spermidine, 0.5 mM ATP and 10 U of T4 polynucleotide kinase. Each pair of sense and antisense oligonucleotides was mixed and annealed in a thermocycler using the following parameters: 95° C. (2 min), 85° C. (2 min), 65° C. (15 min), 37° C. (15 min), 24° C. (15 min) and 4° C. (15 min). Thus, D17-1A (SEQ ID NO:10) was annealed to D17-1B (SEQ ID NO:11) to produce the double-stranded product "D17-1AB". Similarly, D17-2A (SEQ ID NO:12) was annealed to D17-2B (SEQ ID NO:13) to produce the double-stranded product "D17-2AB", etc.

Three separate pools of annealed, double-stranded oligonucleotides were then ligated together, as shown below:

Pool 1: comprised D17-1AB, D17-2AB, D17-3AB and D17-4AB;
Pool 2: comprised D17-5AB, D17-6AB, D17-7AB and D17-8AB; and
Pool 3: comprised D17-9AB, D17-10AB and D17-11AB.

Each pool of annealed oligonucleotides was mixed in a volume of 20 µl with 10 U of T4 DNA ligase and the ligation reaction was incubated overnight at 16° C.

The product of each ligation reaction was then amplified by PCR. Specifically, using the ligated "Pool 1" mixture (i.e., D17-1AB, D17-2AB, D17-3AB and D17-4AB) as template, and oligonucleotides D17-1 (SEQ ID NO:32) and D17-4R (SEQ ID NO:33) as primers, the first portion of the codon-optimized Δ17 desaturase gene was amplified by PCR. The PCR amplification was carried out in a 50 µl total volume, comprising PCR buffer containing 10 mM KCl, 10 mM (NH$_4$)$_2$SO$_4$, 20 mM Tris-HCl (pH 8.75), 2 mM MgSO$_4$, 0.1% Triton X-100, 100 µg/mL BSA (final concentration), 200 µM each deoxyribonucleotide triphosphate, 10 pmole of each primer and 1 µl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 40 sec. A final extension cycle of 72° C. for 10 min was carried out, followed by reaction termination at 4° C. The 430 bp PCR fragment was subcloned into the pGEM-T easy vector (Promega) to generate pT17(1-4).

Using the ligated "Pool 2" mixture (i.e., D17-5AB, D17-6AB, D17-7AB and D17-8AB) as template, and oligonucleotides D17-5 (SEQ ID NO:34) and D17-8D (SEQ ID NO:35) as primers, the second portion of the codon-optimized Δ17 desaturase gene was amplified similarly by PCR and cloned into pGEM-T-easy vector to generate pT17(5-8). Finally, using the "Pool 3" ligation mixture (i.e., D17-9AB, D17-10AB and D17-11AB) as template, and oligonucleotides D17-8U (SEQ ID NO:36) and D17-11 (SEQ ID NO:37) as primers, the third portion of the codon-optimized Δ17 desaturase gene was amplified similarly by PCR and cloned into pGEM-T-easy vector to generate pT17(9-11).

E. coli was transformed separately with pT17(1-4), pT17(5-8) and pT17(9-11) and the plasmid DNA was isolated from ampicillin-resistant transformants. Plasmid DNA was purified and digested with the appropriate restriction endonucleases to liberate the 420 bp NcoI/BglII fragment of pT17(1-4), the 400 bp BglII/SalI fragment of pT17(5-8) and the 300 bp SalI/NotI fragment of pT17(9-11). These fragments were then combined, ligated together and used as template for amplification of the entire synthetic codon-optimized Δ17 desaturase gene using D17-1 (SEQ ID NO: 32) and D17-11 (SEQ ID NO:37) as primers. The PCR amplification was carried out in a 50 µl total volume, using the conditions described above for each portion of the Δ17 desaturase gene and the thermocycling program as follows: initial denaturation at 95° C. for 3 min, followed by 35 cycles of the following: 95° C. for 1 min, 56° C. for 30 sec, 72° C. for 1.1 min. A final extension cycle of 72° C. for 10 min was carried out, followed by reaction termination at 4° C. This generated a 1.1 kB PCR product.

Construction of Plasmid pYSD17s Containing the Codon-Optimized Δ17 Desaturase

Figure 9B:
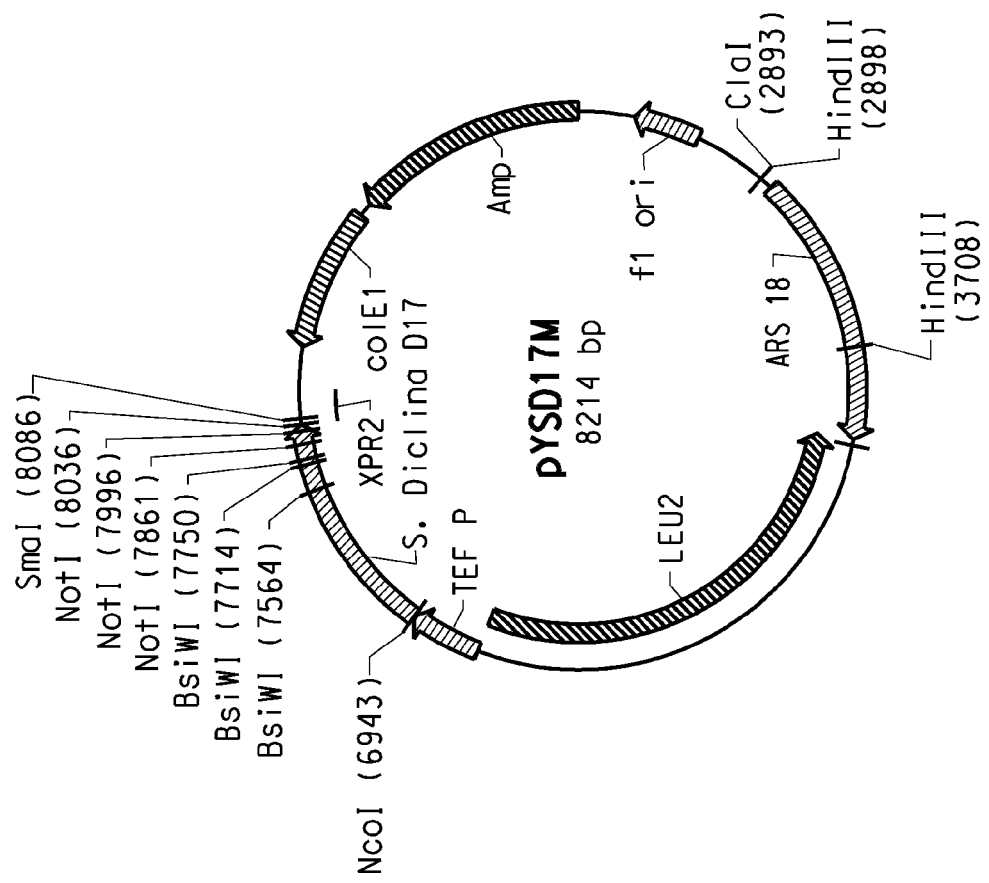
FIG. 9 shows plasmids for expression of the synthetic codon-optimized and wildtype Δ17 desaturase genes in *Y. lipolytica*.
Figure 9A:
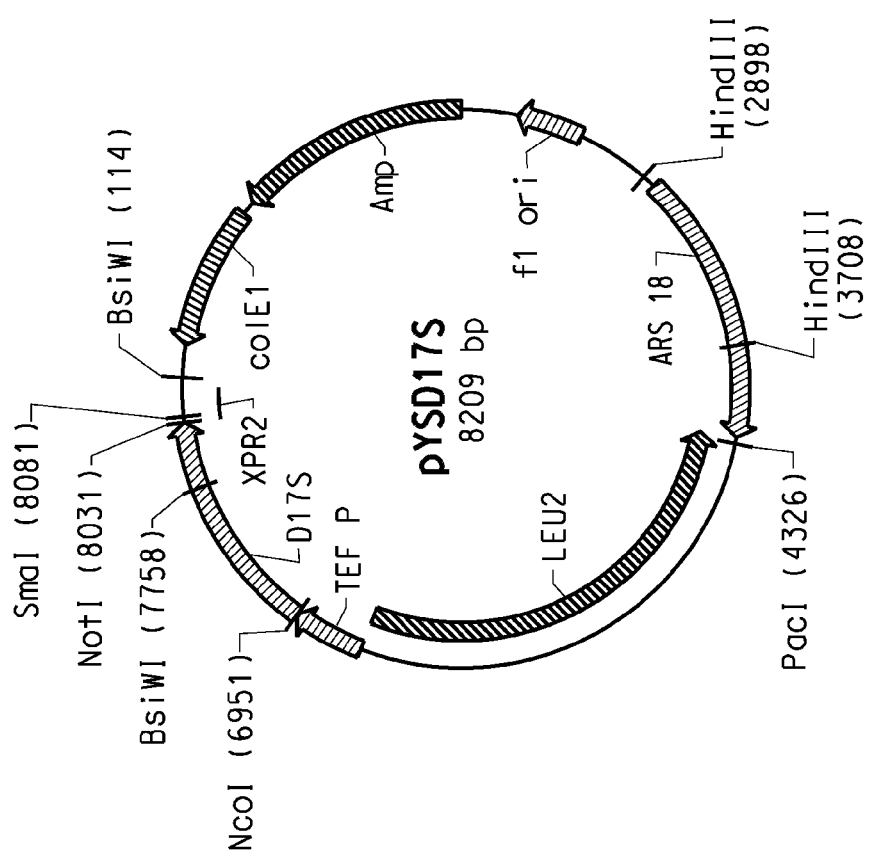

The 1.1 kB PCR product comprising the entire synthetic Δ17 desaturase was digested with NcoI/NotI and subcloned into NcoI/NotI-digested pY5-13 (Example 1) to generate pYSD17S (FIG. 9A).

As an additional "control", to compare the efficiency of the wild type and synthetic genes in Yarrowia, the AT-rich PacI site in pYSD17 (comprising the wild-type gene; described in Example 2) was eliminated by site-directed mutagenesis using YL53 (SEQ ID NO:44) and YL54 (SEQ ID NO:45) as primers to generate pYSD17M (FIG. 9B).

Transformation of Yarrowia lipolytica with the Codon-Optimized Δ17 Desaturase Gene Plasmids containing the wildtype and codon-optimized Δ17 desaturase were transformed separately into Y. lipolytica ATCC #76982 according to the methods described above in Example 2. Using this technique, transformants were obtained that contained the following plasmids:

TABLE 4

Summary Of Plasmids In Transformant Yarrowia

| Plasmid | Description |
| --- | --- |
| pYSD17 | wildtype Δ17 desaturase |
| pYSD17M | wildtype Δ17 desaturase, minus AT-rich PacI site |
| pYSD17S | codon-optimized Δ17 desaturase |

Percent Substrate Conversion with the Codon-Optimized Δ17 Desaturase Gene

Δ17 desaturase converts ARA to EPA (see FIG. 2). The percent substrate conversion ([product]/[substrate+product]*100) of the wildtype and codon-optimized Δ17 desaturase genes was determined in Yarrowia lipolytica containing each alternate plasmid construct, using the methodology described in the General Methods.

Figure 10A:
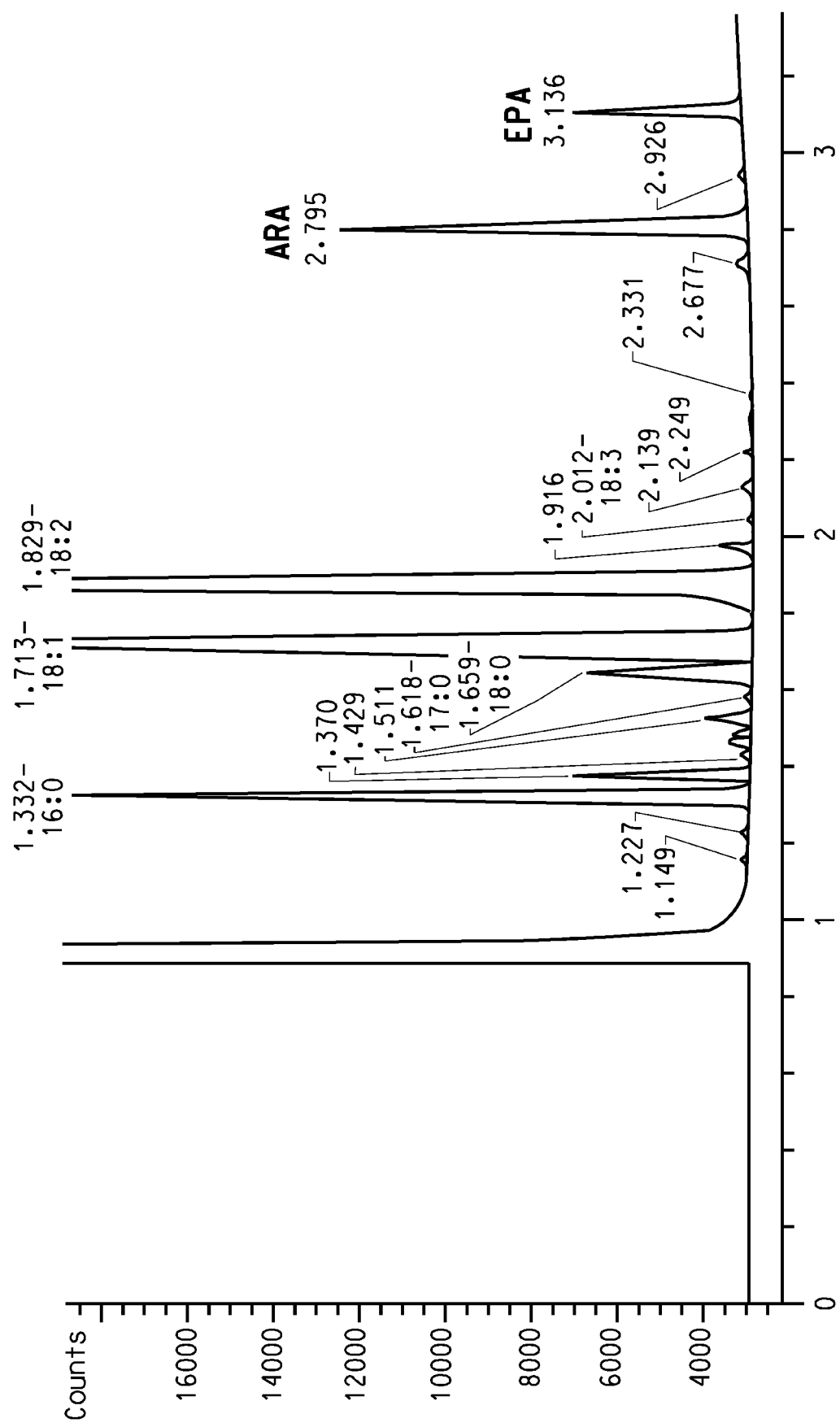

The results of the ARA feeding experiments showed that Yarrowia strains with control plasmids pYSD17 or pYSD17M converted about 23% of intracellular ARA to EPA (FIG. 10A) while those containing the codon-optimized Δ17 desaturase gene within pYSD17S converted about 45% of intracellular ARA to EPA (FIG. 10B). Thus, Yarrowia containing the codon-optimized Δ17 desaturase converted about 2-fold more ARA than the strains containing the wild type S. diclina gene.

Example 4

Construction of Plasmids Suitable for the Coordinate Expression of Multiple Omega Fatty Acid Biosynthesis Genes in Yarrowia lipolytica The present Example describes the synthesis of a variety of expression plasmids that were required in order to construct: 1.) a DNA fragment suitable for integration into the Yarrowia genome for expression of the Δ6 desaturase, PUFA elongase and Δ5 desaturase (for ARA production); and 2.) a DNA fragment suitable for integration into the Yarrowia genome for expression of the Δ6 desaturase, PUFA elongase, Δ5 desaturase and Δ17 desaturase (for EPA production).

Construction of Plasmid pY24

Figure 11:
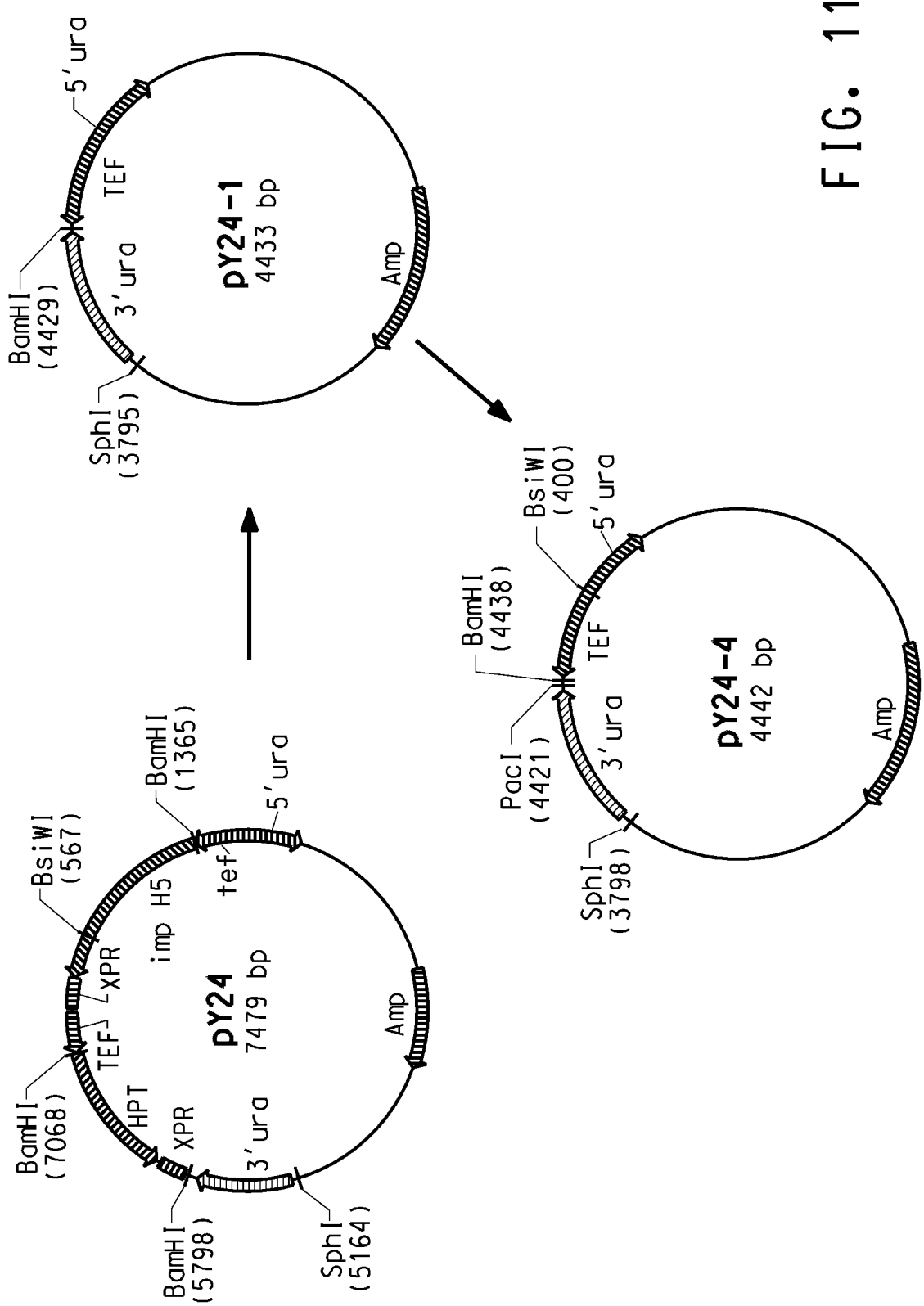
FIG. 11 is a schematic presentation of the construction of intermediate vector pY24-4.

Plasmid pY24 (FIG. 11) was a parent vector for construction of expression cassettes suitable for integration into the genome of *Yarrowia lipolytica*. pY24 was constructed as follows:

Using oligonucleotides KU5 and KU3 (SEQ ID NOs:46 and 47) as primers and *Yarrowia* genomic DNA as template, a 1.7 kB DNA fragment (SEQ ID NO:48) containing the *Yarrowia* URA3 gene was PCR amplified. The PCR amplification was carried out in a 50 µl total volume containing: 100 ng *Yarrowia* genomic DNA, PCR buffer containing 10 mM KCl, 10 mM $(NH_4)_2SO_4$, 20 mM Tris-HCl (pH 8.75), 2 mM $MgSO_4$, 0.1% Triton X-100, 100 µg/mL BSA (final concentration), 200 µM each deoxyribonucleotide triphosphate, 10 pmole of each primer and 1 µl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 2 min. A final extension cycle of 72° C. for 10 min was carried out, followed by reaction termination at 4° C. The PCR product was inserted into pGEM-T easy vector (Promega, Madison, Wis.) to generate pGYUM.

Using oligonucleotides KI5 and KI3 (SEQ ID NOs:50 and 51), a 1.1 kB DNA fragment (SEQ ID NO:52) containing the conjugase gene (or "imp H8") of *Impatients balsama* (clone ids.pk0001.h8; E. I. du Pont de Nemours and Company, Inc., Wilmington, Del.) was PCR amplified. The PCR amplification was carried out in a 50 µl total volume using the components described above, with the exception that 10 ng plasmid DNA of ids.pk0001.h8 was used as template. Amplification was carried out as follows: initial denaturation at 95° C. for 3 min, followed by 35 cycles of the following: 95° C. for 1.5 min, 56° C. for 30 sec, 72° C. for 1.2 min. A final extension cycle of 72° C. for 10 min was carried out, followed by reaction termination at 4° C. The PCR products were digested with NotI, and then inserted into the NotI site of pY5 (FIG. 3) to generate pY9.

Using oligonucleotides KTI5 and KTI3 (SEQ ID NOs:54 and 55), a 1.7 kB DNA fragment (SEQ ID NO:56) containing the TEF::IMP H8::XPR chimeric gene of pY9 was PCR amplified. The PCR amplification was carried out in a 50 µl total volume as described above, with the exception that 10 ng plasmid DNA of pGYUM was used as template. Amplification was carried out as follows: initial denaturation at 95° C. for 3 min, followed by 35 cycles of the following: 95° C. for 1 min, 56° C. for 30 sec, 72° C. for 2 min. A final extension cycle of 72° C. for 10 min was carried out, followed by reaction termination at 4° C. The PCR products were inserted into PCR-Script (Stratagene) to generate pY9R. The 1.7 kB Xho/EcoRV fragment of pY9R was exchanged with the XhoI/EcoRV fragment of pGYUM to generate pY21.

Using oligonucleotides KH5 and KH3 (SEQ ID NOs:58 and 59) as primers and genomic DNA of KS65 as template, a 1 kB DNA fragment (SEQ ID NO:60) containing the *E. coli* hygromycin resistance gene ("HPT"; Kaster, K. R., et al., *Nucleic Acids Res.* 11:6895-6911 (1983)) was PCR amplified. The PCR amplification was carried out in a 50 µl total volume using the components described above, with the exception that 10 ng plasmid DNA of ids.pk0001.h8 was used as template. Amplification was carried out as follows: initial denaturation at 95° C. for 3 min, followed by 35 cycles of the following: 95° C. for 1 min, 56° C. for 30 sec, 72° C. for 1.2 min. A final extension cycle of 72° C. for 10 min was carried out, followed by reaction termination at 4° C. The PCR products were digested with NotI, and then inserted into the NotI site of pY5 (FIG. 3) to generate pTHPT-1.

Using oligonucleotides KTH5 and KTH3 (SEQ ID NOs:62 and 63) as primers and pTHPT-1 plasmid DNA as template, a 1.6 kB DNA fragment (SEQ ID NO:64) containing the TEF::HPT::XPR fusion gene was amplified as described above. The PCR products were digested with BglII and then inserted into pY21 to generate pY24.

Construction of pY24-4

Plasmid pY24 (FIG. 11) was used for construction of expression cassettes suitable for integration into the *Yarrowia lipolytica* genome. The 401 bp of 5'-sequence (SEQ ID NO:66) and the 568 bp of 3'-sequence (SEQ ID NO:67) from the *Y. lipolytica* URA3 gene in pY24 plasmid were used to direct integration of expression cassettes into the Ura loci of the *Yarrowia* genome. Two chimeric genes (TEF::HPT::XPR and TEF::IMP H8::XPR) were first removed from pY24 bp digestion with BamHI and self-ligation to generate pY24-1. PacI and BsiWI sites were introduced into pY24-1 by site-directed mutagenesis using YL63/YL64 (SEQ ID NOs:68 and 69) and YL65/YL66 (SEQ ID NOs:70 and 71) primer pairs, respectively, to generate pY24-4.

Construction of an Integration Vector for Expression of Δ5 Desaturase

The 4261 bp PacI/BsiWI fragment of pYMA5pb (comprising the M. alpine Δ5 desaturase gene; described in Example 2) was ligated into the PacI/BsiWI sites of pY24-4 (FIG. 11) to generate pYZM5 (FIG. 5). HindIII and ClaI sites were introduced into pYZM5 by site-directed mutagenesis using primer pairs YL81 and YL82 (SEQ ID NOs:74 and 75) and YL83 and YL84 (SEQ ID NOs:76 and 77), respectively, to generate pYZM5CH. A PmeI site was introduced into pYZM5CH by site-directed mutagenesis using YL105 and YL106 (SEQ ID NOs:78 and 79) as primers to generate pYZM5CHPP. An AscI site was introduced into pYZM5CHPP by site-directed mutagenesis using YL119 and YL120 (SEQ ID NOs:80 and 81) as primers to generate pYZM5CHPPA (FIG. 5).

Figure 12A:
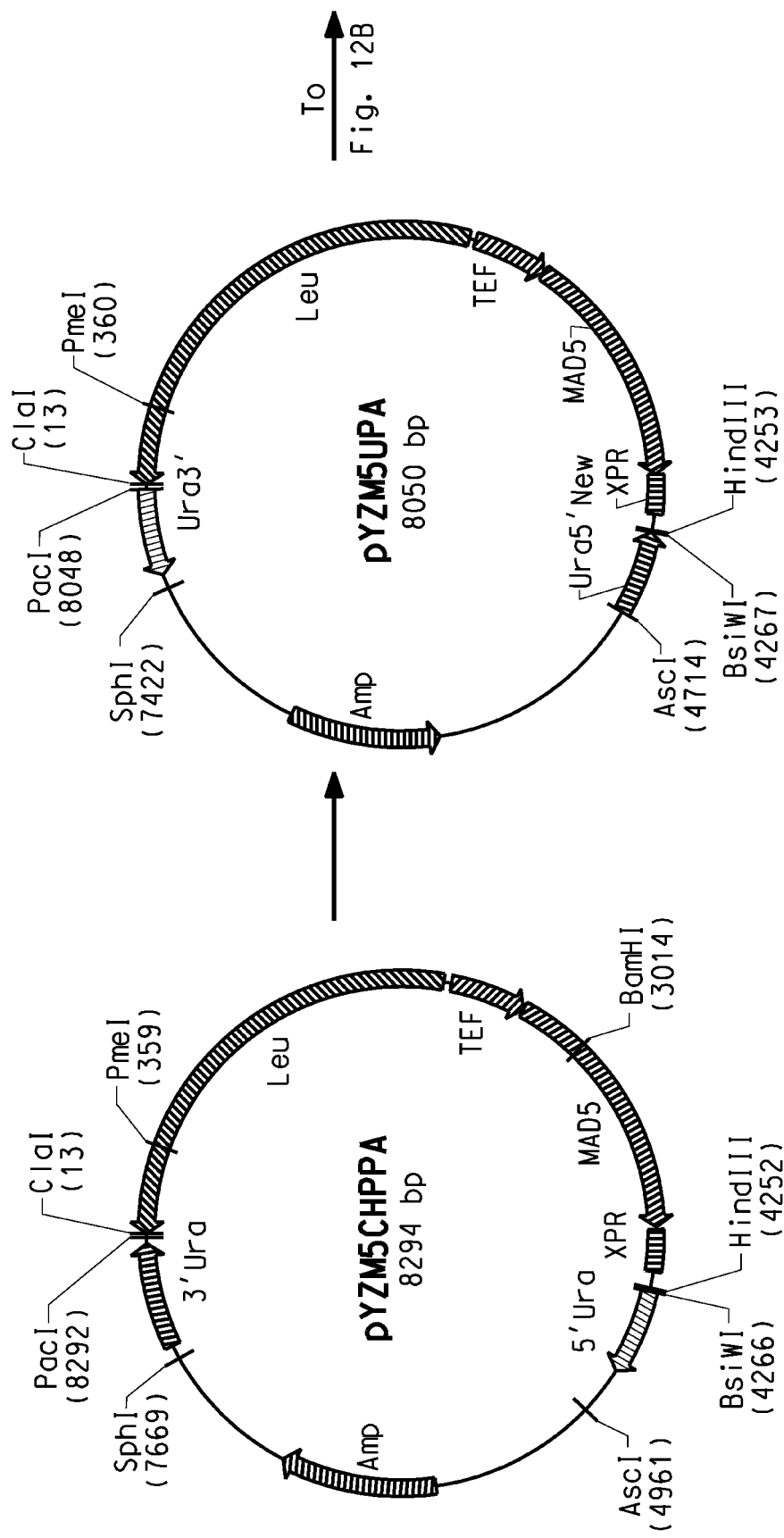
FIG. 12 is a schematic presentation of the construction of intermediate vector pYZV16.
Figure 12B:
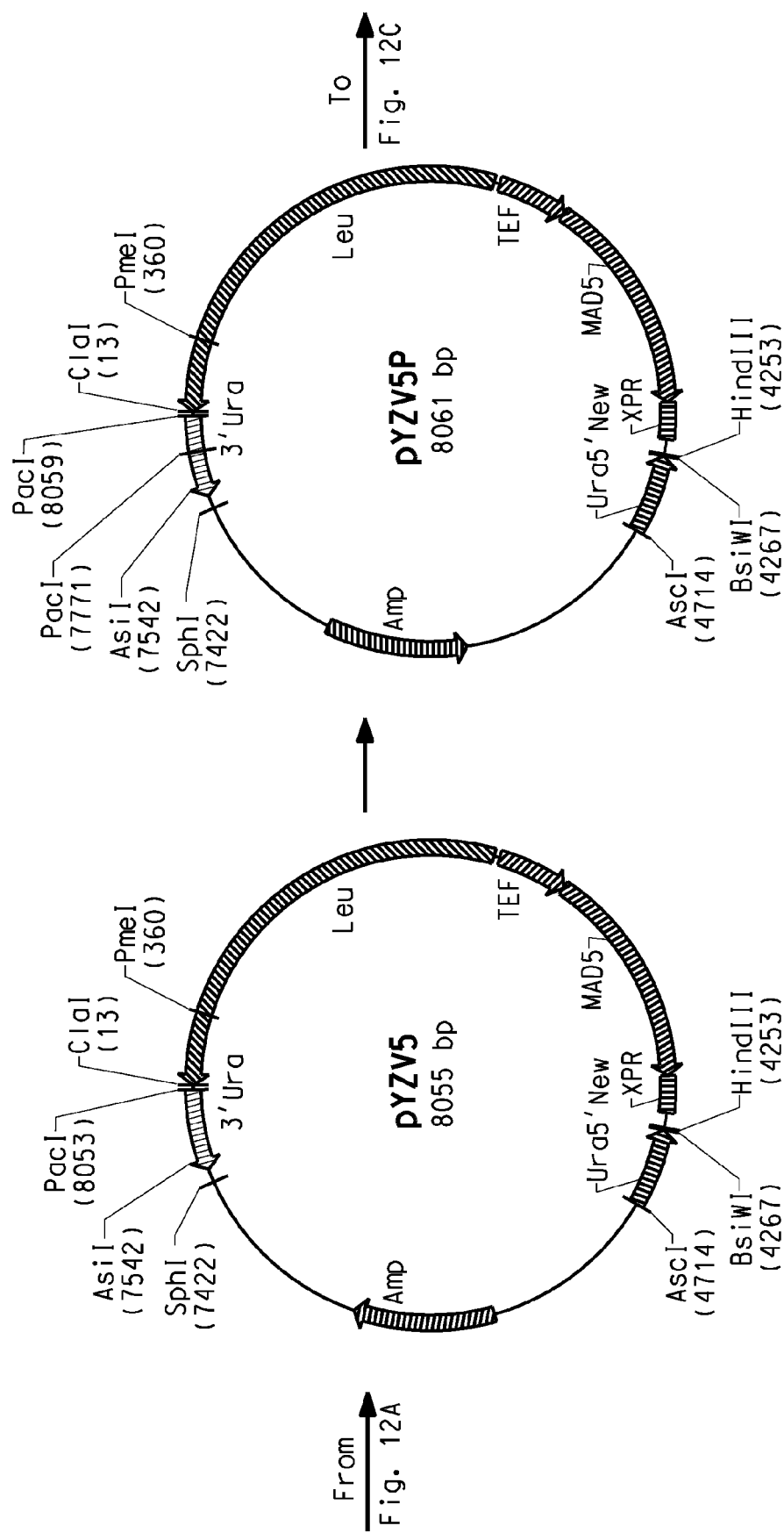
Figure 12C:
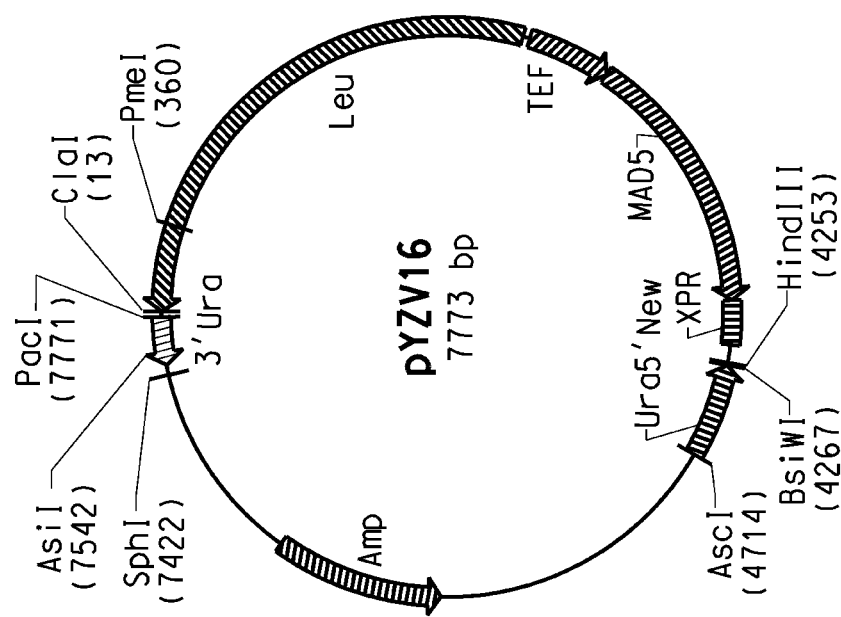
Figure 13A:
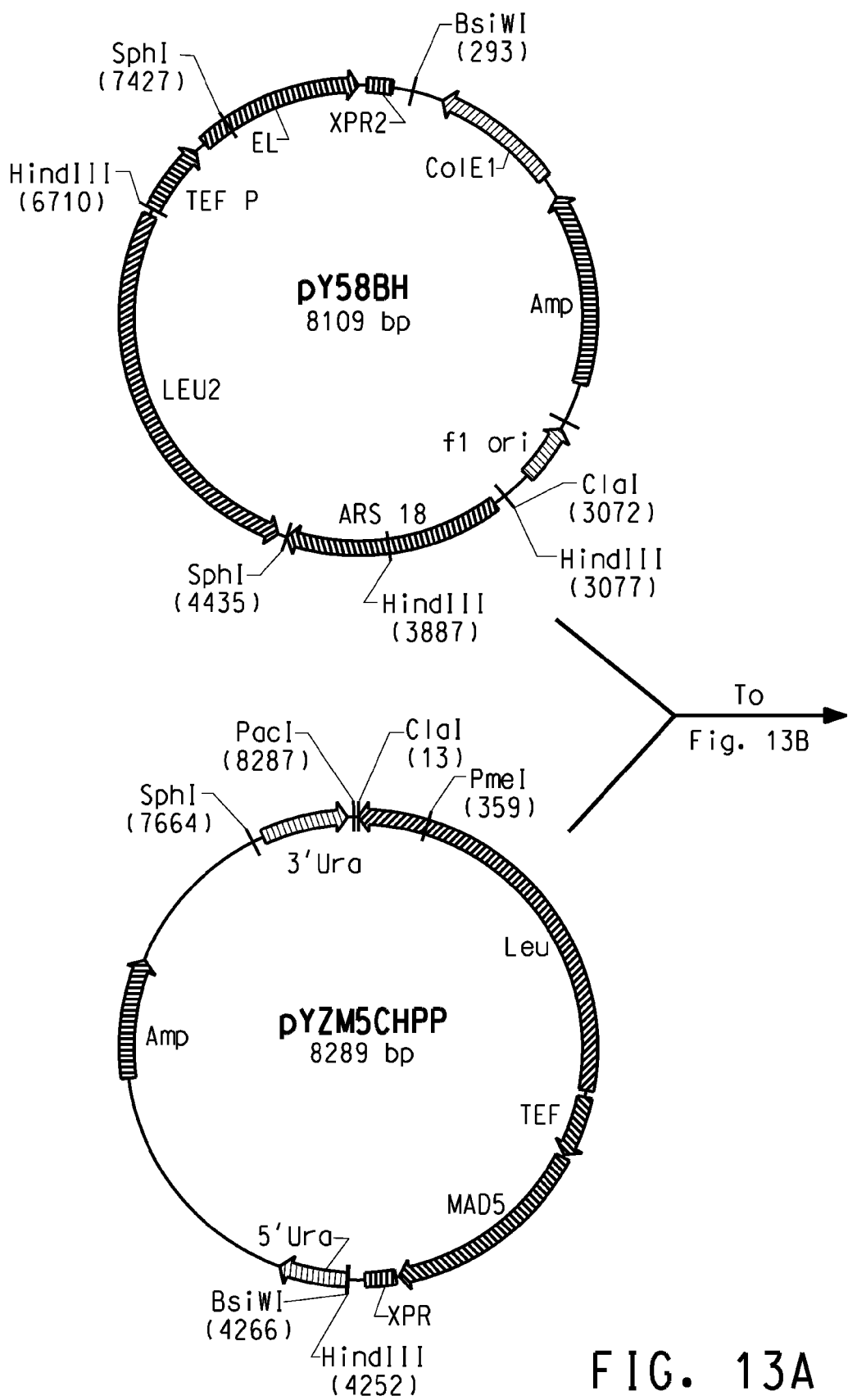
FIG. 13 is a schematic presentation of the construction of integration vector pYZM5EL6.
Figure 13B:
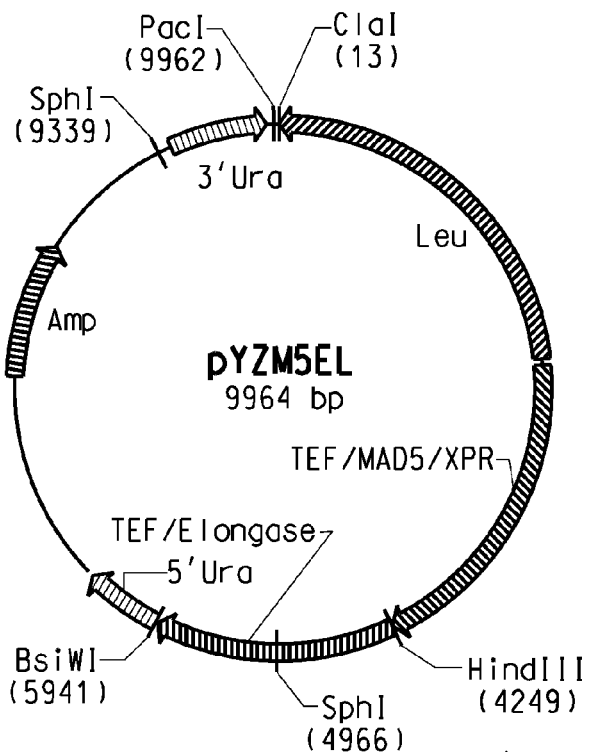
Figure 13B:
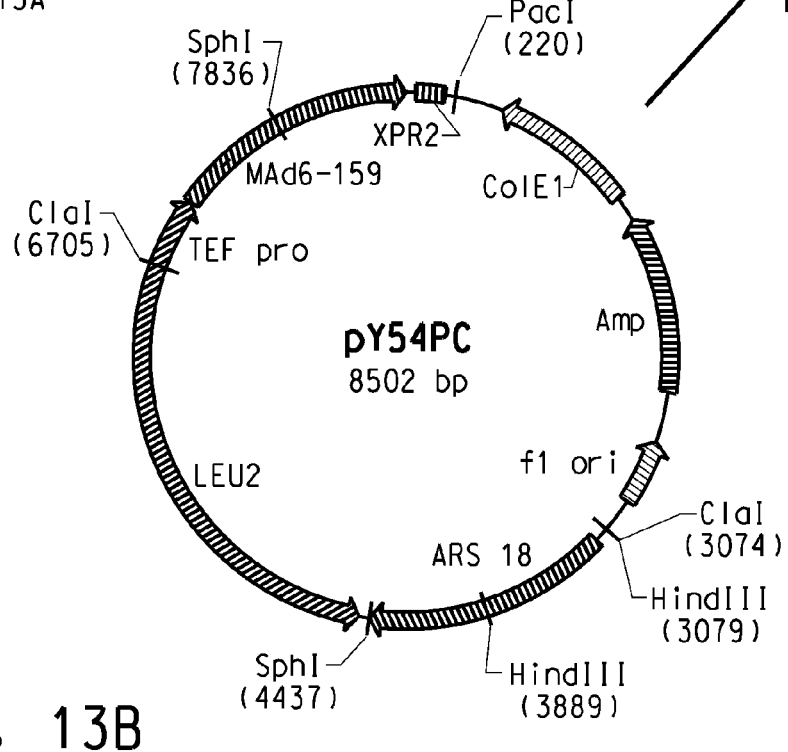
Figure 13C:
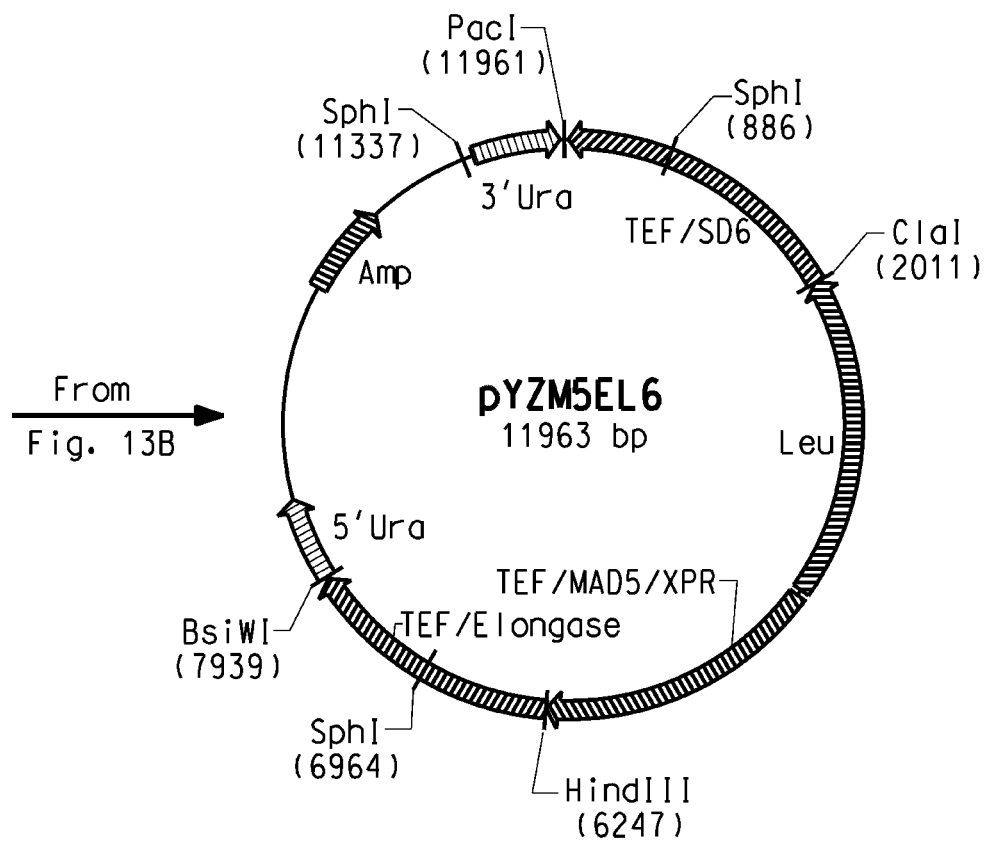

To optimize the integration vector, 440 bp of 5'-non-coding DNA sequence upstream from the *Yarrowia lipolytica* URA3 gene (SEQ ID NO:84) was amplified by PCR using YL121 and YL122 (SEQ ID NOs:82 and 83) as primers. The PCR product was digested with AscI and BsiWI and then exchanged with the AscI/BsiWI fragment of pYZM5CHPPA (FIGS. 5 and 12) to generate pYZM5UPA (FIG. 12). An AscI site was introduced into pYZM5UPA by site-directed mutagenesis using oligonucleotides YL114 and YL115 (SEQ ID NOs:85 and 86) to generate pYZV5. In order to reduce the size of the 3'-non-coding region of the URA3 gene in pYZV5, a second PacI site was introduced into the middle of this region by site-directed mutagenesis using oligonucleotides YL114 and YL115 (described above) to generate pYZV5P. The PacI fragment of pYZV5P was excised by digestion with PacI and religation to generate pYZV16 (FIG. 12). Digestion of pYZV16 with AscI liberates a 5.2 kB DNA fragment (SEQ ID NO:87) suitable for integration and expression of the Δ5 desaturase gene ("MAD5") in the *Y. lipolytica* genome.

Construction of an Integration Vector for Expression of the High Affinity Elongase And Δ5 Desaturase BsiWI and HindIII sites were introduced into pY58 (containing the coding region of the M. alpina high affinity PUFA elongase; described in Example 2) by site-directed mutagenesis using YL61/YL62 (SEQ ID NOs:88 and 89) and YL69/YL70 (SEQ ID NOs:90 and 91) primer pairs, respectively, to generate pY58BH (FIG. 13; elongase gene labeled as "EL"). The 1.7 kB BsiWI/HindIII fragment of pY58BH, which contains the TEF::EL::XPR chimeric gene, was ligated into the BsiWI/HindIII site of pYZM5CHPP (construction described in FIG. 5) to generate pYZM5EL (FIG. 13). This plasmid is suitable for integration and coordinate expression of the *M. alpina* Δ5 desaturase and high affinity PUFA elongase genes in *Y. lipolytica*.

Construction of an Integration Vector for Expression of the Δ6 Desaturase, High Affinity Elongase and Δ5 Desaturase PacI and ClaI sites were introduced into pY54 (containing the *M. alpina* Δ6 desaturase; described in Example 2) by site-directed mutagenesis using YL77/YL78 (SEQ ID NOs: 92 and 93) and YL79A/YL80A (SEQ ID NOs:94 and 95) primer pairs, respectively, to generate pY54PC (FIG. 13; Δ6 desaturase gene labeled as "MAD6"). The 2 kB ClaI/PacI DNA fragment of pY54PC, which contains the TEF:: MAD6::XPR chimeric gene, was ligated into the ClaI/PacI sites of pYZM5EL to generate pYZM5EL6 (FIG. 13). This plasmid is suitable for integration and coordinate expression of the *M. alpina* Δ6 desaturase, Δ5 desaturase and high affinity PUFA elongase genes in the *Y. lipolytica* genome.

Construction of a DNA Fragment Suitable for Integration into the *Yarrowia* Genome, for Expression of the Δ6 Desaturase, PUFA Elongase and Δ5 Desaturase The plasmid pYZV16 (construction described in FIG. 12) was used for construction of plasmids containing multiple expression cassettes.

Figure 14A:
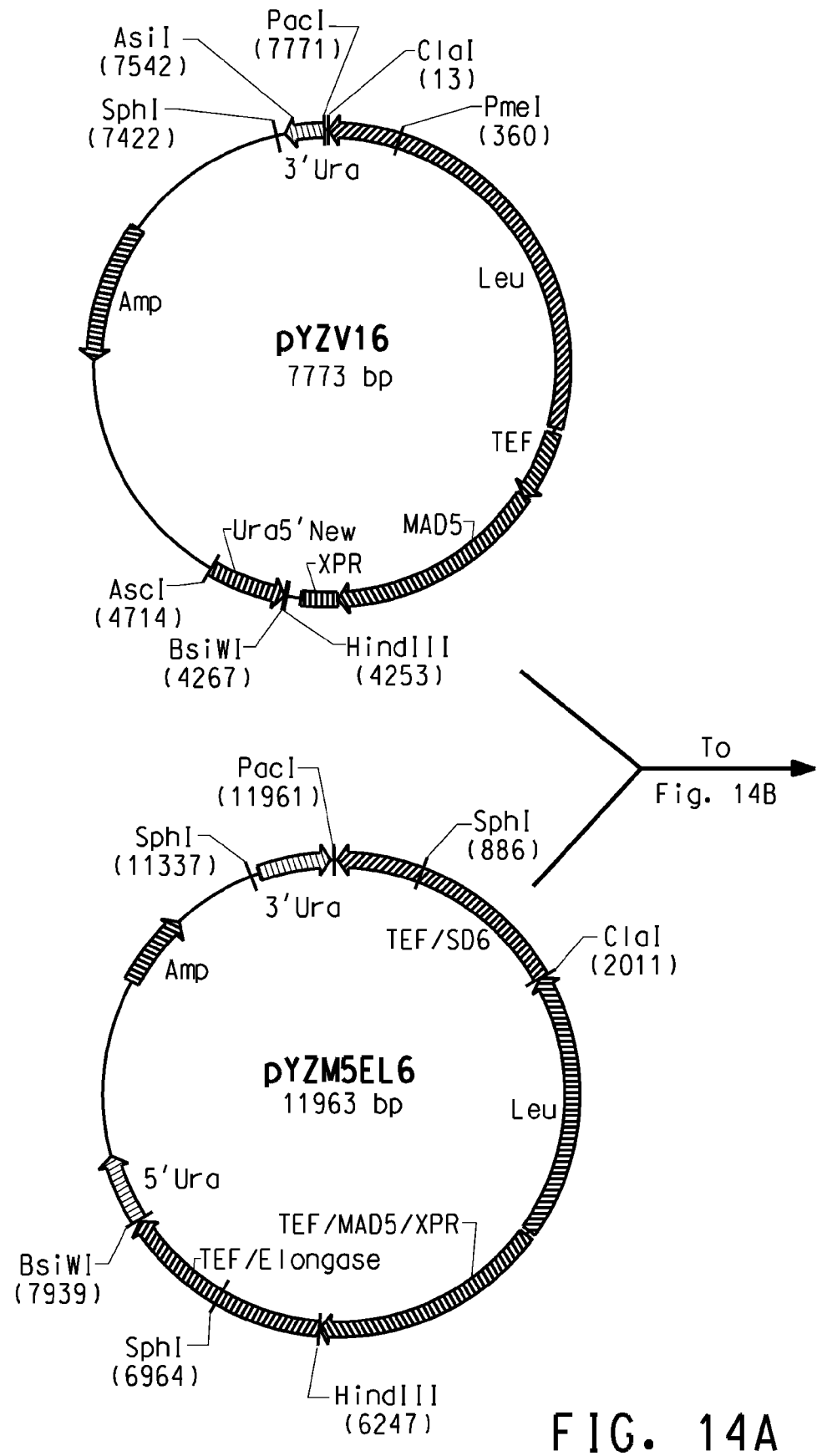
FIG. 14 is a schematic presentation of the construction of integration vectors pYZV5EL6 and pYZV5EL6/17.
Figure 14B:
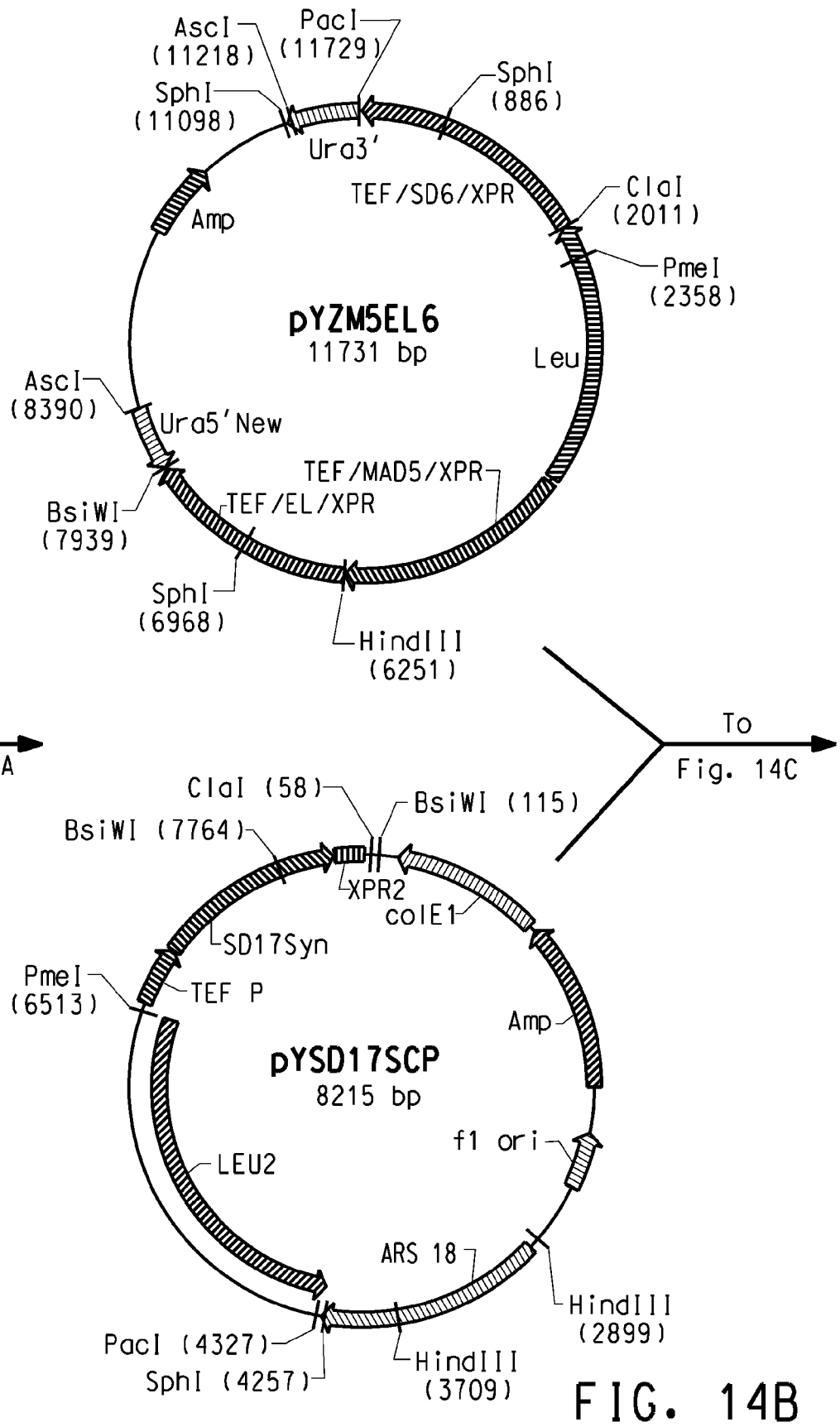
Figure 14C:
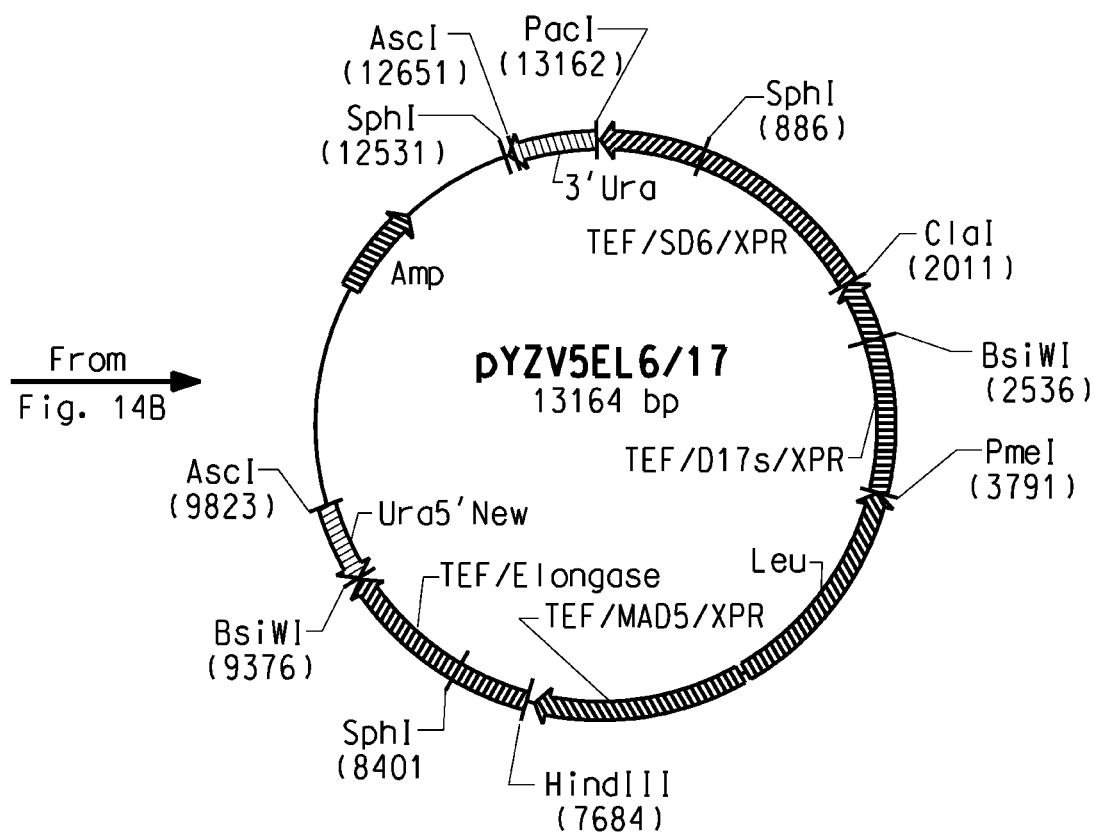

First, the 3.5 kB BsiWI/PacI fragment of pYZV16 was ligated to the 7.9 kB BsiWI/PacI fragment of pYZM5EL6 (construction described in FIG. 13) to generate pYZV5EL6 (FIG. 14). Digestion of pYZV5EL6 with AscI liberates a 8.9 kB DNA fragment (SEQ ID NO:96) suitable for integration and coordinate expression of the Δ6 desaturase, PUFA elongase and Δ5 desaturase genes in the *Y. lipolytica* genome.

Construction of a DNA Fragment Suitable for Integration into the *Yarrowia* Genome, for Expression of the Δ6 Desaturase, PUFA Elongase, Δ5 Desaturase and Δ17 Desaturase As described in Example 3, the synthetic *S. diclina* Δ17 desaturase gene was inserted into the NcoI/NotI sites of pY5-13 to generate pYSD17S (FIG. 9A). ClaI and PmeI sites were introduced into pYSD17S by site-directed mutagenesis using YL101/YL102 (SEQ ID NOs:97 and 98) and YL103/YL104 (SEQ ID NOs:99 and 100) primer pairs, respectively, to generate pYSD17SPC (FIG. 14).

The 347 bp ClaI/PmeI fragment of pYZV5EL6 (FIG. 14) was exchanged with the 1760 bp ClaI/PmeI fragment from pYSD17SPC containing the Δ17 desaturase expression cassette to generate pYZV5E6/17. Digestion of pYZV5E6/17 with AscI liberates a 10.3 kB DNA fragment (SEQ ID NO:101) suitable for integration and coordinate expression of the Δ6 desaturase, PUFA elongase, Δ5 desaturase and Δ17 desaturase genes in the *Y. lipolytica* genome.

Example 5

Biosynthesis of ω-6 Fatty Acids in *Yarrowia lipolytica* Transformants pYZV5EL6 (from Example 4, containing the Δ6 desaturase, PUFA elongase and Δ5 desaturase genes) was digested with the AscI restriction endonuclease and transformed into *Yarrowia lipolytica* according to the methodology described in Example 2.

Of 52 transformants selected on minimal media lacking leucine, 34 could not grow on media also lacking uracil, suggesting that 65% of the transformants contained the 8.9 kB multi-gene expression cassette integrated into the targeted *Yarrowia lipolytica* URA3 locus. Transformants from single colonies were inoculated in minimal media lacking leucine and were incubated at 30° C. for up to 48 hr.

The cells were collected by centrifugation, lipids were extracted, and fatty acid methyl esters were prepared by transesterification and subsequently analyzed with a Hewlett-Packard 6890 GC (according to the methodology described in the General Methods).

Figure 15:
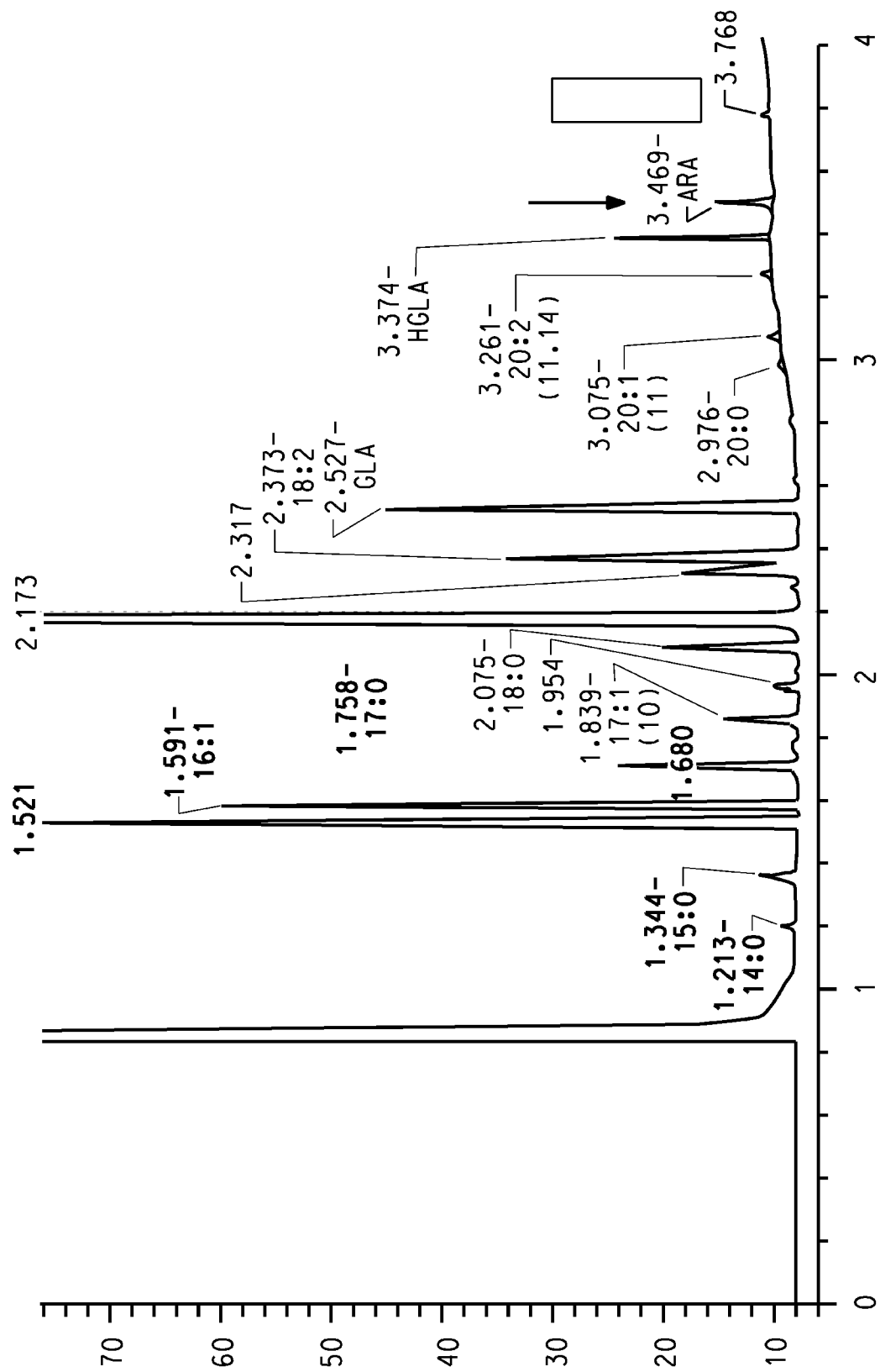
FIG. 15 is a chromatogram illustrating the production of ARA from an engineered *Y. lipolytica*.

GC analyses showed the presence of arachidonic acid (ARA) in the transformants containing the 3 chimeric genes (FIG. 15), but not in the wild type *Yarrowia* control strain. These data confirmed that *Yarrowia lipolytica* was engineered to produce ARA, an ω-6 fatty acid.

Example 6

Biosynthesis of ω-3 Fatty Acids in *Yarrowia lipolytica* Transformants

In a manner similar to that in Example 5, pYZV5E6/17 (from Example 4, containing the Δ6 desaturase, PUFA elongase, Δ5 desaturase and Δ17 desaturase) was digested with the AscI restriction endonuclease and transformed into *Yarrowia lipolytica* (ATCC #76982). Of 133 transformants selected on minimal media lacking leucine, 89 could not grow on media also lacking uracil, suggesting that 67% of the transformants contained the 10.3 kB multi-gene expression cassette integrated into the targeted *Yarrowia lipolytica* URA3 locus.

Figure 16:
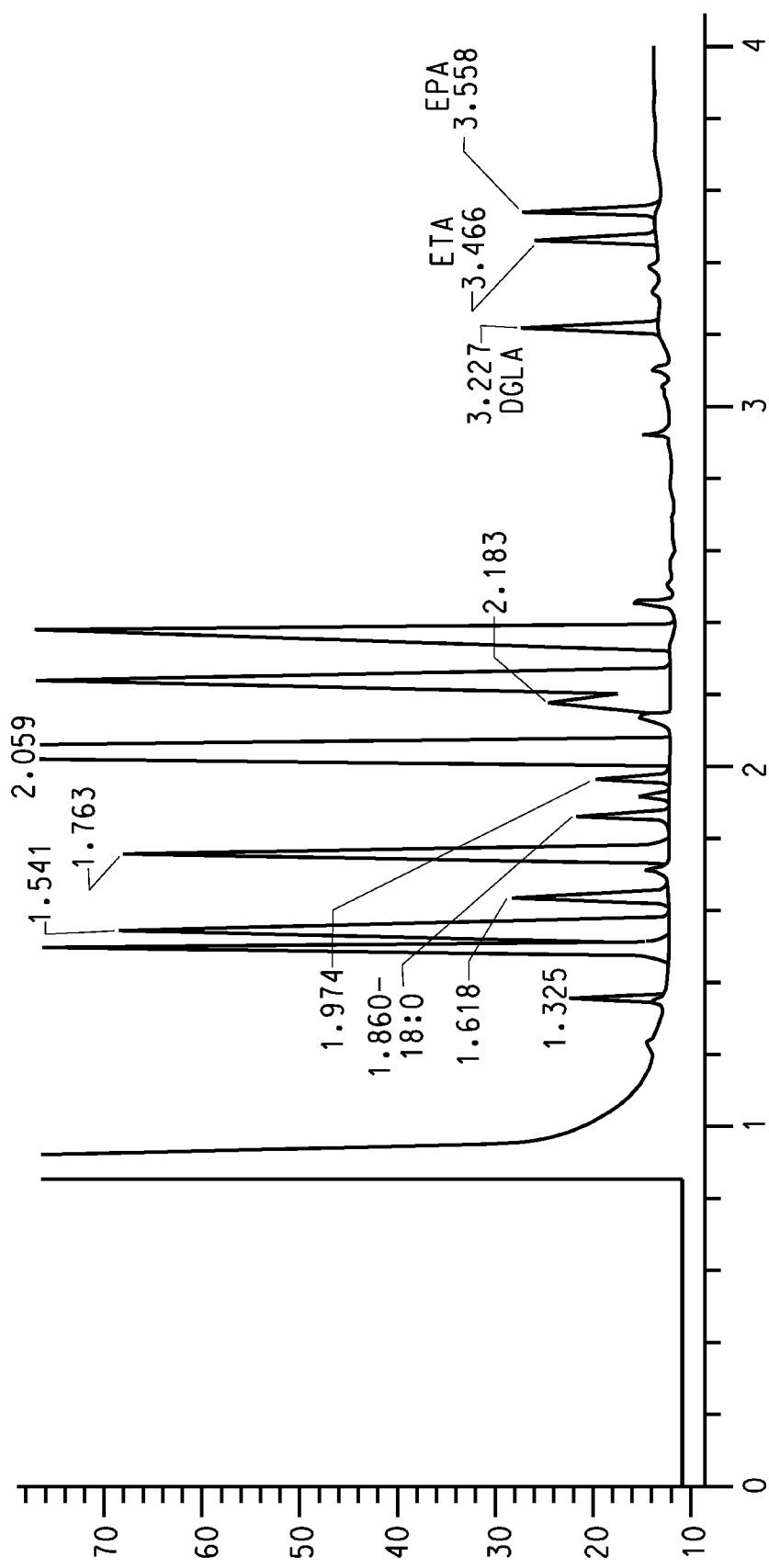
FIG. 16 is a chromatogram illustrating the production of EPA from an engineered *Y. lipolytica*.

GC analyses (according to the methodology described in the General Methods) showed the presence of eicosapentaenoic acid (EPA) in the transformants containing the 4 chimeric genes (FIG. 16), but not in the wild-type *Yarrowia* control strain. These data confirmed that *Yarrowia lipolytica* was engineered to produce EPA, an ω-3 fatty acid.

SEQUENCE LISTING

```
<160> NUMBER OF SEQ ID NOS: 126

<210> SEQ ID NO 1
<211> LENGTH: 1374
<212> TYPE: DNA
<213> ORGANISM: Mortierella alpina AF465281

<400> SEQUENCE: 1
atggctgctg ctcccagtgt gaggacgttt actcgggccg aggttttgaa tgccgaggct      60
ctgaatgagg gcaagaagga tgccgaggca cccttcttga tgatcatcga caacaaggtg     120
tacgatgtcc gcgagttcgt ccctgatcat cccggtggaa gtgtgattct cacgcacgtt     180
```

-continued

```
ggcaaggacg gcactgacgt ctttgacact tttcaccccg aggctgcttg ggagactctt        240
gccaactttt acgttggtga tattgacgag agcgaccgcg atatcaagaa tgatgacttt        300
gcggccgagg tccgcaagct gcgtaccttg ttccagtctc ttggttacta cgattcttcc        360
aaggcatact acgccttcaa ggtctcgttc aacctctgca tctggggttt gtcgacggtc        420
attgtggcca agtggggcca gacctcgacc ctcgccaacg tgctctcggc tgcgcttttg        480
ggtctgttct ggcagcagtg cggatggttg gctcacgact ttttgcatca ccaggtcttc        540
caggaccgtt tctggggtga tctttcggc gccttcttgg aggtgtctg ccagggcttc         600 tcgtcctcgt ggtggaagga caagcacaac actcaccacg ccgcccccaa cgtccacggc        660
gaggatcccg acattgacac ccaccctctg ttgacctgga gtgagcatgc gttggagatg        720
ttctcggatg tcccagatga gggagctgacc cgcatgtggt cgcgtttcat ggtcctgaac        780
cagacctggt tttacttccc cattctctcg tttgcccgtc tctcctggtg cctccagtcc        840
attctctttg tgctgcctaa cggtcaggcc acaagccct cgggcgcgcg tgtgcccatc         900
tcgttggtcg agcagctgtc gcttgcgatg cactggacct ggtacctcgc caccatgttc        960
ctgttcatca aggatcccgt caacatgctg gtgtacttt tggtgtcgca ggcggtgtgc        1020
ggaaacttgt tggcgatcgt gttctcgctc aaccacaacg gtatgcctgt gatctcgaag       1080
gaggaggcgg tcgatatgga tttcttcacg aagcagatca tcacgggtcg tgatgtccac       1140
ccgggtctat ttgccaactg gttcacgggt ggattgaact atcagatcga gcaccacttg       1200
ttcccttcga tgcctcgcca caacttttca agatccagc ctgctgtcga ccctgtgc         1260 aaaaagtaca atgtccgata ccacaccacc ggtatgatcg agggaactgc agaggtcttt       1320
agccgtctga acgaggtctc caaggctacc tccaagatgg gtaaggcgca gtaa            1374
```

<210> SEQ ID NO 2
<211> LENGTH: 457
<212> TYPE: PRT
<213> ORGANISM: Mortierella alpina AF465281

<400> SEQUENCE: 2

```
Met Ala Ala Ala Pro Ser Val Arg Thr Phe Thr Arg Ala Glu Val Leu
 1               5                  10                  15

Asn Ala Glu Ala Leu Asn Glu Gly Lys Lys Asp Ala Glu Ala Pro Phe
             20                  25                  30

Leu Met Ile Ile Asp Asn Lys Val Tyr Asp Val Arg Glu Phe Val Pro
         35                  40                  45

Asp His Pro Gly Gly Ser Val Ile Leu Thr His Val Gly Lys Asp Gly
     50                  55                  60

Thr Asp Val Phe Asp Thr Phe His Pro Glu Ala Ala Trp Glu Thr Leu
 65                  70                  75                  80

Ala Asn Phe Tyr Val Gly Asp Ile Asp Glu Ser Asp Arg Asp Ile Lys
                 85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Val Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
```

|  |  |  | 165 |  |  |  | 170 |  |  |  | 175 |  |
|---|---|---|---|---|---|---|---|---|---|---|---|---|
| His | Gln | Val | Phe | Gln | Asp | Arg | Phe | Trp | Gly | Asp | Leu | Phe | Gly | Ala | Phe |
|  |  |  | 180 |  |  |  | 185 |  |  |  | 190 |  |

Leu Gly Gly Val Cys Gln Gly Phe Ser Ser Trp Trp Lys Asp Lys
            195                 200                 205

His Asn Thr His His Ala Ala Pro Asn Val His Gly Glu Asp Pro Asp
        210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
                260                 265                 270

Arg Leu Ser Trp Cys Leu Gln Ser Ile Leu Phe Val Leu Pro Asn Gly
                275                 280                 285

Gln Ala His Lys Pro Ser Gly Ala Arg Val Pro Ile Ser Leu Val Glu
        290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
        340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
        370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
                420                 425                 430

Ile Glu Gly Thr Ala Glu Val Phe Ser Arg Leu Asn Glu Val Ser Lys
        435                 440                 445

Ala Thr Ser Lys Met Gly Lys Ala Gln
        450                 455

<210> SEQ ID NO 3
<211> LENGTH: 1341
<212> TYPE: DNA
<213> ORGANISM: Mortierella alpina AF067654

<400> SEQUENCE: 3

```
atgggaacgg accaaggaaa aaccttcacc tgggaagagc tggcggccca taacaccaag      60
gacgacctac tcttggccat ccgcggcagg gtgtacgatg tcacaaagtt cttgagccgc     120
catcctggtg gagtggacac tctcctgctc ggagctggcc gagatgttac tccggtcttt     180
gagatgtatc acgcgtttgg ggctgcagat gccattatga agaagtacta tgtcggtaca     240
ctggtctcga atgagctgcc catcttcccg gagccaacgg tgttccacaa aaccatcaag     300
acgagagtcg agggctactt tacggatcgg aacattgatc ccaagaatag accagagatc     360
tggggacgat acgctcttat ctttggatcc ttgatcgctt cctactacgc gcagctcttt     420
gtgcctttcg ttgtcgaacg cacatggctt caggtggtgt ttgcaatcat catgggattt     480
```

```
gcgtgcgcac aagtcggact caaccctctt catgatgcgt ctcactttc agtgacccac      540 aaccccactg tctggaagat tctgggagcc acgcacgact ttttcaacgg agcatcgtac     600
ctggtgtgga tgtaccaaca tatgctcggc catcacccct acaccaacat tgctggagca    660
gatcccgacg tgtcgacgtc tgagcccgat gttcgtcgta tcaagcccaa ccaaaagtgg    720
tttgtcaacc acatcaacca gcacatgttt gttcctttcc tgtacggact gctggcgttc    780
aaggtgcgca ttcaggacat caacatttg tactttgtca agaccaatga cgctattcgt     840
gtcaatccca tctcgacatg gcacactgtg atgttctggg gcggcaaggc tttctttgtc    900
tggtatcgcc tgattgttcc cctgcagtat ctgcccctgg gcaaggtgct gctcttgttc    960
acggtcgcgg acatggtgtc gtcttactgg ctggcgctga ccttccaggc gaaccacgtt   1020
gttgaggaag ttcagtggcc gttgcctgac gagaacggga tcatccaaaa ggactgggca   1080
gctatgcagg tcgagactac gcaggattac gcacacgatt cgcacctctg gaccagcatc   1140
actggcagct tgaactacca ggctgtgcac catctgttcc ccaacgtgtc gcagcaccat   1200
tatcccgata ttctggccat catcaagaac acctgcagcg agtacaaggt tccataccttt  1260 gtcaaggata cgttttggca agcatttgct tcacatttgg agcacttgcg tgttcttgga   1320
ctccgtccca aggaagagta g                                             1341
```

<210> SEQ ID NO 4
<211> LENGTH: 446
<212> TYPE: PRT
<213> ORGANISM: Mortierella alpina AF067654

<400> SEQUENCE: 4

```
Met Gly Thr Asp Gln Gly Lys Thr Phe Thr Trp Glu Glu Leu Ala Ala
1               5                   10                  15

His Asn Thr Lys Asp Asp Leu Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95

Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
```

```
                 210                   215                   220
Ser Thr Ser Glu Pro Asp Val Arg Arg Ile Lys Pro Asn Gln Lys Trp
225                 230                   235                   240

Phe Val Asn His Ile Asn Gln His Met Phe Val Pro Phe Leu Tyr Gly
                245                   250                   255

Leu Leu Ala Phe Lys Val Arg Ile Gln Asp Ile Asn Ile Leu Tyr Phe
            260                   265                   270

Val Lys Thr Asn Asp Ala Ile Arg Val Asn Pro Ile Ser Thr Trp His
        275                   280                   285

Thr Val Met Phe Trp Gly Gly Lys Ala Phe Val Trp Tyr Arg Leu
290                   295                   300

Ile Val Pro Leu Gln Tyr Leu Pro Leu Gly Lys Val Leu Leu Leu Phe
305                 310                   315                   320

Thr Val Ala Asp Met Val Ser Ser Tyr Trp Leu Ala Leu Thr Phe Gln
                325                   330                   335

Ala Asn His Val Val Glu Glu Val Gln Trp Pro Leu Pro Asp Glu Asn
            340                   345                   350

Gly Ile Ile Gln Lys Asp Trp Ala Ala Met Gln Val Glu Thr Thr Gln
        355                   360                   365

Asp Tyr Ala His Asp Ser His Leu Trp Thr Ser Ile Thr Gly Ser Leu
370                   375                   380

Asn Tyr Gln Ala Val His His Leu Phe Pro Asn Val Ser Gln His His
385                 390                   395                   400

Tyr Pro Asp Ile Leu Ala Ile Ile Lys Asn Thr Cys Ser Glu Tyr Lys
                405                   410                   415

Val Pro Tyr Leu Val Lys Asp Thr Phe Trp Gln Ala Phe Ala Ser His
            420                   425                   430

Leu Glu His Leu Arg Val Leu Gly Leu Arg Pro Lys Glu Glu
        435                   440                   445

<210> SEQ ID NO 5
<211> LENGTH: 1077
<212> TYPE: DNA
<213> ORGANISM: Saprolegnia diclina (ATCC #56851)

<400> SEQUENCE: 5
atgactgagg ataagacgaa ggtcgagttc ccgacgctca cggagctcaa gcactcgatc        60
ccgaacgcgt gctttgagtc gaacctcggc ctctcgctct actacgggc  ccgcgcgatc       120
ttcaacgcgt cggcctcggc ggcgctgctc tacgcggcgc gctcgacgcc gttcattgcc       180
gataacgttc tgctccacgc gctcgtttgc gccacctaca tctacgtgca gggcgtcatc       240
ttctggggct cttcacggt  cggccacgac tgcggccact cggccttctc gcgctaccac       300
agcgtcaact ttatcatcgg ctgcatcatg cactctgcga ttttgacgcc gttcgagagc       360
tggcgcgtga cgcaccgcca ccaccacaag aacacgggca acattgataa ggacgagatc       420
ttttacccgc accggtcggt caaggacctc caggacgtgc gccaatgggt ctacacgctc       480
ggcggtgcgt ggtttgtcta cttgaaggtc gggtatgccc cgcgcacgat gagccacttt       540
gacccgtggg acccgctcct ccttcgccgc gcgtcggccg tcatcgtgtc gctcggcgtc       600
tgggccgcct tcttcgccgc gtacgcgtac ctcacatact cgctcggctt tgccgtcatg       660
ggcctctact actatgcgcc gctctttgtc tttgcttcgt tcctcgtcat tacgaccttc       720
ttgcaccaca cgacgaagc  gacgccgtgg tacggcgact cggagtggac gtacgtcaag       780
ggcaacctct cgagcgtcga ccgctcgtac ggcgcgttcg tggacaacct gagccaccac       840
```

```
attggcacgc accaggtcca ccacttgttc ccgatcattc cgcactacaa gctcaacgaa      900
gccaccaagc actttgcggc cgcgtacccg cacctcgtgc gcaggaacga cgagcccatc      960
atcacggcct tcttcaagac cgcgcacctc tttgtcaact acggcgctgt gcccgagacg     1020
gcgcagatct tcacgctcaa agagtcggcc gcggccgcca aggccaagtc ggactaa        1077
```

<210> SEQ ID NO 6
<211> LENGTH: 358
<212> TYPE: PRT
<213> ORGANISM: Saprolegnia declina (ATCC #56851)

<400> SEQUENCE: 6

```
Met Ala Glu Asp Lys Thr Lys Val Glu Phe Pro Thr Leu Thr Glu Leu
1               5                   10                  15

Lys His Ser Ile Pro Asn Ala Cys Phe Glu Ser Asn Leu Gly Leu Ser
            20                  25                  30

Leu Tyr Tyr Thr Ala Arg Ala Ile Phe Asn Ala Ser Ala Ser Ala Ala
        35                  40                  45

Leu Leu Tyr Ala Ala Arg Ser Thr Pro Phe Ile Ala Asp Asn Val Leu
    50                  55                  60

Leu His Ala Leu Val Cys Ala Thr Tyr Ile Tyr Val Gln Gly Val Ile
65                  70                  75                  80

Phe Trp Gly Phe Phe Thr Val Gly His Asp Cys Gly His Ser Ala Phe
                85                  90                  95

Ser Arg Tyr His Ser Val Asn Phe Ile Ile Gly Cys Ile Met His Ser
            100                 105                 110

Ala Ile Leu Thr Pro Phe Glu Ser Trp Arg Val Thr His Arg His His
        115                 120                 125

His Lys Asn Thr Gly Asn Ile Asp Lys Asp Glu Ile Phe Tyr Pro His
    130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175

Met Ser His Phe Asp Pro Trp Asp Pro Leu Leu Leu Arg Arg Ala Ser
            180                 185                 190

Ala Val Ile Val Ser Leu Gly Val Trp Ala Ala Phe Phe Ala Ala Tyr
        195                 200                 205

Ala Tyr Leu Thr Tyr Ser Leu Gly Phe Ala Val Met Gly Leu Tyr Tyr
    210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255

Thr Tyr Val Lys Gly Asn Leu Ser Ser Val Asp Arg Ser Tyr Gly Ala
            260                 265                 270

Phe Val Asp Asn Leu Ser His His Ile Gly Thr His Gln Val His His
        275                 280                 285

Leu Phe Pro Ile Ile Pro His Tyr Lys Leu Asn Glu Ala Thr Lys His
    290                 295                 300

Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335
```

Val Pro Glu Thr Ala Gln Ile Phe Thr Leu Lys Glu Ser Ala Ala Ala
            340                 345                 350

Ala Lys Ala Lys Ser Asp
        355

<210> SEQ ID NO 7
<211> LENGTH: 957
<212> TYPE: DNA
<213> ORGANISM: Mortierella alpina AX464731

<400> SEQUENCE: 7

```
atggagtcga ttgcgccatt cctcccatca aagatgccgc aagatctgtt tatggacctt      60
gccaccgcta tcggtgtccg ggccgcgccc tatgtcgatc ctctcgaggc cgcgctggtg     120
gcccaggccg agaagtacat ccccacgatt gtccatcaca cgcgtgggtt cctggtcgcg     180
gtggagtcgc ctttggcccg tgagctgccg ttgatgaacc cgttccacgt gctgttgatc     240
gtgctcgctt atttggtcac ggtctttgtg ggcatgcaga tcatgaagaa ctttgagcgg     300
ttcgaggtca agacgttttc gctcctgcac aacttttgtc tggtctcgat cagcgcctac     360
atgtgcggtg ggatcctgta cgaggcttat caggccaact atggactgtt tgagaacgct     420
gctgatcata ccttcaaggg tcttcctatg ccaagatga tctggctctt ctacttctcc      480
aagatcatgg agtttgtcga caccatgatc atggtcctca agaagaacaa ccgccagatc     540
tccttcttgc acgtttacca ccacagctcc atcttcacca tctggtggtt ggtcaccttt     600
gttgcaccca acggtgaagc ctacttctct gctgcgttga actcgttcat ccatgtgatc     660
atgtacggct actacttctt gtcggccttg gcttcaagc aggtgtcgtt catcaagttc      720
tacatcacgc gctcgcagat gacacagttc tgcatgatgt cggtccagtc ttcctgggac     780
atgtacgcca tgaaggtcct ggccgcccc ggataccct tcttcatcac ggctctgctt       840
tggttctaca tgtggaccat gctcggtctc ttctacaact tttacagaaa gaacgccaag     900
ttggccaagc aggccaaggc cgacgctgcc aaggagaagg caaggaagtt gcagtaa       957
```

<210> SEQ ID NO 8
<211> LENGTH: 318
<212> TYPE: PRT
<213> ORGANISM: Mortierella alpina AX464731

<400> SEQUENCE: 8

Met Glu Ser Ile Ala Pro Phe Leu Pro Ser Lys Met Pro Gln Asp Leu
1               5                   10                  15

Phe Met Asp Leu Ala Thr Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

```
Ala Tyr Gln Ala Asn Tyr Gly Leu Phe Glu Asn Ala Ala Asp His Thr
        130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
290                 295                 300

Ala Lys Ala Asp Ala Ala Lys Glu Lys Ala Arg Lys Leu Gln
305                 310                 315
```

<210> SEQ ID NO 9
<211> LENGTH: 1077
<212> TYPE: DNA
<213> ORGANISM: Saprolegnia declina

<400> SEQUENCE: 9

```
atggctgagg ataagaccaa ggtcgagttc cctaccctga ctgagctgaa gcactctatc      60
cctaacgctt gctttgagtc caacctcgga ctctcgctct actacactgc ccgagcgatc     120
ttcaacgcat ctgcctctgc tgctctgctc tacgctgccc gatcactcc cttcattgcc     180
gataacgttc tgctccacgc tctggtttgc gccacctaca tctacgtgca gggtgtcatc     240
ttctgggggtt tctttaccgt cggtcacgac tgtggtcact ctgccttctc ccgataccac     300
tccgtcaact tcatcattgg ctgcatcatg cactctgcca ttctgactcc cttcgagtcc     360
tggcgagtga cccaccgaca ccatcacaag aacactggca acattgataa ggacgagatc     420
ttctacccctc atcggtccgt caaggaccctc caggacgtgc acaatgggt ctacacccctc     480
ggaggtgctt ggtttgtcta cctgaaggtc ggatatgctc ctcgaaccat gtcccacttt     540
gaccccctggg accctctcct gcttcgacga gcctccgctg tcatcgtgtc cctcggagtc     600
tgggctgcct tcttcgctgc ctacgcctac ctcacatact cgctcggctt tgccgtcatg     660
ggcctctact actatgctcc tctctttgtc tttgcttcgt tcctcgtcat tactaccttc     720
ttgcatcaca cgacgaagc tactccctgg tacggtgact cggagtggac ctacgtcaag     780
ggcaacctga ctccgtcga ccgatcgtac ggagcttcg tggacaaccct gtctcaccac     840
attggcaccc accaggtcca tcacttgttc cctatcattc cccactacaa gctcaacgaa     900
gccaccaagc actttgctgc cgcttaccct cacctcgtga acgtaacga cgagcccatc     960
attactgcct tcttcaagac cgctcaccctc tttgtcaact acggagctgt gcccgagact    1020
gctcagattt tcacccctcaa agagtctgcc gctgcagcca aggccaagag cgactaa      1077
```

```
<210> SEQ ID NO 10
<211> LENGTH: 105
<212> TYPE: DNA
<213> ORGANISM: Artificial Sequence
<220> FEATURE:
<223> OTHER INFORMATION: Primer D17-1A

<400> SEQUENCE: 10
catggctgag gataagacca aggtcgagtt ccctaccctg actgagctga agcactctat      60
ccctaacgct tgctttgagt ccaacctcgg actctcgctc tacta                    105

<210> SEQ ID NO 11
<211> LENGTH: 106
<212> TYPE: DNA
<213> ORGANISM: Artificial Sequence
<220> FEATURE:
<223> OTHER INFORMATION: Primer D17-1B

<400> SEQUENCE: 11
cagtgtagta gagcgagagt ccgaggttgg actcaaagca agcgttaggg atagagtgct      60
tcagctcagt cagggtaggg aactcgacct tggtcttatc ctcagc                   106

<210> SEQ ID NO 12
<211> LENGTH: 106
<212> TYPE: DNA
<213> ORGANISM: Artificial Sequence
<220> FEATURE:
<223> OTHER INFORMATION: Primer D17-2A

<400> SEQUENCE: 12
cactgcccga gcgatcttca acgcatctgc ctctgctgct ctgctctacg ctgcccgatc      60
tactcccttc attgccgata acgttctgct ccacgctctg gtttgc                   106

<210> SEQ ID NO 13
<211> LENGTH: 106
<212> TYPE: DNA
<213> ORGANISM: Artificial Sequence
<220> FEATURE:
<223> OTHER INFORMATION: Primer D17-2B

<400> SEQUENCE: 13
gtggcgcaaa ccagagcgtg gagcagaacg ttatcggcaa tgaagggagt agatcgggca      60
gcgtagagca gagcagcaga ggcagatgcg ttgaagatcg ctcggg                   106

<210> SEQ ID NO 14
<211> LENGTH: 105
<212> TYPE: DNA
<213> ORGANISM: Artificial Sequence
<220> FEATURE:
<223> OTHER INFORMATION: Primer D17-3A

<400> SEQUENCE: 14
gccacctaca tctacgtgca gggtgtcatc ttctggggtt tctttaccgt cggtcacgac      60
tgtggtcact ctgccttctc ccgataccac tccgtcaact tcatc                    105

<210> SEQ ID NO 15
<211> LENGTH: 105
<212> TYPE: DNA
<213> ORGANISM: Artificial Sequence
<220> FEATURE:
<223> OTHER INFORMATION: Primer D17-3B
```

<400> SEQUENCE: 15
ccaatgatga agttgacgga gtggtatcgg gagaaggcag agtgaccaca gtcgtgaccg      60
acggtaaaga aacccagaa gatgacaccc tgcacgtaga tgtag                       105

<210> SEQ ID NO 16
<211> LENGTH: 105
<212> TYPE: DNA
<213> ORGANISM: Artificial Sequence
<220> FEATURE:
<223> OTHER INFORMATION: Primer D17-4A

<400> SEQUENCE: 16
attggctgca tcatgcactc tgccattctg actcccttcg agtcctggcg agtgacccac      60
cgacaccatc acaagaacac tggcaacatt gataaggacg agatc                      105

<210> SEQ ID NO 17
<211> LENGTH: 105
<212> TYPE: DNA
<213> ORGANISM: Artificial Sequence
<220> FEATURE:
<223> OTHER INFORMATION: Primer D17-4B

<400> SEQUENCE: 17
tagaagatct cgtccttatc aatgttgcca gtgttcttgt gatggtgtcg gtgggtcact      60
cgccaggact cgaagggagt cagaatggca gagtgcatga tgcag                      105

<210> SEQ ID NO 18
<211> LENGTH: 105
<212> TYPE: DNA
<213> ORGANISM: Artificial Sequence
<220> FEATURE:
<223> OTHER INFORMATION: Primer D17-5A

<400> SEQUENCE: 18
acgagatctt ctaccctcat cggtccgtca aggacctcca ggacgtgcga caatgggtct      60
acaccctcgg aggtgcttgg tttgtctacc tgaaggtcgg atatg                      105

<210> SEQ ID NO 19
<211> LENGTH: 107
<212> TYPE: DNA
<213> ORGANISM: Artificial Sequence
<220> FEATURE:
<223> OTHER INFORMATION: Primer D17-5B

<400> SEQUENCE: 19
aggagcatat ccgaccttca ggtagacaaa ccaagcacct ccgagggtgt agacccattg      60
tcgcacgtcc tggaggtcct tgacggaccg atgagggtag aagatct                    107

<210> SEQ ID NO 20
<211> LENGTH: 105
<212> TYPE: DNA
<213> ORGANISM: Artificial Sequence
<220> FEATURE:
<223> OTHER INFORMATION: Primer D17-6A

<400> SEQUENCE: 20
ctcctcgaac catgtcccac tttgaccct gggaccctct cctgcttcga cgagcctccg       60
ctgtcatcgt gtccctcgga gtctgggctg ccttcttcgc tgcct                      105

<210> SEQ ID NO 21
<211> LENGTH: 106

```
<212> TYPE: DNA
<213> ORGANISM: Artificial Sequence
<220> FEATURE:
<223> OTHER INFORMATION: Primer D17-6B

<400> SEQUENCE: 21
aggcgtaggc agcgaagaag gcagcccaga ctccgaggga cacgatgaca gcggaggctc      60
gtcgaagcag gagagggtcc caggggtcaa agtgggacat ggttcg                    106

<210> SEQ ID NO 22
<211> LENGTH: 104
<212> TYPE: DNA
<213> ORGANISM: Artificial Sequence
<220> FEATURE:
<223> OTHER INFORMATION: Primer D17-7A

<400> SEQUENCE: 22
acgcctacct cacatactcg ctcggctttg ccgtcatggg cctctactac tatgctcctc      60
tctttgtctt tgcttcgttc ctcgtcatta ctaccttctt gcat                      104

<210> SEQ ID NO 23
<211> LENGTH: 103
<212> TYPE: DNA
<213> ORGANISM: Artificial Sequence
<220> FEATURE:
<223> OTHER INFORMATION: Primer D17-7B

<400> SEQUENCE: 23
ttgtgatgca agaaggtagt aatgacgagg aacgaagcaa agacaaagag aggagcatag      60
tagtagaggc ccatgacggc aaagccgagc gagtatgtga ggt                       103

<210> SEQ ID NO 24
<211> LENGTH: 106
<212> TYPE: DNA
<213> ORGANISM: Artificial Sequence
<220> FEATURE:
<223> OTHER INFORMATION: Primer D17-8A

<400> SEQUENCE: 24
cacaacgacg aagctactcc ctggtacggt gactcggagt ggacctacgt caagggcaac      60
ctgagctccg tcgaccgatc gtacggagct ttcgtggaca acctgt                    106

<210> SEQ ID NO 25
<211> LENGTH: 106
<212> TYPE: DNA
<213> ORGANISM: Artificial Sequence
<220> FEATURE:
<223> OTHER INFORMATION: Primer D17-8B

<400> SEQUENCE: 25
gtgagacagg ttgtccacga aagctccgta cgatcggtcg acggagctca ggttgccctt      60
gacgtaggtc cactccgagt caccgtacca gggagtagct tcgtcg                    106

<210> SEQ ID NO 26
<211> LENGTH: 102
<212> TYPE: DNA
<213> ORGANISM: Artificial Sequence
<220> FEATURE:
<223> OTHER INFORMATION: Primer D17-9A

<400> SEQUENCE: 26
ctcaccacat tggcacccac caggtccatc acttgttccc tatcattccc cactacaagc      60
```

```
tcaacgaagc caccaagcac tttgctgccg cttaccctca cc                        102
```

<210> SEQ ID NO 27
<211> LENGTH: 102
<212> TYPE: DNA
<213> ORGANISM: Artificial Sequence
<220> FEATURE:
<223> OTHER INFORMATION: Primer D17-9B

<400> SEQUENCE: 27

```
cacgaggtga gggtaagcgg cagcaaagtg cttggtggct tcgttgagct tgtagtgggg     60
aatgataggg aacaagtgat ggacctggtg ggtgccaatg tg                        102
```

<210> SEQ ID NO 28
<211> LENGTH: 76
<212> TYPE: DNA
<213> ORGANISM: Artificial Sequence
<220> FEATURE:
<223> OTHER INFORMATION: Primer D17-10A

<400> SEQUENCE: 28

```
tcgtgagacg taacgacgag cccatcatta ctgccttctt caagaccgct cacctctttg     60
tcaactacgg agctgt                                                     76
```

<210> SEQ ID NO 29
<211> LENGTH: 76
<212> TYPE: DNA
<213> ORGANISM: Artificial Sequence
<220> FEATURE:
<223> OTHER INFORMATION: Primer D17-10B

<400> SEQUENCE: 29

```
cgggcacagc tccgtagttg acaaagaggt gagcggtctt gaagaaggca gtaatgatgg     60
gctcgtcgtt acgtct                                                     76
```

<210> SEQ ID NO 30
<211> LENGTH: 67
<212> TYPE: DNA
<213> ORGANISM: Artificial Sequence
<220> FEATURE:
<223> OTHER INFORMATION: Primer D17-11A

<400> SEQUENCE: 30

```
gcccgagact gctcagattt tcaccctcaa agagtctgcc gctgcagcca aggccaagag     60
cgactaa                                                               67
```

<210> SEQ ID NO 31
<211> LENGTH: 62
<212> TYPE: DNA
<213> ORGANISM: Artificial Sequence
<220> FEATURE:
<223> OTHER INFORMATION: Primer D17-11B

<400> SEQUENCE: 31

```
ttagtcgctc ttggccttgg ctgcagcggc agactctttg agggtgaaaa tctgagcagt     60
ct                                                                    62
```

<210> SEQ ID NO 32
<211> LENGTH: 32
<212> TYPE: DNA
<213> ORGANISM: Artificial Sequence
<220> FEATURE:
<223> OTHER INFORMATION: Primer D17-1

```
<400> SEQUENCE: 32
tttccatggc tgaggataag accaaggtcg ag                                    32

<210> SEQ ID NO 33
<211> LENGTH: 34
<212> TYPE: DNA
<213> ORGANISM: Artificial Sequence
<220> FEATURE:
<223> OTHER INFORMATION: Primer D17-4R

<400> SEQUENCE: 33
ccctagaaga tctcgtcctt atcaatgttg ccag                                  34

<210> SEQ ID NO 34
<211> LENGTH: 27
<212> TYPE: DNA
<213> ORGANISM: Artificial Sequence
<220> FEATURE:
<223> OTHER INFORMATION: Primer D17-5

<400> SEQUENCE: 34
cccacgagat cttctaccct catcggt                                          27

<210> SEQ ID NO 35
<211> LENGTH: 24
<212> TYPE: DNA
<213> ORGANISM: Artificial Sequence
<220> FEATURE:
<223> OTHER INFORMATION: Primer D17-8D

<400> SEQUENCE: 35
gaaagctccg tacgatcggt cgac                                             24

<210> SEQ ID NO 36
<211> LENGTH: 24
<212> TYPE: DNA
<213> ORGANISM: Artificial Sequence
<220> FEATURE:
<223> OTHER INFORMATION: Primer D17-8U

<400> SEQUENCE: 36
gtcgaccgat cgtacggagc tttc                                             24

<210> SEQ ID NO 37
<211> LENGTH: 34
<212> TYPE: DNA
<213> ORGANISM: Artificial Sequence
<220> FEATURE:
<223> OTHER INFORMATION: Primer D17-11

<400> SEQUENCE: 37
aaagcggccg cttagtcgct cttggccttg gctg                                  34

<210> SEQ ID NO 38
<211> LENGTH: 19
<212> TYPE: DNA
<213> ORGANISM: Artificial Sequence
<220> FEATURE:
<223> OTHER INFORMATION: Primer TEF5'

<400> SEQUENCE: 38
agagaccggg ttggcggcg                                                   19

<210> SEQ ID NO 39
```

<210> SEQ ID NO 39
<211> LENGTH: 30
<212> TYPE: DNA
<213> ORGANISM: Artificial Sequence
<220> FEATURE:
<223> OTHER INFORMATION: Primer TEF3'

<400> SEQUENCE: 39
ttggatcctt tgaatgattc ttatactcag    30

<210> SEQ ID NO 40
<211> LENGTH: 29
<212> TYPE: DNA
<213> ORGANISM: Artificial Sequence
<220> FEATURE:
<223> OTHER INFORMATION: Primer XPR5'

<400> SEQUENCE: 40
tttccgcggc ccgagattcc ggcctcttc    29

<210> SEQ ID NO 41
<211> LENGTH: 31
<212> TYPE: DNA
<213> ORGANISM: Artificial Sequence
<220> FEATURE:
<223> OTHER INFORMATION: Primer XPR3'

<400> SEQUENCE: 41
tttccgcgga cacaatatct ggtcaaattt c    31

<210> SEQ ID NO 42
<211> LENGTH: 33
<212> TYPE: DNA
<213> ORGANISM: Artificial Sequence
<220> FEATURE:
<223> OTHER INFORMATION: Primer YL21A

<400> SEQUENCE: 42
tttccatggc tgaggataag acgaaggtcg agt    33

<210> SEQ ID NO 43
<211> LENGTH: 36
<212> TYPE: DNA
<213> ORGANISM: Artificial Sequence
<220> FEATURE:
<223> OTHER INFORMATION: Primer YL22

<400> SEQUENCE: 43
cccttaatta attagtccga cttggccttg gcggcc    36

<210> SEQ ID NO 44
<211> LENGTH: 36
<212> TYPE: DNA
<213> ORGANISM: Artificial Sequence
<220> FEATURE:
<223> OTHER INFORMATION: Primer YL53

<400> SEQUENCE: 44
gccaagtcgg actaagctgc taactagagc ggccgc    36

<210> SEQ ID NO 45
<211> LENGTH: 36
<212> TYPE: DNA
<213> ORGANISM: Artificial Sequence
<220> FEATURE:
<223> OTHER INFORMATION: Primer YL54

<400> SEQUENCE: 45

```
gcggccgctc tagttagcag cttagtccga cttggc                                 36
```

<210> SEQ ID NO 46
<211> LENGTH: 35
<212> TYPE: DNA
<213> ORGANISM: Artificial Sequence
<220> FEATURE:
<223> OTHER INFORMATION: Primer KU5

<400> SEQUENCE: 46

```
tttgcccggg cgagtatctg tctgactcgt cattg                                  35
```

<210> SEQ ID NO 47
<211> LENGTH: 33
<212> TYPE: DNA
<213> ORGANISM: Artificial Sequence
<220> FEATURE:
<223> OTHER INFORMATION: Primer KU3

<400> SEQUENCE: 47

```
aaagcccggg caaaggcctg tttctcggtg tac                                    33
```

<210> SEQ ID NO 48
<211> LENGTH: 1710
<212> TYPE: DNA
<213> ORGANISM: Yarrowia lipolytica

<400> SEQUENCE: 48

```
gtcgacgagt atctgtctga ctcgtcattg ccgcctttgg agtacgactc caactatgag        60
tgtgcttgga tcactttgac gatacattct tcgttggagg ctgtgggtct gacagctgcg       120
ttttcggcgc ggttggccga caacaatatc agctgcaacg tcattgctgg ctttcatcat       180
gatcacattt ttgtcggcaa aggcgacgcc cagagagcca ttgacgttct ttctaatttg       240
gaccgatagc cgtatagtcc agtctatcta aagttcaac taactcgtaa ctattaccat        300
aacatatact tcactgcccc agataaggtt ccgataaaaa gttctgcaga ctaaatttat       360
ttcagtctcc tcttcaccac caaaatgccc tcctacgaag ctcgagctaa cgtccacaag       420
tccgcctttg ccgctcgagt gctcaagctc gtggcagcca agaaaaccaa cctgtgtgct       480
tctctggatg ttaccaccac caaggagctc attgagcttg ccgataaggt cggaccttat       540
gtgtgcatga tcaagaccca tatcgacatc attgacgact caccctacgc cggcactgtg       600
ctccccctca aggaacttgc tcttaagcac ggtttcttcc tgttcgagga cagaaagttc       660
gcagatattg caacactgt caagcaccag tacaagaacg tgtctaccg aatcgccgag         720
tggtccgata tcaccaacgc ccacggtgta cccggaaccg gaatcattgc tggcctgcga       780
gctggtgccg aggaaactgt ctctgaacag aagaaggagg acgtctctga ctacgagaac       840
tcccagtaca aggagttcct ggtcccctct cccaacgaga agctggccag aggtctgctc       900
atgctggccg agctgtcttg caagggctct ctggccactg cgagtactc caagcagacc        960
attgagcttg cccgatccga ccccgagttt gtggttggct tcattgccca gaaccgacct      1020
aagggcgact ctgaggactg gcttattctg accccggg tgggtcttga cgacaaggga       1080
gacgctctcg acagcagta ccgaactgtt gaggatgtca tgtctaccgg aacggatatc       1140
ataattgtcg gccgaggtct gtacggccag aaccgagatc ctattgagga ggccaagcga      1200
taccagaagg ctggctggga ggcttaccag aagattaact gttagaggtt agactatgga      1260
tatgtcattt aactgtgtat atagagagcg tgcaagtatg gagcgcttgt tcagcttgta      1320
```

-continued

```
tgatggtcag acgacctgtc tgatcgagta tgtatgatac tgcacaacct gtgtatccgc   1380
atgatctgtc caatggggca tgttgttgtg tttctcgata cggagatgct gggtacaagt   1440
agctaatacg attgaactac ttatacttat atgaggcttg aagaaagctg acttgtgtat   1500
gacttattct caactacatc cccagtcaca ataccaccac tgcactacca ctacaccaaa   1560
accatgatca aaccacccat ggacttcctg gaggcagaag aacttgttat ggaaaagctc   1620
aagagagaga agccaagata ctatcaagac atgtgtcgca acttcaagga ggaccaagct   1680
ctgtacaccg agaaacaggc ctttgtcgac                                    1710
```

<210> SEQ ID NO 49
<211> LENGTH: 286
<212> TYPE: PRT
<213> ORGANISM: Yarrowia lipolytica

<400> SEQUENCE: 49

```
Met Pro Ser Tyr Glu Ala Arg Ala Asn Val His Lys Ser Ala Phe Ala
1               5                   10                  15

Ala Arg Val Leu Lys Leu Val Ala Ala Lys Lys Thr Asn Leu Cys Ala
            20                  25                  30

Ser Leu Asp Val Thr Thr Thr Lys Glu Leu Ile Glu Leu Ala Asp Lys
        35                  40                  45

Val Gly Pro Tyr Val Cys Met Ile Lys Thr His Ile Asp Ile Ile Asp
    50                  55                  60

Asp Phe Thr Tyr Ala Gly Thr Val Leu Pro Leu Lys Glu Leu Ala Leu
65                  70                  75                  80

Lys His Gly Phe Phe Leu Phe Glu Asp Arg Lys Phe Ala Asp Ile Gly
                85                  90                  95

Asn Thr Val Lys His Gln Tyr Lys Asn Gly Val Tyr Arg Ile Ala Glu
            100                 105                 110

Trp Ser Asp Ile Thr Asn Ala His Gly Val Pro Gly Thr Gly Ile Ile
        115                 120                 125

Ala Gly Leu Arg Ala Gly Ala Glu Glu Thr Val Ser Glu Gln Lys Lys
    130                 135                 140

Glu Asp Val Ser Asp Tyr Glu Asn Ser Gln Tyr Lys Glu Phe Leu Val
145                 150                 155                 160

Pro Ser Pro Asn Glu Lys Leu Ala Arg Gly Leu Leu Met Leu Ala Glu
                165                 170                 175

Leu Ser Cys Lys Gly Ser Leu Ala Thr Gly Glu Tyr Ser Lys Gln Thr
            180                 185                 190

Ile Glu Leu Ala Arg Ser Asp Pro Glu Phe Val Val Gly Phe Ile Ala
        195                 200                 205

Gln Asn Arg Pro Lys Gly Asp Ser Glu Asp Trp Leu Ile Leu Thr Pro
    210                 215                 220

Gly Val Gly Leu Asp Asp Lys Gly Asp Ala Leu Gly Gln Gln Tyr Arg
225                 230                 235                 240

Thr Val Glu Asp Val Met Ser Thr Gly Thr Asp Ile Ile Ile Val Gly
                245                 250                 255

Arg Gly Leu Tyr Gly Gln Asn Arg Asp Pro Ile Glu Glu Ala Lys Arg
            260                 265                 270

Tyr Gln Lys Ala Gly Trp Glu Ala Tyr Gln Lys Ile Asn Cys
        275                 280                 285
```

<210> SEQ ID NO 50
<211> LENGTH: 35

<212> TYPE: DNA
<213> ORGANISM: Artificial Sequence
<220> FEATURE:
<223> OTHER INFORMATION: Primer KI5

<400> SEQUENCE: 50
agagcggccg catgggagaa gtgggaccca caaac                                35

<210> SEQ ID NO 51
<211> LENGTH: 38
<212> TYPE: DNA
<213> ORGANISM: Artificial Sequence
<220> FEATURE:
<223> OTHER INFORMATION: Primer KI3

<400> SEQUENCE: 51
gtggcggccg ctcaaatgtc gttattgtac caataaac                             38

<210> SEQ ID NO 52
<211> LENGTH: 1152
<212> TYPE: DNA
<213> ORGANISM: Impatients balsama

<400> SEQUENCE: 52
atgggagaag tgggacccac aaaccgaacc aaaaccaagt tggacaagca acaagaatcc       60
gaaaacaggg ttcctcacga gccacctcca ttcacactaa gtgaccttaa gaaagccatc      120
ccaccccatt gcttcgagcg ctccctcgtg aaatcattct accacgtgat tcacgacatt      180
atcatcctgt cctttttcta ctatgtcgcc gccaattaca tccccatgct accccaaaac      240
ctccgttacg ttgcatggcc aatttattgg gccatccaag ctgtgtcca acttggtata       300
ttggtcttag ccatgaatg cggccaccac gccttcagcg actaccaatg ggtagacgac       360
atggtcgggt tcgtcctcca ctcgtcccaa ttgattccct acttctcatg gaaacatagc      420
caccgtcgcc accactccaa cacggcctcc atcgagcgcg acgaggtcta cccgcccgcg      480
tacaaaaacg acctgccgtg gttcgccaaa tacctacgca accccgtcgg tcgtttcctc      540
atgattttcg gggcgctact gttcggctgg ccgtcgtacc ttctgttcaa cgcgaacggc      600
cgtctctacg accgcttcgc ttcccactac gacccgcaat ccccgatctt caacaaccgc      660
gagaggctgc aagtgatcgc gtccgacgtc gggctcgtct tcgcgtactt tgtcctgtac      720
aagatcgcgc tggccaaggg atttgtgtgg ttaatttgtg tgtatggcgt cccgtacgtg      780
atcctcaacg ggcttatcgt cttgatcacg ttcctacagc acacgcaccc gaatctgccc      840
cgttacgacc tttccgagtg ggactggctt agggagccc tgtcgactgt ggaccgcgat       900
tacgggatgt tgaataaggt gttccataac gtgacggaca cgcacttggt gcatcatttg      960
ttcacgacca tgccacatta tcgcgccaag gaggcgaccg aggtgattaa accgatattg     1020
ggagactact ataagtttga cgacactccg tttctcaaag cgttgtggaa ggacatggga     1080
aagtgtattt atgtggagtc ggacgtgcct ggcaagaaca agggagttta ttggtacaat     1140
aacgacattt ga                                                        1152

<210> SEQ ID NO 53
<211> LENGTH: 383
<212> TYPE: PRT
<213> ORGANISM: Impatients balsama

<400> SEQUENCE: 53

Met Gly Glu Val Gly Pro Thr Asn Arg Thr Lys Thr Lys Leu Asp Lys
1               5                   10                  15

Gln Gln Glu Ser Glu Asn Arg Val Pro His Glu Pro Pro Phe Thr
            20                  25                  30

Leu Ser Asp Leu Lys Lys Ala Ile Pro Pro His Cys Phe Glu Arg Ser
        35                  40                  45

Leu Val Lys Ser Phe Tyr His Val Ile His Asp Ile Ile Leu Ser
    50                  55                  60

Phe Phe Tyr Tyr Val Ala Ala Asn Tyr Ile Pro Met Leu Pro Gln Asn
65                  70                  75                  80

Leu Arg Tyr Val Ala Trp Pro Ile Tyr Trp Ala Ile Gln Gly Cys Val
                85                  90                  95

Gln Leu Gly Ile Leu Val Leu Gly His Glu Cys Gly His His Ala Phe
            100                 105                 110

Ser Asp Tyr Gln Trp Val Asp Asp Met Val Gly Phe Val Leu His Ser
        115                 120                 125

Ser Gln Leu Ile Pro Tyr Phe Ser Trp Lys His Ser His Arg Arg His
130                 135                 140

His Ser Asn Thr Ala Ser Ile Glu Arg Asp Glu Val Tyr Pro Pro Ala
145                 150                 155                 160

Tyr Lys Asn Asp Leu Pro Trp Phe Ala Lys Tyr Leu Arg Asn Pro Val
                165                 170                 175

Gly Arg Phe Leu Met Ile Phe Gly Ala Leu Leu Phe Gly Trp Pro Ser
            180                 185                 190

Tyr Leu Leu Phe Asn Ala Asn Gly Arg Leu Tyr Asp Arg Phe Ala Ser
        195                 200                 205

His Tyr Asp Pro Gln Ser Pro Ile Phe Asn Asn Arg Glu Arg Leu Gln
210                 215                 220

Val Ile Ala Ser Asp Val Gly Leu Val Phe Ala Tyr Phe Val Leu Tyr
225                 230                 235                 240

Lys Ile Ala Leu Ala Lys Gly Phe Val Trp Leu Ile Cys Val Tyr Gly
                245                 250                 255

Val Pro Tyr Val Ile Leu Asn Gly Leu Ile Val Leu Ile Thr Phe Leu
            260                 265                 270

Gln His Thr His Pro Asn Leu Pro Arg Tyr Asp Leu Ser Glu Trp Asp
        275                 280                 285

Trp Leu Arg Gly Ala Leu Ser Thr Val Asp Arg Asp Tyr Gly Met Leu
290                 295                 300

Asn Lys Val Phe His Asn Val Thr Asp Thr His Val Leu His Leu
305                 310                 315                 320

Phe Thr Thr Met Pro His Tyr Arg Ala Lys Glu Ala Thr Glu Val Ile
                325                 330                 335

Lys Pro Ile Leu Gly Asp Tyr Tyr Lys Phe Asp Thr Pro Phe Leu
            340                 345                 350

Lys Ala Leu Trp Lys Asp Met Gly Lys Cys Ile Tyr Val Glu Ser Asp
        355                 360                 365

Val Pro Gly Lys Asn Lys Gly Val Tyr Trp Tyr Asn Asn Asp Ile
370                 375                 380

<210> SEQ ID NO 54
<211> LENGTH: 34
<212> TYPE: DNA
<213> ORGANISM: Artificial Sequence
<220> FEATURE:
<223> OTHER INFORMATION: Primer KTI5

<400> SEQUENCE: 54

```
aagctcgaga ccgggttggc ggcgtatttg tgtc                                    34
```

<210> SEQ ID NO 55
<211> LENGTH: 38
<212> TYPE: DNA
<213> ORGANISM: Artificial Sequence
<220> FEATURE:
<223> OTHER INFORMATION: Primer KTI3

<400> SEQUENCE: 55

```
ggtctcgaga tctccaccgc ggacacaata tctggtca                                38
```

<210> SEQ ID NO 56
<211> LENGTH: 1756
<212> TYPE: DNA
<213> ORGANISM: Artificial Sequence
<220> FEATURE:
<223> OTHER INFORMATION: TEF/conjugase/XPR chimeric gene

<400> SEQUENCE: 56

```
gaccgggttg gcggcgtatt tgtgtcccaa aaaacagccc caattgcccc aattgacccc        60
aaattgaccc agtagcgggc ccaaccccgg cgagagcccc cttcacccca catatcaaac       120
ctcccccggt tcccacactt gccgttaagg gcgtagggta ctgcagtctg aatctacgc        180
ttgttcagac tttgtactag tttctttgtc tggccatccg ggtaacccat gccgacgca        240
aaatagacta ctgaaaattt ttttgctttg tggttgggac tttagccaag ggtataaaag       300
accaccgtcc ccgaattacc tttcctcttc ttttctctct ctccttgtca actcacaccc       360
gaaatcgtta agcatttcct tctgagtata agaatcattc aaaggatcca ctagttctag       420
agcggccgca tgggagaagt gggacccaca aaccgaacca aaaccaagtt ggacaagcaa       480
caagaatccg aaaacagggt tcctcacgag ccacctccat tcacactaag tgaccttaag       540
aaagccatcc cacccattg cttcgagcgc tccctcgtga aatcattcta ccacgtgatt       600
cacgacatta tcatcctgtc cttttttctac tatgtcgccg ccaattacat ccccatgcta       660
ccccaaaacc tccgttacgt tgcatggcca atttattggg ccatccaagg ctgtgtccaa       720
cttggtatat tggtcttagg ccatgaatgc ggccaccacg ccttcagcga ctaccaatgg       780
gtagacgaca tggtcgggtt cgtcctccac tcgtcccaat tgattcccta cttctcatgg       840
aaacatagcc accgtcgcca ccactccaac acggcctcca tcgagcgcga cgaggtctac       900
ccgcccgcgt acaaaaacga cctgccgtgg ttcgccaaat acctacgcaa ccccgtcggt       960
cgtttcctca tgattttcgg ggcgctactg ttcggctggc cgtcgtacct tctgttcaac      1020
gcgaacggcc gtctctacga ccgcttcgct tcccactacg acccgcaatc cccgatcttc      1080
aacaaccgcg agaggctgca agtgatcgcg tccgacgtcg gctcgtctt cgcgtacttt      1140
gtcctgtaca agatcgcgct ggccaaggga tttgtgtggt taatttgtgt gtatggcgtc      1200
ccgtacgtga tcctcaacgg gcttatcgtc ttgatcacgt tcctacagca cacgcacccg      1260
aatctgcccc gttacgacct ttccgagtgg gactggctta ggggagccct gtcgactgtg      1320
gaccgcgatt acgggatgtt gaataaggtg ttccataacg tgacggacac gcacttggtg      1380
catcatttgt tcacgaccat gccacattat cgcgccaagg aggcgaccga ggtgattaaa      1440
ccgatattgg gagactacta taagtttgac gacactccgt ttctcaaagc gttgtggaag      1500
gacatgggaa agtgtattta tgtggagtcg acgtgcctg gcaagaacaa gggagtttat      1560
tggtacaata acgacatttg agcggccgcc accgcggccc gagattccgg cctcttcggc      1620
```

```
cgccaagcga cccgggtgga cgtctagagg tacctagcaa ttaacagata gtttgccggt  1680
gataattctc ttaacctccc acactccttt gacataacga tttatgtaac gaaactgaaa  1740
tttgaccaga tattgt                                                   1756
```

```
<210> SEQ ID NO 57
<211> LENGTH: 383
<212> TYPE: PRT
<213> ORGANISM: Artificial Sequence
<220> FEATURE:
<223> OTHER INFORMATION: TEF/conjugase/XPR chimeric protein

<400> SEQUENCE: 57
```

```
Met Gly Glu Val Gly Pro Thr Asn Arg Thr Lys Thr Lys Leu Asp Lys
1               5                   10                  15

Gln Gln Glu Ser Glu Asn Arg Val Pro His Glu Pro Pro Pro Phe Thr
            20                  25                  30

Leu Ser Asp Leu Lys Lys Ala Ile Pro Pro His Cys Phe Glu Arg Ser
        35                  40                  45

Leu Val Lys Ser Phe Tyr His Val Ile His Asp Ile Ile Ile Leu Ser
    50                  55                  60

Phe Phe Tyr Tyr Val Ala Ala Asn Tyr Ile Pro Met Leu Pro Gln Asn
65                  70                  75                  80

Leu Arg Tyr Val Ala Trp Pro Ile Tyr Trp Ala Ile Gln Gly Cys Val
                85                  90                  95

Gln Leu Gly Ile Leu Val Leu Gly His Glu Cys Gly His His Ala Phe
            100                 105                 110

Ser Asp Tyr Gln Trp Val Asp Asp Met Val Gly Phe Val Leu His Ser
        115                 120                 125

Ser Gln Leu Ile Pro Tyr Phe Ser Trp Lys His Ser His Arg Arg His
    130                 135                 140

His Ser Asn Thr Ala Ser Ile Glu Arg Asp Glu Val Tyr Pro Pro Ala
145                 150                 155                 160

Tyr Lys Asn Asp Leu Pro Trp Phe Ala Lys Tyr Leu Arg Asn Pro Val
                165                 170                 175

Gly Arg Phe Leu Met Ile Phe Gly Ala Leu Leu Phe Gly Trp Pro Ser
            180                 185                 190

Tyr Leu Leu Phe Asn Ala Asn Gly Arg Leu Tyr Asp Arg Phe Ala Ser
        195                 200                 205

His Tyr Asp Pro Gln Ser Pro Ile Phe Asn Asn Arg Glu Arg Leu Gln
    210                 215                 220

Val Ile Ala Ser Asp Val Gly Leu Val Phe Ala Tyr Phe Val Leu Tyr
225                 230                 235                 240

Lys Ile Ala Leu Ala Lys Gly Phe Val Trp Leu Ile Cys Val Tyr Gly
                245                 250                 255

Val Pro Tyr Val Ile Leu Asn Gly Leu Ile Val Leu Ile Thr Phe Leu
            260                 265                 270

Gln His Thr His Pro Asn Leu Pro Arg Tyr Asp Leu Ser Glu Trp Asp
        275                 280                 285

Trp Leu Arg Gly Ala Leu Ser Thr Val Asp Arg Asp Tyr Gly Met Leu
    290                 295                 300

Asn Lys Val Phe His Asn Val Thr Asp Thr His Val Leu His His Leu
305                 310                 315                 320

Phe Thr Thr Met Pro His Tyr Arg Ala Lys Glu Ala Thr Glu Val Ile
                325                 330                 335
```

Lys Pro Ile Leu Gly Asp Tyr Tyr Lys Phe Asp Thr Pro Phe Leu
            340                 345                 350

Lys Ala Leu Trp Lys Asp Met Gly Lys Cys Ile Tyr Val Glu Ser Asp
        355                 360                 365

Val Pro Gly Lys Asn Lys Gly Val Tyr Trp Tyr Asn Asn Asp Ile
    370                 375                 380

<210> SEQ ID NO 58
<211> LENGTH: 32
<212> TYPE: DNA
<213> ORGANISM: Artificial Sequence
<220> FEATURE:
<223> OTHER INFORMATION: Primer KH5

<400> SEQUENCE: 58
tagagcggcc gcttaaacca tgaaaaagcc tg                                      32

<210> SEQ ID NO 59
<211> LENGTH: 33
<212> TYPE: DNA
<213> ORGANISM: Artificial Sequence
<220> FEATURE:
<223> OTHER INFORMATION: Primer KH3

<400> SEQUENCE: 59
gtggcggccg ctttaggtac ctcactattc ctt                                     33

<210> SEQ ID NO 60
<211> LENGTH: 1026
<212> TYPE: DNA
<213> ORGANISM: Escherichia coli

<400> SEQUENCE: 60
atgaaaaagc ctgaactcac cgcgacgtct gtcgagaagt ttctgatcga aaagttcgac        60
agcgtctccg acctgatgca gctctcggag ggcgaagaat ctcgtgcttt cagcttcgat       120
gtaggagggc gtggatatgt cctgcgggta aatagctgcg ccgatggttt ctacaaagat       180
cgttatgttt atcggcactt tgcatcggcc gcgctcccga ttccggaagt gcttgacatt       240
ggggaattca gcgagagcct gacctattgc atctcccgcc gtgcacaggg tgtcacgttg       300
caagacctgc tgaaaccgga ctgcccgctt gttctgcagc cggtcgcgga ggccatggat       360
gcgatcgctg cggccgatct tagccagacg agcgggttcg gcccattcgg accgcaagga       420
atcggtcaat acactacatg gcgtgatttc atatgcgcga ttgctgatcc ccatgtgtat       480
cactggcaaa ctgtgatgga cgacaccgtc agtgcgtccg tcgcgcaggc tctcgatgag       540
ctgatgcttt gggccgagga ctgccccgaa gtccggcacc tcgtgcacgc ggatttcggc       600
tccaacaatg tcctgacgga caatggccgc ataacagcgg tcattgactg gagcgaggcg       660
atgttcgggg attcccaata cgaggtcgcc aacatcttct tctggaggcc gtggttggct       720
tgtatggagc agcagacgcg ctacttcgag cggaggcatc cggagcttgc aggatcgccg       780
cggctccggg cgtatatgct ccgcattggt cttgaccaac tctatcagag cttggttgac       840
ggcaatttcg atgatgcagc ttgggcgcag ggtcgatgcg acgcaatcgt ccgatccgga       900
gccgggactg tcgggcgtac acaaatcgcc cgcagaagcg cggccgtctg gaccgatggc       960
tgtgtagaag tactcgccga tagtggaaac cgacgcccca gcactcgtcc gagggcaaag      1020
gaatag                                                                 1026

<210> SEQ ID NO 61

<211> LENGTH: 341
<212> TYPE: PRT
<213> ORGANISM: Escherichia coli

<400> SEQUENCE: 61

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
            85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340

<210> SEQ ID NO 62
<211> LENGTH: 34
<212> TYPE: DNA
<213> ORGANISM: Artificial Sequence
<220> FEATURE:
<223> OTHER INFORMATION: Primer KTH5

<400> SEQUENCE: 62
tttagatctc gagaccgggt tggcggcgta tttg                34

<210> SEQ ID NO 63
<211> LENGTH: 31
<212> TYPE: DNA
<213> ORGANISM: Artificial Sequence
<220> FEATURE:
<223> OTHER INFORMATION: Primer KTH3

<400> SEQUENCE: 63
tttagatctc caccgcggac acaatatctg g                31

<210> SEQ ID NO 64
<211> LENGTH: 1650
<212> TYPE: DNA
<213> ORGANISM: Artificial Sequence
<220> FEATURE:
<223> OTHER INFORMATION: TEF::HPT::XPR fusion

<400> SEQUENCE: 64

```
gaccgggttg gcggcgtatt tgtgtcccaa aaacagccc caattgcccc aattgacccc     60
aaattgaccc agtagcgggc ccaaccccgg cgagagcccc cttcacccca catatcaaac   120
ctcccccggt tcccacactt gccgttaagg gcgtagggta ctgcagtctg gaatctacgc   180
ttgttcagac tttgtactag tttctttgtc tggccatccg ggtaacccat gccggacgca   240
aaatagacta ctgaaaattt ttttgctttg tggttgggac tttagccaag ggtataaaag   300
accaccgtcc ccgaattacc tttcctcttc ttttctctct ctccttgtca actcacaccc   360
gaaatcgtta agcatttcct tctgagtata agaatcattc aaaggatcca ctagttctag   420
agcggccgct taaaccatga aaaagcctga actcaccgcg acgtctgtcg agaagtttct   480
gatcgaaaag ttcgacagcg tctccgacct gatgcagctc tcggagggcg aagaatctcg   540
tgctttcagc ttcgatgtag gagggcgtgg atatgtcctg cgggtaaata gctgcgccga   600
tggtttctac aaagatcgtt atgtttatcg gcactttgca tcggccgcgc tcccgattcc   660
ggaagtgctt gacattgggg aattcagcga gagcctgacc tattgcatct cccgccgtgc   720
acagggtgtc acgttgcaag acctgcctga accgaactgc ccgctgttc tgcagccggt   780
cgcggaggcc atggatgcga tcgctgcggc cgatcttagc cagacgagcg ggttcggccc   840
attcggaccg caaggaatcg gtcaatacac tacatggcgt gatttcatat gcgcgattgc   900
tgatccccat gtgtatcact ggcaaactgt gatggacgac accgtcagtg cgtccgtcgc   960
gcaggctctc gatgagctga tgctttgggc cgaggactgc cccgaagtcc ggcacctcgt  1020
gcacgcggat tcggctcca acaatgtcct gacgacaat ggccgcataa cagcggtcat  1080
tgactggagc gaggcgatgt tcgggattc ccaatacgag gtcgccaaca tcttcttctg  1140
gaggccgtgg ttggcttgta tggagcagca gacgcgctac ttcgagcgga ggcatccgga  1200
gcttgcagga tcgccgcggc tccgggcgta tatgctccgc attggtcttg accaactcta  1260
tcagagcttg gttgacggca atttcgatga tgcagcttgg gcgcagggtc gatgcgacgc  1320
aatcgtccga tccggagccg ggactgtcgg cgtacacaa atcgcccgca gaagcgcggc  1380
cgtctggacc gatggctgtg tagaagtact cgccgatagt ggaaaccgac gccccagcac  1440
tcgtccgagg gcaaaggaat agtgaggtac ctaaagcggc cgccaccgcg gcccgagatt  1500
ccggcctctt cggccgccaa gcgacccggg tggacgtcta gaggtaccta gcaattaaca  1560
```

```
gatagtttgc cggtgataat tctcttaacc tcccacactc ctttgacata acgatttatg    1620
taacgaaact gaaatttgac cagatattgt                                     1650
```

<210> SEQ ID NO 65
<211> LENGTH: 341
<212> TYPE: PRT
<213> ORGANISM: Artificial Sequence
<220> FEATURE:
<223> OTHER INFORMATION: TEF::HPT::XPR fusion

<400> SEQUENCE: 65

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340
```

<210> SEQ ID NO 66
<211> LENGTH: 401
<212> TYPE: DNA
<213> ORGANISM: Yarrowia lipolytica

<400> SEQUENCE: 66

```
cgagtatctg tctgactcgt cattgccgcc tttggagtac gactccaact atgagtgtgc      60
ttggatcact ttgacgatac attcttcgtt ggaggctgtg ggtctgacag ctgcgttttc     120
ggcgcggttg gccgacaaca atatcagctg caacgtcatt gctggctttc atcatgatca     180
cattttgtc  ggcaaaggcg acgcccagag agccattgac gttctttcta atttggaccg     240
atagccgtat agtccagtct atctataagt tcaactaact cgtaactatt accataacat     300
atacttcact gccccagata aggttccgat aaaaagttct gcagactaaa tttatttcag     360
tctcctcttc accaccaaaa tgccctccta cgaagctcga g                         401
```

<210> SEQ ID NO 67
<211> LENGTH: 568
<212> TYPE: DNA
<213> ORGANISM: Yarrowia lipolytica

<400> SEQUENCE: 67

```
atcataattg tcggccgagg tctgtacggc cagaaccgag atcctattga ggaggccaag      60
cgataccaga aggctggctg ggaggcttac cagaagatta actgttagag gttagactat     120
ggatatgtca tttaactgtg tatatagaga gcgtgcaagt atggagcgct tgttcagctt     180
gtatgatggt cagacgacct gtctgatcga gtatgtatga tactgcacaa cctgtgtatc     240
cgcatgatct gtccaatggg gcatgttgtt gtgtttctcg atacggagat gctgggtaca     300
agtagctaat acgattgaac tacttatact tatatgaggc ttgaagaaag ctgacttgtg     360
tatgacttat tctcaactac atccccagtc acaataccac cactgcacta ccactacacc     420
aaaaccatga tcaaaccacc catggacttc ctggaggcag aagaacttgt tatggaaaag     480
ctcaagagag agaagccaag atactatcaa gacatgtgtc gcaacttcaa ggaggaccaa     540
gctctgtaca ccgagaaaca ggcctttg                                        568
```

<210> SEQ ID NO 68
<211> LENGTH: 36
<212> TYPE: DNA
<213> ORGANISM: Artificial Sequence
<220> FEATURE:
<223> OTHER INFORMATION: Primer YL63

<400> SEQUENCE: 68

```
ttatgatatc gaattaatta acctgcagcc cggggg                                36
```

<210> SEQ ID NO 69
<211> LENGTH: 36
<212> TYPE: DNA
<213> ORGANISM: Artificial Sequence
<220> FEATURE:
<223> OTHER INFORMATION: Primer YL64

<400> SEQUENCE: 69

```
cccccgggct gcaggttaat taattcgata tcataa                                36
```

<210> SEQ ID NO 70
<211> LENGTH: 33
<212> TYPE: DNA

```
<213> ORGANISM: Artificial Sequence
<220> FEATURE:
<223> OTHER INFORMATION: Primer YL65

<400> SEQUENCE: 70
tacgccgcca acccgtacgt ctcgagcttc gta                              33

<210> SEQ ID NO 71
<211> LENGTH: 33
<212> TYPE: DNA
<213> ORGANISM: Artificial Sequence
<220> FEATURE:
<223> OTHER INFORMATION: Primer YL66

<400> SEQUENCE: 71
tacgaagctc gagacgtacg ggttggcggc gta                              33

<210> SEQ ID NO 72
<211> LENGTH: 30
<212> TYPE: DNA
<213> ORGANISM: Artificial Sequence
<220> FEATURE:
<223> OTHER INFORMATION: Primer YL11

<400> SEQUENCE: 72
ttttccatgg gaacggacca aggaaaaacc                                  30

<210> SEQ ID NO 73
<211> LENGTH: 30
<212> TYPE: DNA
<213> ORGANISM: Artificial Sequence
<220> FEATURE:
<223> OTHER INFORMATION: Primer YL12

<400> SEQUENCE: 73
tttgcggccg cctactcttc cttgggacgg                                  30

<210> SEQ ID NO 74
<211> LENGTH: 33
<212> TYPE: DNA
<213> ORGANISM: Artificial Sequence
<220> FEATURE:
<223> OTHER INFORMATION: Primer YL81

<400> SEQUENCE: 74
gttatccgct cacaagcttc cacacaacgt acg                              33

<210> SEQ ID NO 75
<211> LENGTH: 33
<212> TYPE: DNA
<213> ORGANISM: Artificial Sequence
<220> FEATURE:
<223> OTHER INFORMATION: Primer YL82

<400> SEQUENCE: 75
cgtacgttgt gtggaagctt gtgagcggat aac                              33

<210> SEQ ID NO 76
<211> LENGTH: 33
<212> TYPE: DNA
<213> ORGANISM: Artificial Sequence
<220> FEATURE:
<223> OTHER INFORMATION: Primer YL83

<400> SEQUENCE: 76
atttgaatcg aatcgatgag cctaaaatga acc                              33
```

<210> SEQ ID NO 77
<211> LENGTH: 33
<212> TYPE: DNA
<213> ORGANISM: Artificial Sequence
<220> FEATURE:
<223> OTHER INFORMATION: Primer YL84

<400> SEQUENCE: 77
ggttcatttt aggctcatcg attcgattca aat                           33

<210> SEQ ID NO 78
<211> LENGTH: 38
<212> TYPE: DNA
<213> ORGANISM: Artificial Sequence
<220> FEATURE:
<223> OTHER INFORMATION: Primer YL105

<400> SEQUENCE: 78
ccaagcacta acctaccgtt taaacaccac taaaaccc                      38

<210> SEQ ID NO 79
<211> LENGTH: 38
<212> TYPE: DNA
<213> ORGANISM: Artificial Sequence
<220> FEATURE:
<223> OTHER INFORMATION: Primer YL106

<400> SEQUENCE: 79
gggttttagt ggtgtttaaa cggtaggtta gtgcttgg                      38

<210> SEQ ID NO 80
<211> LENGTH: 36
<212> TYPE: DNA
<213> ORGANISM: Artificial Sequence
<220> FEATURE:
<223> OTHER INFORMATION: Primer YL119

<400> SEQUENCE: 80
cgggaaacct gtcgtggcgc gccagctgca ttaatg                        36

<210> SEQ ID NO 81
<211> LENGTH: 36
<212> TYPE: DNA
<213> ORGANISM: Artificial Sequence
<220> FEATURE:
<223> OTHER INFORMATION: Primer YL120

<400> SEQUENCE: 81
cattaatgca gctggcgcgc cacgacaggt ttcccg                        36

<210> SEQ ID NO 82
<211> LENGTH: 34
<212> TYPE: DNA
<213> ORGANISM: Artificial Sequence
<220> FEATURE:
<223> OTHER INFORMATION: Primer YL121

<400> SEQUENCE: 82
tttggcgcgc ctatcacatc acgctctcat caag                          34

<210> SEQ ID NO 83
<211> LENGTH: 34
<212> TYPE: DNA
<213> ORGANISM: Artificial Sequence
<220> FEATURE:

<223> OTHER INFORMATION: Primer YL122

<400> SEQUENCE: 83
tttcgtacga accaccaccg tcagcccttc tgac          34

<210> SEQ ID NO 84
<211> LENGTH: 440
<212> TYPE: DNA
<213> ORGANISM: Yarrowia lipolytica

<400> SEQUENCE: 84
aaccaccacc gtcagccctt ctgactcacg tattgtagcc accgacacag gcaacagtcc     60
gtggatagca gaatatgtct tgtcggtcca tttctcacca actttaggcg tcaagtgaat    120
gttgcagaag aagtatgtgc cttcattgag aatcggtgtt gctgatttca ataaagtctt    180
gagatcagtt tggccagtca tgttgtgggg ggtaattgga ttgagttatc gcctacagtc    240
tgtacaggta tactcgctgc ccactttata cttttttgatt ccgctgcact tgaagcaatg   300
tcgtttacca aaagtgagaa tgctccacag aacacacccc agggtatggt tgagcaaaaa    360
ataaacactc cgatacgggg aatcgaaccc cggtctccac ggttctcaag aagtattctt    420
gatgagagcg tgatgtgata                                                 440

<210> SEQ ID NO 85
<211> LENGTH: 35
<212> TYPE: DNA
<213> ORGANISM: Artificial Sequence
<220> FEATURE:
<223> OTHER INFORMATION: Primer YL114

<400> SEQUENCE: 85
tgatagtatc ttggcgcgcc ttctctctct tgagc          35

<210> SEQ ID NO 86
<211> LENGTH: 35
<212> TYPE: DNA
<213> ORGANISM: Artificial Sequence
<220> FEATURE:
<223> OTHER INFORMATION: Primer YL115

<400> SEQUENCE: 86
gctcaagaga gagaaggcgc gccaagatac tatca          35

<210> SEQ ID NO 87
<211> LENGTH: 5218
<212> TYPE: DNA
<213> ORGANISM: Artificial Sequence
<220> FEATURE:
<223> OTHER INFORMATION: 5218 bp fragment for integration and expression
      of the delta-5 desaturase gene

<400> SEQUENCE: 87
tatcacatca cgctctcatc aagaatactt cttgagaacc gtggagaccg gggttcgatt     60
ccccgtatcg gagtgtttat tttttgctca accatacccct ggggtgtgtt ctgtggagca   120
ttctcacttt tggtaaacga cattgcttca agtgcagcgg aatcaaaaag tataaagtgg    180
gcagcgagta tacctgtaca gactgtaggc gataactcaa tccaattacc ccccacaaca    240
tgactggcca aactgatctc aagactttat tgaaatcagc aacaccgatt ctcaatgaag    300
gcacatactt cttctgcaac attcacttga cgcctaaagt tggtgagaaa tggaccgaca    360
agacatattc tgctatccac ggactgttgc ctgtgtcggt ggctacaata cgtgagtcag    420

```
aagggctgac ggtggtggtt cgtacgttgt gtggaagctt gtgagcggat aacaatttca      480
cacaggaaac agctatgacc atgattacgc caagctcgaa attaaccctc actaaaggga      540
acaaaagctg gagctccacc gcggacacaa tatctggtca aatttcagtt tcgttacata      600
aatcgttatg tcaaaggagt gtgggaggtt aagagaatta tcaccggcaa actatctgtt      660
aattgctagg tacctctaga cgtccacccg ggtcgcttgg cggccgaaga ggccggaatc      720
tcgggccgcg gtggcggccg cctactcttc cttgggacgg agtccaagaa cacgcaagtg      780
ctccaaatgt gaagcaaatg cttgccaaaa cgtatccttg acaaggtatg gaaccttgta      840
ctcgctgcag gtgttcttga tgatggccag aatatcggga taatggtgct gcgacacgtt      900
ggggaacaga tggtgcacag ccggtagttc aagctgccag tgatgctggt ccagaggtgc      960
gaatcgtgtg cgtaatcctg cgtagtctcg acctgcatag ctgcccagtc cttttggatg     1020
atcccgttct cgtcaggcaa cggccactga acttcctcaa caacgtggtt cgcctggaag     1080
gtcagcgcca gccagtaaga cgacaccatg tccgcgaccg tgaacaagag cagcaccttg     1140
cccaggggca gatactgcag gggaacaatc aggcgatacc agacaaagaa agccttgccg     1200
ccccagaaca tcacagtgtg ccatgtcgag atgggattga cacgaatagc gtcattggtc     1260
ttgacaaagt acaaaatgtt gatgtcctga atgcgcacct tgaacgccag cagtccgtac     1320
aggaaaggaa caaacatgtg ctggttgatg tggttgacaa accacttttg gttgggcttg     1380
atacgacgaa catcgggctc agacgtcgac acgtcggat ctgctccagc aatgttggtg     1440
taggggtgat ggccgagcat atgttggtac atccacacca ggtacgatgc tccgttgaaa     1500
aagtcgtgcg tggctcccag aatcttccag acagtgggg tgtgggtcac tgaaaagtga     1560
gacgcatcat gaagagggtt gagtccgact tgtgcgcacg caaatcccat gatgattgca     1620
aacaccacct gaagccatgt gcgttcgaca acgaaaggca caaagagctg cgcgtagtag     1680
gaagcgatca aggatccaaa gataagagcg tatcgtcccc agatctctgg tctattcttg     1740
ggatcaatgt tccgatccgt aaagtagccc tcgactctcg tcttgatggt tttgtggaac     1800
accgttggct ccgggaagat gggcagctca ttcgagacca gtgtaccgac atagtacttc     1860
ttcataatgg catctgcagc cccaaacgcg tgatacatct caaagaccgg agtaacatct     1920
cggccagctc cgagcaggag agtgtccact ccaccaggat ggcggctcaa gaactttgtg     1980
acatcgtaca ccctgccgcg gatggccaag agtaggtcgt ccttggtgtt atgggccgcc     2040
agctcttccc aggtgaaggt ttttccttgg tccgttccca tggtgaatga ttcttatact     2100
cagaaggaaa tgcttaacga tttcgggtgt gagttgacaa ggagagagag aaaagaagag     2160
gaaaggtaat tcggggacgg tggtctttta tacccttggc taaagtccca accacaaagc     2220
aaaaaaattt tcagtagtct attttgcgtc cggcatgggt tacccggatg ccagacaaa     2280
gaaactagta caaagtctga acaagcgtag attccagact gcagtaccct acgcccttaa     2340
cggcaagtgt gggaaccggg ggaggtttga tatgtgggt gaaggggct ctcgccgggg      2400
ttgggcccgc tactgggtca atttgggtc aattggggca attggggctg ttttttggga      2460
cacaaatacg ccgccaaccc ggtctctcct gaattctgca gatgggctgc aggaattccg     2520
tcgtcgcctg agtcgacatc atttatttac cagttgccca caaaccttg acgatctcgt      2580
atgtcccctc cgacatactc ccggccggct ggggtacgtt cgatagcgct atcggcatcg     2640
acaaggtttg ggtccctagc cgataccgca ctacctgagt cacaatcttc ggaggtttag     2700
tcttccacat agcacgggca aaagtgcgta tatatacaag agcgtttgcc agccacagat     2760
tttcactcca cacaccacat cacacataca accacacaca tccacaatgg aacccgaaac     2820
```

```
taagaagacc aagactgact ccaagaagat tgttcttctc ggcggcgact tctgtggccc   2880
cgaggtgatt gccgaggccg tcaaggtgct caagtctgtt gctgaggcct ccggcaccga   2940
gtttgtgttt gaggaccgac tcattggagg agctgccatt gagaaggagg gcgagcccat   3000
caccgacgct actctcgaca tctgccgaaa ggctgactct attatgctcg gtgctgtcgg   3060
aggcgctgcc aacaccgtat ggaccactcc cgacggacga accgacgtgc gacccgagca   3120
gggtctcctc aagctgcgaa aggacctgaa cctgtacgcc aacctgcgac cctgccagct   3180
gctgtcgccc aagctcgccg atctctcccc catccgaaac gttgagggca ccgacttcat   3240
cattgtccga gagctcgtcg gaggtatcta ctttggagag cgaaggagg atgacggatc   3300 tggcgtcgct tccgacaccg agacctactc cgttcctgag gttgagcgaa ttgcccgaat   3360
ggccgccttc ctggcccttc agcacaaccc ccctcttccc gtgtggtctc ttgacaaggc   3420
caacgtgctg gcctcctctc gactttggcg aaagactgtc actcgagtcc tcaaggacga   3480
attcccccag ctcgagctca accaccagct gatcgactcg gccgccatga tcctcatcaa   3540
gcagccctcc aagatgaatg gtatcatcat caccaccaac atgtttggcg atatcatctc   3600
cgacgaggcc tccgtcatcc ccggttctct gggtctgctg ccctccgcct ctctggcttc   3660
tctgcccgac accaacgagg cgttcggtct gtacgagccc tgtcacggat ctgcccccga   3720
tctcggcaag cagaaggtca accccattgc caccattctg tctgccgcca tgatgctcaa   3780
gttctctctt aacatgaagc ccgccggtga cgctgttgag gctgccgtca aggagtccgt   3840
cgaggctggt atcactaccg ccgatatcgg aggctcttcc tccacctccg aggtcggaga   3900
cttgttgcca acaaggtcaa ggagctgctc aagaaggagt aagtcgtttc tacgacgcat   3960
tgatggaagg agcaaactga cgcgcctgcg ggttggtcta ccggcagggt ccgctagtgt   4020
ataagactct ataaaaaggg ccctgccctg ctaatgaaat gatgatttat aatttaccgg   4080
tgtagcaacc ttgactagaa gaagcagatt gggtgtgttt gtagtggagg acagtggtac   4140
gttttggaaa cagtcttctt gaaagtgtct tgtctacagt atattcactc ataacctcaa   4200
tagccaaggg tgtagtcggt ttattaaagg aagggagttg tggctgatgt ggatagatat   4260
ctttaagctg gcgactgcac ccaacgagtg tggtggtagc ttgttactgt atattcggta   4320
agatatattt tgtgggtttt tagtggtgtt taaacggtag gttagtgctt ggtatatgag   4380
ttgtaggcat gacaatttgg aaaggggtgg actttgggaa tattgtggga tttcaatacc   4440
ttagtttgta cagggtaatt gttacaaatg atacaaagaa ctgtatttct tttcatttgt   4500
tttaattggt tgtatatcaa gtccgttaga cgagctcagt gccttggctt ttggcactgt   4560
atttcatttt tagaggtaca ctacattcag tgaggtatgg taaggttgag ggcataatga   4620
aggcaccttg tactgacagt cacagacctc tcaccgagaa ttttatgaga tatactcggg   4680
ttcattttag gctcatcgat tcgattcaaa ttaattaatt cgatatcata attgtcggcc   4740
gaggtctgta cggccagaac cgagatccta ttgaggaggc caagcgatac cagaaggctg   4800
gctgggaggc ttaccagaag attaactgtt agaggttaga ctatggatat gtcatttaac   4860
tgtgtatata gagagcgtgc aagtatggag cgcttgttca gcttgtatga tggtcagacg   4920
acctgtctga tcgagtatgt atgatactgc acaacctgtg tatccgcatg atctgtccaa   4980
tggggcatgt tgttgtgttt ctcgatacgg agatgctggg tacaagtagc taatacgatt   5040
gaactactta tacttatatg aggcttgaag aaagctgact tgtgtatgac ttattctcaa   5100
ctacatcccc agtcacaata ccaccactgc actaccacta caccaaaacc atgatcaaac   5160
```
cacccatgga cttcctggag gcagaagaac ttgttatgga aaagctcaag agagagaa    5218

<210> SEQ ID NO 88
<211> LENGTH: 33
<212> TYPE: DNA
<213> ORGANISM: Artificial Sequence
<220> FEATURE:
<223> OTHER INFORMATION: Primer YL61

<400> SEQUENCE: 88
acaattccac acaacgtacg agccggaagc ata    33

<210> SEQ ID NO 89
<211> LENGTH: 33
<212> TYPE: DNA
<213> ORGANISM: Artificial Sequence
<220> FEATURE:
<223> OTHER INFORMATION: Primer YL62

<400> SEQUENCE: 89
tatgcttccg gctcgtacgt tgtgtggaat tgt    33

<210> SEQ ID NO 90
<211> LENGTH: 33
<212> TYPE: DNA
<213> ORGANISM: Artificial Sequence
<220> FEATURE:
<223> OTHER INFORMATION: Primer YL69

<400> SEQUENCE: 90
agcccatctg cagaagcttc aggagagacc ggg    33

<210> SEQ ID NO 91
<211> LENGTH: 33
<212> TYPE: DNA
<213> ORGANISM: Artificial Sequence
<220> FEATURE:
<223> OTHER INFORMATION: Primer YL70

<400> SEQUENCE: 91
cccggtctct cctgaagctt ctgcagatgg gct    33

<210> SEQ ID NO 92
<211> LENGTH: 33
<212> TYPE: DNA
<213> ORGANISM: Artificial Sequence
<220> FEATURE:
<223> OTHER INFORMATION: Primer YL77

<400> SEQUENCE: 92
tagtgagggt taattaatcg agcttggcgt aat    33

<210> SEQ ID NO 93
<211> LENGTH: 33
<212> TYPE: DNA
<213> ORGANISM: Artificial Sequence
<220> FEATURE:
<223> OTHER INFORMATION: Primer YL78

<400> SEQUENCE: 93
attacgccaa gctcgattaa ttaaccctca cta    33

<210> SEQ ID NO 94
<211> LENGTH: 34
<212> TYPE: DNA
<213> ORGANISM: Artificial Sequence

```
<220> FEATURE:
<223> OTHER INFORMATION: Primer YL79A

<400> SEQUENCE: 94
attcctgcag cccatcgatg cagaattcag gaga                                    34

<210> SEQ ID NO 95
<211> LENGTH: 34
<212> TYPE: DNA
<213> ORGANISM: Artificial Sequence
<220> FEATURE:
<223> OTHER INFORMATION: Primer YL80A

<400> SEQUENCE: 95
tctcctgaat tctgcatcga tgggctgcag gaat                                    34

<210> SEQ ID NO 96
<211> LENGTH: 8894
<212> TYPE: DNA
<213> ORGANISM: Artificial Sequence
<220> FEATURE:
<223> OTHER INFORMATION: 8894 bp fragment for integration and expression
      of the delta-6 and delta-5 desaturase genes and the elongase gene

<400> SEQUENCE: 96
tatcacatca cgctctcatc aagaatactt cttgagaacc gtggagaccg gggttcgatt         60
ccccgtatcg gagtgtttat tttttgctca accatacccc ggggtgtgtt ctgtggagca        120
ttctcacttt tggtaaacga cattgcttca agtgcagcgg aatcaaaaag tataaagtgg        180
gcagcgagta tacctgtaca gactgtaggc gataactcaa tccaattacc ccccacaaca        240
tgactggcca aactgatctc aagactttat tgaaatcagc aacaccgatt ctcaatgaag        300
gcacatactt cttctgcaac attcacttga cgcctaaagt tggtgagaaa tggaccgaca        360
agacatattc tgctatccac ggactgttgc ctgtgtcggt ggctacaata cgtgagtcag        420
aagggctgac ggtggtggtt cgtacgttgt gtggaattgt gagcggataa caatttcaca        480
caggaaacag ctatgaccat gattacgcca agctcgaaat taaccctcac taaagggaac        540
aaaagctgga gctccaccgc ggacacaata tctggtcaaa tttcagtttc gttacataaa        600
tcgttatgtc aaaggagtgt gggaggttaa gagaattatc accggcaaac tatctgttaa        660
ttgctaggta cctctagacg tccacccggg tcgcttggcg gccgaagagg ccggaatctc        720
gggccgcggt ggcggccgct tactgcaact tccttgcctt ctccttggca gcgtcggcct        780
tggcctgctt ggccaacttg gcgttctttc tgtaaaagtt gtagaagaga ccgagcatgg        840
tccacatgta gaaccaaagc agagccgtga tgaagaaggg gtatccgggg cggccaagga        900
ccttcatggc gtacatgtcc caggaagact ggaccgacat catgcagaac tgtgtcatct        960
gcgagcgcgt gatgtagaac ttgatgaacg acacctgctt gaagcccaag gccgacaaga       1020
agtagtagcc gtacatgatc acatggatga acgagttcaa cgcagcagag aagtaggctt       1080
caccgttggg tgcaacaaag gtgaccaacc accagatggt gaagatggag ctgtggtggt       1140
aaacgtgcaa gaaggagatc tggcggttgt tcttcttgag gaccatgatc atggtgtcga       1200
caaactccat gatcttggag aagtagaaga gccagatcat cttggccata ggaagaccct       1260
tgaaggtatg atcagcagcg ttctcaaaca gtccatagtt ggcctgataa gcctcgtaca       1320
ggatcccacc gcacatgtag gcgctgatcg agaccagaca aaagttgtgc aggagcgaaa       1380
acgtcttgac ctcgaaccgc tcaaagttct tcatgatctg catgcccaca agaccgtga       1440 ccaaataagc gagcacgatc aacagcacgt ggaacgggtt catcaacggc agctcacggg       1500
```

```
ccaaaggcga ctccaccgcg accaggaacc cacgcgtgtg atggacaatc gtggggatgt    1560
acttctcggc ctgggccacc agcgcggcct cgagaggatc gacatagggc gcggcccgga    1620
caccgatagc ggtggcaagg tccataaaca gatcttgcgg catctttgat gggaggaatg    1680
gcgcaatcga ctccatgcgg ccgctctaga actagtggat cctttgaatg attcttatac    1740
tcagaaggaa atgcttaacg atttcgggtg tgagttgaca aggagagaga gaaaagaaga    1800
ggaaaggtaa ttcggggacg gtggtctttt atacccttgg ctaaagtccc aaccacaaag    1860
caaaaaaatt ttcagtagtc tattttgcgt ccggcatggg ttacccggat ggccagacaa    1920
agaaactagt acaaagtctg aacaagcgta gattccagac tgcagtaccc tacgccctta    1980
acggcaagtg tgggaaccgg gggaggtttg atatgtgggg tgaaggggc tctcgccggg     2040 gttgggcccg ctactgggtc aatttggggt caattggggc aattgggct gttttttggg     2100 acacaaatac gccgccaacc cggtctctcc tgaagcttgt gagcggataa caatttcaca    2160
caggaaacag ctatgaccat gattacgcca agctcgaaat taaccctcac taaagggaac    2220
aaaagctgga gctccaccgc ggacacaata tctggtcaaa tttcagtttc gttacataaa    2280
tcgttatgtc aaaggagtgt gggaggttaa gagaattatc accggcaaac tatctgttaa    2340
ttgctaggta cctctagacg tccacccggg tcgcttggcg gccgaagagg ccggaatctc    2400 gggccgcgt ggcggccgcc tactcttcct tgggacggag tccaagaaca cgcaagtgct     2460
ccaaatgtga agcaaatgct tgccaaaacg tatccttgac aaggtatgga accttgtact    2520
cgctgcaggt gttcttgatg atggccagaa tatcgggata atggtgctgc gacacgttgg    2580
ggaacagatg gtgcacagcc tggtagttca agctgccagt gatgctggtc cagaggtgcg    2640
aatcgtgtgc gtaatcctgc gtagtctcga cctgcatagc tgcccagtcc ttttggatga    2700
tcccgttctc gtcaggcaac ggccactgaa cttcctcaac aacgtggttc gcctggaagg    2760
tcagcgccag ccagtaagac gacaccatgt ccgcgaccgt gaacaagagc agcaccttgc    2820
ccaggggcag atactgcagg ggaacaatca ggcgatacca gacaaagaaa gccttgccgc    2880
cccagaacat cacagtgtgc catgtcgaga tgggattgac acgaatagcg tcattggtct    2940
tgacaaagta caaaatgttg atgtcctgaa tgcgcacctt gaacgccagc agtccgtaca    3000
ggaaaggaac aaacatgtgc tggttgatgt ggttgacaaa ccacttttgg ttgggcttga    3060
tacgacgaac atcgggctca gacgtcgaca cgtcgggatc tgctccagca atgttggtgt    3120
aggggtgatg gccgagcata tgttggtaca tccacaccag gtacgatgct ccgttgaaaa    3180
agtcgtgcgt ggctcccaga atcttccaga cagtggggtt gtgggtcact gaaaagtgag    3240
acgcatcatg aagagggttg agtccgactt gtgcgcacgc aaatcccatg atgattgcaa    3300
acaccacctg aagccatgtg cgttcgacaa cgaaaggcac aaagagctgc gcgtagtagg    3360
aagcgatcaa ggatccaaag ataagagcgt atcgtcccca gatctctggt ctattcttgg    3420
gatcaatgtt ccgatccgta aagtagccct cgactctcgt cttgatggtt ttgtggaaca    3480
ccgttggctc cgggaagatg ggcagctcat tcgagaccag tgtaccgaca tagtacttct    3540
tcataatggc atctgcagcc ccaaacgcgt gatacatctc aaagaccgga gtaacatctc    3600
ggccagctcc gagcaggaga gtgtccactc caccaggatg gcggctcaag aactttgtga    3660
catcgtacac cctgccgcgg atggccaaga gtaggtcgtc cttggtgtta tgggccgcca    3720
gctcttccca ggtgaaggtt tttccttggt ccgttcccat ggtgaatgat tcttatactc    3780
agaaggaaat gcttaacgat ttcgggtgtg agttgacaag gagagagaga aaagaagagg    3840
```

```
aaaggtaatt cggggacggt ggtcttttat acccttggct aaagtcccaa ccacaaagca    3900
aaaaaatttt cagtagtcta ttttgcgtcc ggcatgggtt acccggatgg ccagacaaag    3960
aaactagtac aaagtctgaa caagcgtaga ttccagactg cagtaccota cgcccttaac    4020 ggcaagtgtg ggaaccgggg gaggtttgat atgtggggtg aaggggggctc tcgccggggt    4080 tgggcccgct actgggtcaa tttggggtca attggggcaa ttggggctgt tttttgggac    4140
acaaatacgc cgccaacccg gtctctcctg aattctgcag atgggctgca ggaattccgt    4200
cgtcgcctga gtcgacatca tttatttacc agttggccac aaaccottga cgatctcgta    4260 tgtcccctcc gacatactcc cggccggctg gggtacgttc gatagcgcta tcggcatcga    4320
caaggtttgg gtccctagcc gataccgcac tacctgagtc acaatcttcg gaggtttagt    4380
cttccacata gcacgggcaa aagtgcgtat atatacaaga gcgtttgcca gccacagatt    4440
ttcactccac acaccacatc acacatacaa ccacacacat ccacaatgga acccgaaact    4500
aagaagacca agactgactc caagaagatt gttcttctcg gcggcgactt ctgtggcccc    4560
gaggtgattg ccgaggccgt caaggtgctc aagtctgttg ctgaggcctc cggcaccgag    4620
tttgtgtttg aggaccgact cattggagga gctgccattg agaaggaggg cgagcccatc    4680
accgacgcta ctctcgacat ctgccgaaag gctgactcta ttatgctcgg tgctgtcgga    4740
ggcgctgcca acaccgtatg gaccactccc gacggacgaa ccgacgtgcg acccgagcag    4800
ggtctcctca agctgcgaaa ggacctgaac ctgtacgcca acctgcgacc ctgccagctg    4860
ctgtcgccca agctcgccga tctctccccc atccgaaacg ttgagggcac cgacttcatc    4920
attgtccgag agctcgtcgg aggtatctac tttggagagc gaaaggagga tgacggatct    4980
ggcgtcgctt ccgacaccga gacctactcc gttcctgagg ttgagcgaat tgcccgaatg    5040
gccgccttcc tggcccttca gcacaacccc cctcttcccg tgtggtctct tgacaaggcc    5100
aacgtgctgg cctcctctcg actttggcga aagactgtca ctcgagtcct caaggacgaa    5160
ttcccccagc tcgagctcaa ccaccagctg atcgactcgg ccgccatgat cctcatcaag    5220
cagccctcca agatgaatgg tatcatcatc accaccaaca tgtttggcga tatcatctcc    5280
gacgaggcct ccgtcatccc cggttctctg ggtctgctgc cctccgcctc tctggcttct    5340
ctgcccgaca ccaacgaggc gttcggtctg tacgagccct gtcacggatc tgcccccgat    5400
ctcggcaagc agaaggtcaa ccccattgcc accattctgt ctgccgccat gatgctcaag    5460
ttctctctta acatgaagcc cgccggtgac gctgttgagg ctgccgtcaa ggagtccgtc    5520
gaggctggta tcactaccgc cgatatcgga ggctcttcct ccacctccga ggtcggagac    5580
ttgttgccaa caaggtcaag gagctgctca agaaggagta agtcgtttct acgacgcatt    5640
gatggaagga gcaaactgac gcgcctgcgg gttggtctac cggcagggtc cgctagtgta    5700
taagactcta taaaagggc cctgccctgc taatgaaatg atgatttata atttaccggt    5760
gtagcaacct tgactagaag aagcagattg ggtgtgtttg tagtggagga cagtggtacg    5820
ttttggaaac agtcttcttg aaagtgtctt gtctacagta tattcactca taacctcaat    5880
agccaagggt gtagtcggtt tattaaagga agggagttgt ggctgatgtg gatagatatc    5940
tttaagctgg cgactgcacc caacgagtgt ggtggtagct tgttactgta tattcggtaa    6000
gatatatttt gtggggtttt agtggtgttt aaacggtagg ttagtgcttg gtatatgagt    6060
tgtaggcatg acaatttgga aagggtggga ctttgggaat attgtgggat ttcaatacct    6120 tagttttgtac agggtaattg ttacaaatga tacaaagaac tgtatttctt ttcatttgtt    6180
ttaattggtt gtatatcaag tccgttagac gagctcagtg ccttggcttt tggcactgta    6240
```

```
tttcattttt agaggtacac tacattcagt gaggtatggt aaggttgagg cataatgaa    6300 ggcaccttgt actgacagtc acagacctct caccgagaat tttatgagat atactcgggt    6360
tcattttagg ctcatcgatg cagaattcag gagagaccgg gttggcggcg tatttgtgtc    6420
ccaaaaaaca gccccaattg ccccaattga ccccaaattg acccagtagc gggcccaacc    6480
ccggcgagag cccccttcac cccacatatc aaacctcccc cggttccac acttgccgtt     6540 aagggcgtag ggtactgcag tctggaatct acgcttgttc agactttgta ctagtttctt    6600
tgtctggcca tccgggtaac ccatgccgga cgcaaaatag actactgaaa atttttttgc    6660
tttgtggttg ggactttagc caagggtata aagaccacc gtccccgaat tacctttcct     6720
cttcttttct ctctctcctt gtcaactcac acccgaaatc gttaagcatt tcttctgag     6780 tataagaatc attcaccatg gctgctgctc ccagtgtgag gacgtttact cgggccgagg    6840
ttttgaatgc cgaggctctg aatgagggca agaaggatgc cgaggcaccc ttcttgatga    6900
tcatcgacaa caaggtgtac gatgtccgcg agttcgtccc tgatcatccc ggtggaagtg    6960
tgattctcac gcacgttggc aaggacggca ctgacgtctt tgacactttt caccccgagg    7020
ctgcttggga gactcttgcc aacttttacg ttggtgatat tgacgagagc gaccgcgata    7080
tcaagaatga tgactttgcg gccgaggtcc gcaagctgcg taccttgttc cagtctcttg    7140
gttactacga ttcttccaag gcatactacg ccttcaaggt ctcgttcaac ctctgcatct    7200
ggggtttgtc gacggtcatt gtggccaagt ggggccagac ctcgaccctc gccaacgtgc    7260
tctcggctgc gcttttgggt ctgttctggc agcagtgcgg atggttggct cacgactttt    7320
tgcatcacca ggtcttccag gaccgtttct ggggtgatct tttcggcgcc ttcttgggag    7380
gtgtctgcca gggcttctcg tcctcgtggt ggaaggacaa gcacaacact caccacgccg    7440
cccccaacgt ccacggcgag gatcccgaca ttgacaccca ccctctgttg acctggagtg    7500
agcatgcgtt ggagatgttc tcggatgtcc cagatgagga gctgacccgc atgtggtcgc    7560
gtttcatggt cctgaaccag acctggtttt acttccccat tctctcgttt gcccgtctct    7620
cctggtgcct ccagtccatt ctctttgtgc tgcctaacgg tcaggccac aagccctcgg     7680 gcgcgcgtgt gcccatctcg ttggtcgagc agctgtcgct tgcgatgcac tggacctggt    7740
acctcgccac catgttcctg ttcatcaagg atcccgtcaa catgctggtg tacttttggg    7800
tgtcgcaggc ggtgtgcgga aacttgttgg ccatcgtgtt ctcgctcaac cacaacggta    7860
tgcctgtgat ctcgaggagg aggcggtcga tatggatttc ttcacgaagc agatcatcac    7920
gggtcgtgat gtccacccgg gtctatttgc caactggttc acgggtggat tgaactatca    7980
gatcgagcac cacttgttcc cttcgatgcc tcgccacaac ttttcaaaga tccagcctgc    8040
tgtcgagacc ctgtgcaaaa agtacaatgt ccgataccac accaccggta tgatcgaggg    8100
aactgcagag gtctttagcc gtctgaacga ggtctccaag gctacctcca agatgggtaa    8160
ggcgcagtaa gcggccgcca ccgcggcccg agattccggc ctcttcggcc gccaagcgac    8220
ccgggtggac gtctagaggt acctagcaat aacagatag tttgccggtg ataattctct     8280
taacctccca cactcctttg acataacgat ttatgtaacg aaactgaaat ttgaccagat    8340
attgtgtccg cggtggagct ccagcttttg ttccctttag tgagggttaa ttaattcgat    8400
atcataattg tcggccgagg tctgtacggc cagaaccgag atcctattga ggaggccaag    8460
cgataccaga aggctggctg ggaggcttac cagaagatta actgttagag gttagactat    8520
ggatatgtca tttaactgtg tatatagaga gcgtgcaagt atggagcgct tgttcagctt    8580
```

```
gtatgatggt cagacgacct gtctgatcga gtatgtatga tactgcacaa cctgtgtatc    8640
cgcatgatct gtccaatggg gcatgttgtt gtgtttctcg atacggagat gctgggtaca    8700
agtagctaat acgattgaac tacttatact tatatgaggc ttgaagaaag ctgacttgtg    8760
tatgacttat tctcaactac atccccagtc acaataccac cactgcacta ccactacacc    8820
aaaaccatga tcaaaccacc catggacttc ctggaggcag aagaacttgt tatggaaaag    8880
ctcaagagag agaa                                                      8894
```

```
<210> SEQ ID NO 97
<211> LENGTH: 31
<212> TYPE: DNA
<213> ORGANISM: Artificial Sequence
<220> FEATURE:
<223> OTHER INFORMATION: Primer YL101

<400> SEQUENCE: 97
gagcttggcg taatcgatgg tcatagctgt t                                   31

<210> SEQ ID NO 98
<211> LENGTH: 31
<212> TYPE: DNA
<213> ORGANISM: Artificial Sequence
<220> FEATURE:
<223> OTHER INFORMATION: Primer YL102

<400> SEQUENCE: 98
aacagctatg accatcgatt acgccaagct c                                   31

<210> SEQ ID NO 99
<211> LENGTH: 36
<212> TYPE: DNA
<213> ORGANISM: Artificial Sequence
<220> FEATURE:
<223> OTHER INFORMATION: Primer YL103

<400> SEQUENCE: 99
atgatgactc aggcgtttaa acgacggaat tcctgc                              36

<210> SEQ ID NO 100
<211> LENGTH: 36
<212> TYPE: DNA
<213> ORGANISM: Artificial Sequence
<220> FEATURE:
<223> OTHER INFORMATION: Primer YL104

<400> SEQUENCE: 100
gcaggaattc cgtcgtttaa acgcctgagt catcat                              36

<210> SEQ ID NO 101
<211> LENGTH: 10328
<212> TYPE: DNA
<213> ORGANISM: Artificial Sequence
<220> FEATURE:
<223> OTHER INFORMATION: 10328 bp fragment for integration and
      expression of the delta-6, delta-5, and delta-17 desaturase genes
      and the elongase gene

<400> SEQUENCE: 101
tatcacatca cgctctcatc aagaatactt cttgagaacc gtggagaccg ggttcgatt     60 ccccgtatcg gagtgtttat tttttgctca accataccct ggggtgtgtt ctgtggagca   120
ttctcacttt tggtaaacga cattgcttca agtgcagcgg aatcaaaaag tataaagtgg   180
gcagcgagta tacctgtaca gactgtaggc gataactcaa tccaattacc ccccacaaca   240
```

```
tgactggcca aactgatctc aagactttat tgaaatcagc aacaccgatt ctcaatgaag      300
gcacatactt cttctgcaac attcacttga cgcctaaagt tggtgagaaa tggaccgaca      360
agacatattc tgctatccac ggactgttgc ctgtgtcggt ggctacaata cgtgagtcag      420
aagggctgac ggtggtggtt cgtacgttgt gtggaattgt gagcggataa caatttcaca      480
caggaaacag ctatgaccat gattacgcca agctcgaaat taaccctcac taaagggaac      540
aaaagctgga gctccaccgc ggacacaata tctggtcaaa tttcagtttc gttacataaa      600
tcgttatgtc aaaggagtgt gggaggttaa gagaattatc accggcaaac tatctgttaa      660
ttgctaggta cctctagacg tccacccggg tcgcttggcg gccgaagagg ccggaatctc      720
gggccgcggt ggcggccgct tactgcaact tccttgcctt ctccttggca gcgtcggcct      780
tggcctgctt ggccaacttg gcgttctttc tgtaaaagtt gtagaagaga ccgagcatgg      840
tccacatgta gaaccaaagc agagccgtga tgaagaaggg gtatccgggg cggccaagga      900
ccttcatggc gtacatgtcc caggaagact ggaccgacat catgcagaac tgtgtcatct      960
gcgagcgcgt gatgtagaac ttgatgaacg acacctgctt gaagcccaag gccgacaaga     1020
agtagtagcc gtacatgatc acatggatga acgagttcaa cgcagcagag aagtaggctt     1080
caccgttggg tgcaacaaag gtgaccaacc accagatggt gaagatggag ctgtggtggt     1140
aaacgtgcaa gaaggagatc tggcggttgt tcttcttgag gaccatgatc atggtgtcga     1200
caaactccat gatcttggag aagtagaaga gccagatcat cttggccata ggaagaccct     1260
tgaaggtatg atcagcagcg ttctcaaaca gtccatagtt ggcctgataa gcctcgtaca     1320
ggatcccacc gcacatgtag gcgctgatcg agaccagaca aaagttgtgc aggagcgaaa     1380
acgtcttgac ctcgaaccgc tcaaagttct tcatgatctg catgcccaca agaccgtga      1440
ccaaataagc gagcacgatc aacagcacgt ggaacgggtt catcaacggc agctcacggg     1500
ccaaaggcga ctccaccgcg accaggaacc cacgcgtgtg atggacaatc gtggggatgt     1560
acttctcggc ctgggccacc agcgcggcct cgagaggatc gacatagggc gcggcccgga     1620
caccgatagc ggtggcaagg tccataaaca gatcttgcgg catctttgat gggaggaatg     1680
gcgcaatcga ctccatgcgg ccgctctaga actagtggat cctttgaatg attcttatac     1740
tcagaaggaa atgcttaacg atttcgggtg tgagttgaca aggagagaga gaaaagaaga     1800
ggaaaggtaa ttcggggacg gtggtctttt atacccttgg ctaaagtccc aaccacaaag     1860
caaaaaaatt ttcagtagtc tattttgcgt ccggcatggg ttacccggat ggccagacaa     1920
agaaactagt acaaagtctg aacaagcgta gattccagac tgcagtaccc tacgccctta     1980
acggcaagtg tgggaaccgg gggaggtttg atatgtgggg tgaaggggc tctcgccggg      2040
gttgggcccg ctactgggtc aatttggggt caattggggc aattgggct gttttttggg      2100
acacaaatac gccgccaacc cggtctctcc tgaagcttgt gagcggataa caatttcaca     2160
caggaaacag ctatgaccat gattacgcca agctcgaaat taaccctcac taaagggaac     2220
aaaagctgga gctccaccgc ggacacaata tctggtcaaa tttcagtttc gttacataaa     2280
tcgttatgtc aaaggagtgt gggaggttaa gagaattatc accggcaaac tatctgttaa     2340
ttgctaggta cctctagacg tccacccggg tcgcttggcg gccgaagagg ccggaatctc     2400
gggccgcggt ggcggccgcc tactcttcct tgggacggag tccaagaaca cgcaagtgct     2460
ccaaatgtga agcaaatgct tgccaaaacg tatccttgac aaggtatgga accttgtact     2520
cgctgcaggt gttcttgatg atggccagaa tatcgggata atggtgctgc gacacgttgg     2580
```

```
ggaacagatg gtgcacagcc tggtagttca agctgccagt gatgctggtc cagaggtgcg    2640
aatcgtgtgc gtaatcctgc gtagtctcga cctgcatagc tgcccagtcc ttttggatga    2700
tcccgttctc gtcaggcaac ggccactgaa cttcctcaac aacgtggttc gcctggaagg    2760
tcagcgccag ccagtaagac gacaccatgt ccgcgaccgt gaacaagagc agcaccttgc    2820 ccagggcag  atactgcagg ggaacaatca ggcgatacca gacaaagaaa gccttgccgc    2880
cccagaacat cacagtgtgc catgtcgaga tgggattgac acgaatagcg tcattggtct    2940
tgacaaagta caaaatgttg atgtcctgaa tgcgcacctt gaacgccagc agtccgtaca    3000
ggaaaggaac aaacatgtgc tggttgatgt ggttgacaaa ccacttttgg ttgggcttga    3060
tacgacgaac atcgggctca gacgtcgaca cgtcgggatc tgctccagca atgttggtgt    3120
aggggtgatg gccgagcata tgttggtaca tccacaccag gtacgatgct ccgttgaaaa    3180
agtcgtgcgt ggctcccaga atcttccaga cagtggggtt gtgggtcact gaaaagtgag    3240
acgcatcatg aagagggttg agtccgactt gtgcgcacgc aaatcccatg atgattgcaa    3300
acaccacctg aagccatgtg cgttcgacaa cgaaaggcac aaagagctgc gcgtagtagg    3360
aagcgatcaa ggatccaaag ataagagcgt atcgtcccca gatctctggt ctattcttgg    3420
gatcaatgtt ccgatccgta aagtagccct cgactctcgt cttgatggtt ttgtggaaca    3480
ccgttggctc cgggaagatg ggcagctcat tcgagaccag tgtaccgaca tagtacttct    3540
tcataatggc atctgcagcc ccaaacgcgt gatacatctc aaagaccgga gtaacatctc    3600
ggccagctcc gagcaggaga gtgtccactc caccaggatg gcggctcaag aactttgtga    3660
catcgtacac cctgccgcgg atggccaaga gtaggtcgtc cttggtgtta tgggccgcca    3720
gctcttccca ggtgaaggtt tttccttggt ccgttcccat ggtgaatgat tcttatactc    3780
agaaggaaat gcttaacgat ttcgggtgtg agttgacaag gagagagaga aaagaagagg    3840
aaaggtaatt cggggacggt ggtctttat  acccttggct aaagtcccaa ccacaaagca    3900
aaaaaatttt cagtagtcta ttttgcgtcc ggcatgggtt acccggatgg ccagacaaag    3960
aaactagtac aaagtctgaa caagcgtaga ttccagactg cagtacccta cgcccttaac    4020
ggcaagtgtg ggaaccgggg gaggtttgat atgtggggtg aaggggggctc tcgccggggt    4080 tgggcccgct actgggtcaa tttggggtca attggggcaa ttgggggctgt ttttttgggac    4140 acaaatacgc cgccaacccg gtctctcctg aattctgcag atgggctgca ggaattccgt    4200
cgtcgcctga gtcgacatca tttatttacc agttggccac aaacccttga cgatctcgta    4260
tgtcccctcc gacatactcc cggccggctg gggtacgttc gatagcgcta tcggcatcga    4320
caaggtttgg gtccctagcc gataccgcac tacctgagtc acaatcttcg gaggtttagt    4380
cttccacata gcacgggcaa aagtgcgtat atatacaaga gcgtttgcca gccacagatt    4440
ttcactccac acaccacatc acacatacaa ccacacacat ccacaatgga acccgaaact    4500
aagaagacca agactgactc caagaagatt gttcttctcg gcggcgactt ctgtggcccc    4560
gaggtgattg ccgaggccgt caaggtgctc aagtctgttg ctgaggcctc cggcaccgag    4620
tttgtgtttg aggaccgact cattggagga gctgccattg agaaggaggg cgagcccatc    4680
accgacgcta ctctcgacat ctgccgaaag gctgactcta ttatgctcgg tgctgtcgga    4740
ggcgctgcca acaccgtatg gaccactccc gacggacgaa ccgacgtgcg acccgagcag    4800
ggtctcctca agctgcgaaa ggacctgaac ctgtacgcca acctgcgacc ctgccagctg    4860
ctgtcgccca agctcgccga tctctccccc atccgaaacg ttgagggcac cgacttcatc    4920
attgtccgag agctcgtcgg aggtatctac tttggagagc gaaaggagga tgacggatct    4980
```

```
ggcgtcgctt ccgacaccga gacctactcc gttcctgagg ttgagcgaat tgcccgaatg   5040
gccgccttcc tggcccttca gcacaacccc cctcttcccg tgtggtctct tgacaaggcc   5100
aacgtgctgg cctcctctcg actttggcga aagactgtca ctcgagtcct caaggacgaa   5160
ttcccccagc tcgagctcaa ccaccagctg atcgactcgg ccgccatgat cctcatcaag   5220
cagccctcca agatgaatgg tatcatcatc accaccaaca tgtttggcga tatcatctcc   5280
gacgaggcct ccgtcatccc cggttctctg ggtctgctgc cctccgcctc tctggcttct   5340
ctgcccgaca ccaacgaggc gttcggtctg tacgagccct gtcacggatc tgcccccgat   5400
ctcggcaagc agaaggtcaa ccccattgcc accattctgt ctgccgccat gatgctcaag   5460
ttctctctta acatgaagcc cgccggtgac gctgttgagg ctgccgtcaa ggagtccgtc   5520
gaggctggta tcactaccgc cgatatcgga ggctcttcct ccacctccga ggtcggagac   5580
ttgttgccaa caaggtcaag gagctgctca agaaggagta agtcgtttct acgacgcatt   5640
gatggaagga gcaaactgac gcgcctgcgg gttggtctac cggcagggtc cgctagtgta   5700
taagactcta taaaagggc cctgccctgc taatgaaatg atgatttata atttaccggt   5760
gtagcaacct tgactagaag aagcagattg ggtgtgtttg tagtggagga cagtggtacg   5820
ttttggaaac agtcttcttg aaagtgtctt gtctacagta tattcactca taacctcaat   5880
agccaagggt gtagtcggtt tattaaagga agggagttgt ggctgatgtg gatagatatc   5940
tttaagctgg cgactgcacc caacgagtgt ggtggtagct tgttactgta tattcggtaa   6000
gatatatttt gtggggtttt agtggtgttt aaacgacgga attcctgcag cccatctgca   6060
gaattcagga gagaccgggt tggcggcgta tttgtgtccc aaaaaacagc cccaattgcc   6120
ccaattgacc ccaaattgac ccagtagcgg gcccaacccc ggcgagagcc cccttcaccc   6180
cacatatcaa acctccccg gttcccacac ttgccgttaa gggcgtaggg tactgcagtc   6240
tggaatctac gcttgttcag actttgtact agtttctttg tctggccatc cgggtaaccc   6300
atgccggacg caaaatagac tactgaaaat ttttttgctt tgtggttggg actttagcca   6360
agggtataaa agaccaccgt ccccgaatta ccttttcctct tcttttctct ctctccttgt   6420
caactcacac ccgaaatcgt taagcatttc cttctgagta taagaatcat tcaccatggc   6480
tgaggataag accaaggtcg agttccctac cctgactgag ctgaagcact ctatccctaa   6540
cgcttgcttt gagtccaacc tcggactctc gctctactac actgcccgag cgatcttcaa   6600
cgcatctgcc tctgctgctc tgctctacgc tgcccgatct actcccttca ttgccgataa   6660
cgttctgctc cacgctctgg tttgcgccac ctacatctac gtgcagggtg tcatcttctg   6720
gggtttcttt accgtcggtc acgactgtgg tcactctgcc ttctcccgat accactccgt   6780
caacttcatc attggctgca tcatgcactc tgccattctg actcccttcg agtcctggcg   6840
agtgacccac cgacaccatc acaagaacac tggcaacatt gataaggacg agatcttcta   6900
ccctcatcgg tccgtcaagg acctccagga cgtgcgacaa tgggtctaca ccctcggagg   6960
tgcttggttt gtctacctga aggtcggata tgctcctcga accatgtccc actttgaccc   7020
ctgggaccct ctcctgcttc gacgagcctc cgctgtcatc gtgtccctcg gagtctgggc   7080
tgccttcttc gctgcctacg cctacctcac atactcgctc ggctttgccg tcatgggcct   7140
ctactactat gctcctctct ttgtcttttg cttcgttcct cgtcattacta ccttcttgca   7200 tcacaacgac gaagctactc cctggtacgg tgactcggag tggacctacg tcaagggcaa   7260
cctgagctcc gtcgaccgat cgtacggagc tttcgtggac aacctgtctc accacattgg   7320
```

```
cacccaccag gtccatcact tgttccctat cattccccac tacaagctca acgaagccac    7380
caagcacttt gctgccgctt accctcacct cgtgagacgt aacgacgagc ccatcattac    7440
tgccttcttc aagaccgctc acctctttgt caactacgga gctgtgcccg agactgctca    7500
gattttcacc ctcaaagagt ctgccgctgc agccaaggcc aagagcgacc accaccatca    7560
ccaccattaa gcggccgcca ccgcggcccg agattccggc ctcttcggcc gccaagcgac    7620
ccgggtggac gtctagaggt acctagcaat taacagatag tttgccggtg ataattctct    7680
taacctccca cactcctttg acataacgat ttatgtaacg aaactgaaat ttgaccagat    7740
attgtgtccg cggtggagct ccagcttttg ttcccttag tgagggttaa tttcgagctt     7800
ggcgtaatcg atgcagaatt caggagagac cgggttggcg gcgtatttgt gtcccaaaaa    7860
acagccccaa ttgccccaat tgaccccaaa ttgacccagt agcgggccca accccggcga    7920
gagccccctt caccccacat atcaaacctc ccccggttcc cacacttgcc gttaagggcg    7980
tagggtactg cagtctggaa tctacgcttg ttcagacttt gtactagttt ctttgtctgg    8040
ccatccgggt aacccatgcc ggacgcaaaa tagactactg aaaattttt tgctttgtgg     8100
ttgggacttt agccaagggt ataaaagacc accgtccccg aattacctt cctcttcttt      8160
tctctctctc cttgtcaact cacacccgaa atcgttaagc atttccttct gagtataaga    8220
atcattcacc atggctgctg ctcccagtgt gaggacgttt actcgggccg aggttttgaa    8280
tgccgaggct ctgaatgagg gcaagaagga tgccgaggca cccttcttga tgatcatcga    8340
caacaaggtg tacgatgtcc gcgagttcgt ccctgatcat cccggtggaa gtgtgattct    8400
cacgcacgtt ggcaaggacg gcactgacgt ctttgacact tttcacccg aggctgcttg     8460
ggagactctt gccaactttt acgttggtga tattgacgag agcgaccgcg atatcaagaa    8520
tgatgacttt gcggccgagg tccgcaagct gcgtaccttg ttccagtctc ttggttacta    8580
cgattcttcc aaggcatact acgccttcaa ggtctcgttc aacctctgca tctggggttt    8640
gtcgacggtc attgtggcca agtggggcca gacctcgacc ctcgccaacg tgctctcggc    8700
tgcgcttttg ggtctgttct ggcagcagtg cggatggttg gctcacgact ttttgcatca    8760
ccaggtcttc caggaccgtt tctgggtga tcttttcggc gccttcttgg gaggtgtctg      8820
ccagggcttc tcgtcctcgt ggtggaagga caagcacaac actcaccacg ccgcccccaa    8880
cgtccacggc gaggatcccg acattgacac ccaccctctg ttgacctgga gtgagcatgc    8940
gttggagatg ttctcggatg tcccagatga ggagctgacc cgcatgtggt cgcgtttcat    9000
ggtcctgaac cagacctggt tttacttccc cattctctcg tttgcccgtc tctcctggtg    9060
cctccagtcc attctctttg tgctgcctaa cggtcaggcc cacaagccct cgggcgcgcg    9120
tgtgcccatc tcgttggtcg agcagctgtc gcttgcgatg cactggacct ggtacctcgc    9180
caccatgttc ctgttcatca aggatcccgt caacatgctg gtgtacttt tggtgtcgca      9240
ggcggtgtgc ggaaacttgt tggccatcgt gttctcgctc aaccacaacg gtatgcctgt    9300
gatctcgaag gaggaggcgg tcgatatgga tttcttcacg aagcagatca tcacgggtcg    9360
tgatgtccac ccgggtctat ttgccaactg gttcacgggt ggattgaact atcagatcga    9420
gcaccacttg ttccccttcga tgcctcgcca caacttttca aagatccagc ctgctgtcga    9480
gaccctgtgc aaaaagtaca atgtccgata ccacaccacc ggtatgatcg agggaactgc    9540
agaggtcttt agccgtctga acgaggtctc caaggctacc tccaagatgg gtaaggcgca    9600
gtaagcggcc gccaccgcgg cccgagattc cggcctcttc ggccgccaag cgacccgggt    9660
ggacgtctag aggtacctag caattaacag atagtttgcc ggtgataatt ctcttaacct    9720
```

```
cccacactcc tttgacataa cgatttatgt aacgaaactg aaatttgacc agatattgtg    9780
tccgcggtgg agctccagct tttgttccct ttagtgaggg ttaattaatt cgatatcata    9840
attgtcggcc gaggtctgta cggccagaac cgagatccta ttgaggaggc caagcgatac    9900
cagaaggctg gctgggaggc ttaccagaag attaactgtt agaggttaga ctatggatat    9960
gtcatttaac tgtgtatata gagagcgtgc aagtatggag cgcttgttca gcttgtatga   10020
tggtcagacg acctgtctga tcgagtatgt atgatactgc acaacctgtg tatccgcatg   10080
atctgtccaa tggggcatgt tgttgtgttt ctcgatacgg agatgctggg tacaagtagc   10140
taatacgatt gaactactta tacttatatg aggcttgaag aaagctgact tgtgtatgac   10200
ttattctcaa ctacatcccc agtcacaata ccaccactgc actaccacta caccaaaacc   10260
atgatcaaac cacccatgga cttcctggag gcagaagaac ttgttatgga aaagctcaag   10320
agagagaa                                                            10328
```

<210> SEQ ID NO 102
<211> LENGTH: 30
<212> TYPE: DNA
<213> ORGANISM: Artificial Sequence
<220> FEATURE:
<223> OTHER INFORMATION: Primer YL1

<400> SEQUENCE: 102
cagtgccaaa agccaaggca ctgagctcgt                                       30

<210> SEQ ID NO 103
<211> LENGTH: 31
<212> TYPE: DNA
<213> ORGANISM: Artificial Sequence
<220> FEATURE:
<223> OTHER INFORMATION: Primer YL2

<400> SEQUENCE: 103
gacgagctca gtgccttggc ttttggcact g                                     31

<210> SEQ ID NO 104
<211> LENGTH: 36
<212> TYPE: DNA
<213> ORGANISM: Artificial Sequence
<220> FEATURE:
<223> OTHER INFORMATION: Primer YL3

<400> SEQUENCE: 104
gtataagaat cattcaccat ggatccacta gttcta                                36

<210> SEQ ID NO 105
<211> LENGTH: 36
<212> TYPE: DNA
<213> ORGANISM: Artificial Sequence
<220> FEATURE:
<223> OTHER INFORMATION: Primer YL4

<400> SEQUENCE: 105
tagaactagt ggatccatgg tgaatgattc ttatac                                36

<210> SEQ ID NO 106
<211> LENGTH: 39
<212> TYPE: DNA
<213> ORGANISM: Artificial Sequence
<220> FEATURE:
<223> OTHER INFORMATION: Primer YL5

<400> SEQUENCE: 106 ccccctcga ggtcgatggt gtcgataagc ttgatatcg                                39

<210> SEQ ID NO 107
<211> LENGTH: 39
<212> TYPE: DNA
<213> ORGANISM: Artificial Sequence
<220> FEATURE:
<223> OTHER INFORMATION: Primer YL6

<400> SEQUENCE: 107
cgatatcaag cttatcgaca ccatcgacct cgaggggggg                              39

<210> SEQ ID NO 108
<211> LENGTH: 37
<212> TYPE: DNA
<213> ORGANISM: Artificial Sequence
<220> FEATURE:
<223> OTHER INFORMATION: Primer YL7

<400> SEQUENCE: 108
caaccgattt cgacagttaa ttaataattt gaatcga                                 37

<210> SEQ ID NO 109
<211> LENGTH: 37
<212> TYPE: DNA
<213> ORGANISM: Artificial Sequence
<220> FEATURE:
<223> OTHER INFORMATION: Primer YL8

<400> SEQUENCE: 109
tcgattcaaa ttattaatta actgtcgaaa tcggttg                                 37

<210> SEQ ID NO 110
<211> LENGTH: 35
<212> TYPE: DNA
<213> ORGANISM: Artificial Sequence
<220> FEATURE:
<223> OTHER INFORMATION: Primer YL9

<400> SEQUENCE: 110
tggtaaataa atgatgtcga ctcaggcgac gacgg                                   35

<210> SEQ ID NO 111
<211> LENGTH: 35
<212> TYPE: DNA
<213> ORGANISM: Artificial Sequence
<220> FEATURE:
<223> OTHER INFORMATION: Primer YL10

<400> SEQUENCE: 111
ccgtcgtcgc ctgagtcgac atcatttatt tacca                                   35

<210> SEQ ID NO 112
<211> LENGTH: 36
<212> TYPE: DNA
<213> ORGANISM: Artificial Sequence
<220> FEATURE:
<223> OTHER INFORMATION: Primer YL23

<400> SEQUENCE: 112
atggatccac tagttaatta actagagcgg ccgcca                                  36

<210> SEQ ID NO 113
<211> LENGTH: 36

<212> TYPE: DNA
<213> ORGANISM: Artificial Sequence
<220> FEATURE:
<223> OTHER INFORMATION: Primer YL24

<400> SEQUENCE: 113
tggcggccgc tctagttaat taactagtgg atccat     36

<210> SEQ ID NO 114
<211> LENGTH: 1413
<212> TYPE: DNA
<213> ORGANISM: Saprolegnia diclina (ATCC #56851)

<400> SEQUENCE: 114
atggccccgc agacggagct ccgccagcgc cacgccgccg tcgccgagac gccggtggcc     60
ggcaagaagg cctttacatg gcaggaggtc gcgcagcaca cacggcggc ctcggcctgg    120
atcattatcc gcggcaaggt ctacgacgtg accgagtggg ccaacaagca ccccggcggc    180
cgcgagatgg tgctgctgca cgccggtcgc gaggccaccg acacgttcga ctcgtaccac    240
ccgttcagcg acaaggccga gtcgatcttg aacaagtatg agattggcac gttcacgggc    300
ccgtccgagt ttccgacctt caagccggac acgggcttct acaaggagtg ccgcaagcgc    360
gttggcgagt acttcaagaa gaacaacctc catccgcagg acggcttccc gggcctctgg    420
cgcatgatgg tcgtgtttgc ggtcgccggc ctcgccttgt acggcatgca cttttcgact    480
atctttgcgc tgcagctcgc ggccgcgcg ctctttggcg tctgccaggc gctgccgctg    540
ctccacgtca tgcacgactc gtcgcacgcg tcgtacacca acatgccgtt cttccattac    600
gtcgtcggcc gctttgccat ggactggttt gccggcggct cgatggtgtc atggctcaac    660
cagcacgtcg tgggccacca catctacacg aacgtcgcgg gctcggaccc ggatcttccg    720
gtcaacatgg acggcgacat ccgccgcatc gtgaaccgcc aggtgttcca gcccatgtac    780
gcattccagc acatctacct tccgccgctc tatggcgtgc ttggcctcaa gttccgcatc    840
caggacttca ccgacacgtt cggctcgcac acgaacggcc cgatccgcgt caacccgcac    900
gcgctctcga cgtggatggc catgatcagc tccaagtcgt tctgggcctt ctaccgcgtg    960
taccttccgc ttgccgtgct ccagatgccc atcaagacgt accttgcgat cttcttcctc   1020
gccgagtttg tcacgggctg gtacctcgcg ttcaacttcc aagtaagcca tgtctcgacc   1080
gagtgcggct acccatgcgg cgacgaggcc aagatggcgc tccaggacga gtgggcagtc   1140
tcgcaggtca gacgtcggt cgactacgcc catggctcgt ggatgacgac gttccttgcc   1200
ggcgcgctca actaccaggt cgtgcaccac ttgttcccca gcgtgtcgca gtaccactac   1260
ccggcgatcg cgcccatcat cgtcgacgtc tgcaaggagt acaacatcaa gtacgccatc   1320
ttgccggact ttacggcggc gttcgttgcc cacttgaagc acctccgcaa catgggccag   1380
cagggcatcg ccgccacgat ccacatgggc taa                              1413

<210> SEQ ID NO 115
<211> LENGTH: 470
<212> TYPE: PRT
<213> ORGANISM: Saprolegnia diclina (ATCC #56851)

<400> SEQUENCE: 115

Met Ala Pro Gln Thr Glu Leu Arg Gln Arg His Ala Ala Val Ala Glu
1               5                   10                  15

Thr Pro Val Ala Gly Lys Lys Ala Phe Thr Trp Gln Glu Val Ala Gln
            20                  25                  30

-continued

```
His Asn Thr Ala Ala Ser Ala Trp Ile Ile Arg Gly Lys Val Tyr
         35                  40                  45
Asp Val Thr Glu Trp Ala Asn Lys His Pro Gly Gly Arg Glu Met Val
 50                  55                  60
Leu Leu His Ala Gly Arg Glu Ala Thr Asp Thr Phe Asp Ser Tyr His
 65                  70                  75                  80
Pro Phe Ser Asp Lys Ala Glu Ser Ile Leu Asn Lys Tyr Glu Ile Gly
                 85                  90                  95
Thr Phe Thr Gly Pro Ser Glu Phe Pro Thr Phe Lys Pro Asp Thr Gly
            100                 105                 110
Phe Tyr Lys Glu Cys Arg Lys Arg Val Gly Glu Tyr Phe Lys Lys Asn
            115                 120                 125
Asn Leu His Pro Gln Asp Gly Phe Pro Gly Leu Trp Arg Met Met Val
        130                 135                 140
Val Phe Ala Val Ala Gly Leu Ala Leu Tyr Gly Met His Phe Ser Thr
145                 150                 155                 160
Ile Phe Ala Leu Gln Leu Ala Ala Ala Leu Phe Gly Val Cys Gln
                165                 170                 175
Ala Leu Pro Leu Leu His Val Met His Asp Ser Ser His Ala Ser Tyr
            180                 185                 190
Thr Asn Met Pro Phe Phe His Tyr Val Val Gly Arg Phe Ala Met Asp
        195                 200                 205
Trp Phe Ala Gly Gly Ser Met Val Ser Trp Leu Asn Gln His Val Val
    210                 215                 220
Gly His His Ile Tyr Thr Asn Val Ala Gly Ser Asp Pro Asp Leu Pro
225                 230                 235                 240
Val Asn Met Asp Gly Asp Ile Arg Arg Ile Val Asn Arg Gln Val Phe
                245                 250                 255
Gln Pro Met Tyr Ala Phe Gln His Ile Tyr Leu Pro Pro Leu Tyr Gly
            260                 265                 270
Val Leu Gly Leu Lys Phe Arg Ile Gln Asp Phe Thr Asp Thr Phe Gly
            275                 280                 285
Ser His Thr Asn Gly Pro Ile Arg Val Asn Pro His Ala Leu Ser Thr
        290                 295                 300
Trp Met Ala Met Ile Ser Ser Lys Ser Phe Trp Ala Phe Tyr Arg Val
305                 310                 315                 320
Tyr Leu Pro Leu Ala Val Leu Gln Met Pro Ile Lys Thr Tyr Leu Ala
                325                 330                 335
Ile Phe Phe Leu Ala Glu Phe Val Thr Gly Trp Tyr Leu Ala Phe Asn
            340                 345                 350
Phe Gln Val Ser His Val Ser Thr Glu Cys Gly Tyr Pro Cys Gly Asp
            355                 360                 365
Glu Ala Lys Met Ala Leu Gln Asp Glu Trp Ala Val Ser Gln Val Lys
        370                 375                 380
Thr Ser Val Asp Tyr Ala His Gly Ser Trp Met Thr Thr Phe Leu Ala
385                 390                 395                 400
Gly Ala Leu Asn Tyr Gln Val Val His His Leu Phe Pro Ser Val Ser
                405                 410                 415
Gln Tyr His Tyr Pro Ala Ile Ala Pro Ile Ile Val Asp Val Cys Lys
            420                 425                 430
Glu Tyr Asn Ile Lys Tyr Ala Ile Leu Pro Asp Phe Thr Ala Ala Phe
        435                 440                 445
Val Ala His Leu Lys His Leu Arg Asn Met Gly Gln Gln Gly Ile Ala
```

```
                450            455            460
Ala Thr Ile His Met Gly
465                 470

<210> SEQ ID NO 116
<211> LENGTH: 30
<212> TYPE: DNA
<213> ORGANISM: Artificial Sequence
<220> FEATURE:
<223> OTHER INFORMATION: Primer YL13A

<400> SEQUENCE: 116
ttggatccgc agacggagct ccgccagcgc                                        30

<210> SEQ ID NO 117
<211> LENGTH: 36
<212> TYPE: DNA
<213> ORGANISM: Artificial Sequence
<220> FEATURE:
<223> OTHER INFORMATION: Primer YL14

<400> SEQUENCE: 117
cccttaatta aattagccca tgtggatcgt ggcggc                                 36

<210> SEQ ID NO 118
<211> LENGTH: 1329
<212> TYPE: DNA
<213> ORGANISM: Isochrysis galbana CCMP1323

<400> SEQUENCE: 118
atggtggcag gcaaatcagg cgctgcggcg cacgtgactc acagctcgac attgccccgt        60
gagtaccatg gcgcgaccaa cgactcgcgc tctgaggcgg ccgacgtcac cgtctctagc       120
atcgatgctg aaaaggagat gatcatcaac ggccgcgtgt atgacgtgtc gtcatttgtg       180
aagcggcacc caggtggctc ggtgatcaag ttccagctgg cgccgacgc gagcgacgcg        240 tacaacaact ttcacgtccg ctccaagaag gcggacaaga tgctgtattc gctcccgtcc       300
cggccggccg aggccggcta cgcccaggac gacatctccc gcgactttga gaagctgcgc      360
ctcgagctga aggaggaggg ctacttcgag cccaacctgg tgcacgtgag ctacaggtgt      420
gtggaggttc ttgccatgta ctgggctggc gtccagctca tctggtccgg gtactggttc      480
ctcggcgcga tcgtggccgg cattgcgcag ggccgctgcg gctggctcca gcatgagggt      540
gggcactact cgctcaccgg caacatcaag atcgaccggc atctgcagat ggccatctat      600
gggcttggct gcggcatgtc gggctgctac tggcgcaacc agcacaacaa gcaccacgcc      660
acgccgcaga agctcgggac cgaccccgac ctgcagacga tgccgctggt ggccttccac      720
aagatcgtcg cgccaaggc gcgaggcaag gcaaggcgt ggctggcgtg caggcgccg        780 ctcttctttg gcgggatcat ctgctcgctc gtctctttcg gctggcagtt cgtgctccac      840
cccaaccacg cgctgcgcgt gcacaatcac ctggagctcg cgtacatggg cctgcggtac      900
gtgctgtggc acctggcctt tggccacctc gggctgctga gctcgctccg cctgtacgcc      960
ttttacgtgg ccgtgggcgg cacctacatc ttcaccaact tcgccgtctc gcacacccac     1020
aaggacgtcg tcccgcccac caagcacatc tcgtgggcac tctactcggc caaccacacg     1080
accaactgct ccgactcgcc ctttgtcaac tggtggatgg cctacctcaa cttccagatc     1140
gagcaccacc tcttccccgtc gatgccgcag tacaaccacc ccaagatcgc cccgcgggtg     1200
cgcgcgctct tcgagaagca cgggtcgag tatgacgtcc ggccatacct ggagtgtttt     1260
```
cgggtcacgt acgtcaacct gctcgccgta ggcaacccgg agcactccta ccacgagcac    1320
acgcactag                                                           1329

<210> SEQ ID NO 119
<211> LENGTH: 442
<212> TYPE: PRT
<213> ORGANISM: Isochrysis galbana CCMP1323

<400> SEQUENCE: 119

Met Val Ala Gly Lys Ser Gly Ala Ala His Val Thr His Ser Ser
1               5                   10                  15

Thr Leu Pro Arg Glu Tyr His Gly Ala Thr Asn Asp Ser Arg Ser Glu
            20                  25                  30

Ala Ala Asp Val Thr Val Ser Ser Ile Asp Ala Glu Lys Glu Met Ile
        35                  40                  45

Ile Asn Gly Arg Val Tyr Asp Val Ser Ser Phe Val Lys Arg His Pro
    50                  55                  60

Gly Gly Ser Val Ile Lys Phe Gln Leu Gly Ala Asp Ala Ser Asp Ala
65                  70                  75                  80

Tyr Asn Asn Phe His Val Arg Ser Lys Lys Ala Asp Lys Met Leu Tyr
                85                  90                  95

Ser Leu Pro Ser Arg Pro Ala Glu Ala Gly Tyr Ala Gln Asp Asp Ile
            100                 105                 110

Ser Arg Asp Phe Glu Lys Leu Arg Leu Glu Leu Lys Glu Glu Gly Tyr
        115                 120                 125

Phe Glu Pro Asn Leu Val His Val Ser Tyr Arg Cys Val Glu Val Leu
130                 135                 140

Ala Met Tyr Trp Ala Gly Val Gln Leu Ile Trp Ser Gly Tyr Trp Phe
145                 150                 155                 160

Leu Gly Ala Ile Val Ala Gly Ile Ala Gln Gly Arg Cys Gly Trp Leu
                165                 170                 175

Gln His Glu Gly Gly His Tyr Ser Leu Thr Gly Asn Ile Lys Ile Asp
            180                 185                 190

Arg His Leu Gln Met Ala Ile Tyr Gly Leu Gly Cys Gly Met Ser Gly
        195                 200                 205

Cys Tyr Trp Arg Asn Gln His Asn Lys His His Ala Thr Pro Gln Lys
    210                 215                 220

Leu Gly Thr Asp Pro Asp Leu Gln Thr Met Pro Leu Val Ala Phe His
225                 230                 235                 240

Lys Ile Val Gly Ala Lys Ala Arg Gly Lys Gly Lys Ala Trp Leu Ala
                245                 250                 255

Trp Gln Ala Pro Leu Phe Phe Gly Gly Ile Ile Cys Ser Leu Val Ser
            260                 265                 270

Phe Gly Trp Gln Phe Val Leu His Pro Asn His Ala Leu Arg Val His
        275                 280                 285

Asn His Leu Glu Leu Ala Tyr Met Gly Leu Arg Tyr Val Leu Trp His
    290                 295                 300

Leu Ala Phe Gly His Leu Gly Leu Leu Ser Ser Leu Arg Leu Tyr Ala
305                 310                 315                 320

Phe Tyr Val Ala Val Gly Gly Thr Tyr Ile Phe Thr Asn Phe Ala Val
                325                 330                 335

Ser His Thr His Lys Asp Val Val Pro Pro Thr Lys His Ile Ser Trp
            340                 345                 350

Ala Leu Tyr Ser Ala Asn His Thr Thr Asn Cys Ser Asp Ser Pro Phe

|   |   |   |   | 355 |   |   |   |   | 360 |   |   |   |   | 365 |   |
|---|---|---|---|---|---|---|---|---|---|---|---|---|---|---|---|

Val Asn Trp Trp Met Ala Tyr Leu Asn Phe Gln Ile Glu His His Leu
370                 375                 380

Phe Pro Ser Met Pro Gln Tyr Asn His Pro Lys Ile Ala Pro Arg Val
385                 390                 395                 400

Arg Ala Leu Phe Glu Lys His Gly Val Glu Tyr Asp Val Arg Pro Tyr
                405                 410                 415

Leu Glu Cys Phe Arg Val Thr Tyr Val Asn Leu Leu Ala Val Gly Asn
            420                 425                 430

Pro Glu His Ser Tyr His Glu His Thr His
            435                 440

<210> SEQ ID NO 120
<211> LENGTH: 36
<212> TYPE: DNA
<213> ORGANISM: Artificial Sequence
<220> FEATURE:
<223> OTHER INFORMATION: Primer YL19A

<400> SEQUENCE: 120
tttggatccg gcaggcaaat caggcgctgc ggcgca                           36

<210> SEQ ID NO 121
<211> LENGTH: 36
<212> TYPE: DNA
<213> ORGANISM: Artificial Sequence
<220> FEATURE:
<223> OTHER INFORMATION: Primer YL20

<400> SEQUENCE: 121
ccttaattaa ctagtgcgtg tgctcgtggt aggagt                           36

<210> SEQ ID NO 122
<211> LENGTH: 1320
<212> TYPE: DNA
<213> ORGANISM: Thraustochytrium aureum (ATCC #34304)

<400> SEQUENCE: 122
atgggacgcg gcggcgaagg tcaggtgaac agcgcgcagg tggcacaagg cggtgcggga    60
acgcgaaaga cgatcctgat cgagggcgag gtctacgatg tcaccaactt taggcacccc   120
ggcgggtcga tcatcaagtt tctcacgacc gacggcaccg aggctgtgga cgcgacgaac   180
gcgtttcgcg agtttcactg ccggtcgggc aaggcggaaa agtacctcaa gagcctgccc   240
aagctcggcg cgccgagcaa gatgaagttt gacgccaagg agcaggcccg cgcgacgcg    300 atcacgcgag actacgtcaa gctgcgcgag gagatggtgg ccgagggcct cttcaagccc   360
gcgcccctcc acattgtcta caggtttgcg gagatcgcag ccctgttcgc ggcctcgttc   420
tacctgtttt cgatgcgcgg aaacgtgttc gccacgctcg cggccatcgc agtcggggc    480 atcgcgcagg gccgctgcgg ctggctcatg cacgagtgcg acacttctc gatgaccggg   540 tacatcccgc ttgacgtgcg cctgcaggag ctggtgtacg gcgtggggtg ctcgatgtcg   600
gcgagctggt ggcgcgttca gcacaacaag caccacgcga ccccgcagaa actcaagcac   660
gacgtcgacc tcgacaccct gccgctcgtt gcgttcaacg agaagatcgc cgccaaggtg   720
cgccccggct cgttccaggc caagtggctc tcggcgcagg cgtacatttt tgcgccggtg   780
tcctgcttcc tggttggtct cttctggacc ctgtttctgc acccgcgcca catgccgcgc   840
acgagccact ttgctgagat ggccgccgtc gcggtgcgcg tcgtgggctg gcggcgctc   900

```
atgcactcgt tcgggtacag cgggagcgac tcgttcggtc tctacatggc cacctttggc   960
tttggctgca cctacatctt caccaacttt gcggtcagcc acacgcacct cgacgtcacc   1020
gagccggacg agttcctgca ctgggtcgag tacgccgcgc tgcacacgac caacgtgtcc   1080
aacgactcgt ggttcatcac ctggtggatg tcgtacctca actttcagat cgagcaccac   1140
ctctttccgt cgctgcccca gctcaacgcc ccgcgcgtcg ccccgcgcgt ccgcgccctc   1200 tcgagaagc acggcatggc ttacgacgag cgcccgtacc ttaccgcgct ggcgacacg    1260 tttgccaacc tgcacgccgt gggccaaaac gcgggccagg cggcggccaa ggccgcttag  1320
```

<210> SEQ ID NO 123
<211> LENGTH: 439
<212> TYPE: PRT
<213> ORGANISM: Thraustochytrium aureum (ATCC #34304)

<400> SEQUENCE: 123

```
Met Gly Arg Gly Gly Glu Gly Gln Val Asn Ser Ala Gln Val Ala Gln
1               5                   10                  15

Gly Gly Ala Gly Thr Arg Lys Thr Ile Leu Ile Glu Gly Glu Val Tyr
            20                  25                  30

Asp Val Thr Asn Phe Arg His Pro Gly Gly Ser Ile Ile Lys Phe Leu
        35                  40                  45

Thr Thr Asp Gly Thr Glu Ala Val Asp Ala Thr Asn Ala Phe Arg Glu
    50                  55                  60

Phe His Cys Arg Ser Gly Lys Ala Glu Lys Tyr Leu Lys Ser Leu Pro
65                  70                  75                  80

Lys Leu Gly Ala Pro Ser Lys Met Lys Phe Asp Ala Lys Glu Gln Ala
                85                  90                  95

Arg Arg Asp Ala Ile Thr Arg Asp Tyr Val Lys Leu Arg Glu Glu Met
            100                 105                 110

Val Ala Glu Gly Leu Phe Lys Pro Ala Pro Leu His Ile Val Tyr Arg
        115                 120                 125

Phe Ala Glu Ile Ala Ala Leu Phe Ala Ala Ser Phe Tyr Leu Phe Ser
    130                 135                 140

Met Arg Gly Asn Val Phe Ala Thr Leu Ala Ala Ile Ala Val Gly Gly
145                 150                 155                 160

Ile Ala Gln Gly Arg Cys Gly Trp Leu Met His Glu Cys Gly His Phe
                165                 170                 175

Ser Met Thr Gly Tyr Ile Pro Leu Asp Val Arg Leu Gln Glu Leu Val
            180                 185                 190

Tyr Gly Val Gly Cys Ser Met Ser Ala Ser Trp Trp Arg Val Gln His
        195                 200                 205

Asn Lys His His Ala Thr Pro Gln Lys Leu Lys His Asp Val Asp Leu
    210                 215                 220

Asp Thr Leu Pro Leu Val Ala Phe Asn Glu Lys Ile Ala Ala Lys Val
225                 230                 235                 240

Arg Pro Gly Ser Phe Gln Ala Lys Trp Leu Ser Ala Gln Ala Tyr Ile
                245                 250                 255

Phe Ala Pro Val Ser Cys Phe Leu Val Gly Leu Phe Trp Thr Leu Phe
            260                 265                 270

Leu His Pro Arg His Met Pro Arg Thr Ser His Phe Ala Glu Met Ala
        275                 280                 285

Ala Val Ala Val Arg Val Val Gly Trp Ala Ala Leu Met His Ser Phe
    290                 295                 300
```

Gly Tyr Ser Gly Ser Asp Ser Phe Gly Leu Tyr Met Ala Thr Phe Gly
305                 310                 315                 320

Phe Gly Cys Thr Tyr Ile Phe Thr Asn Phe Ala Val Ser His Thr His
            325                 330                 335

Leu Asp Val Thr Glu Pro Asp Glu Phe Leu His Trp Val Glu Tyr Ala
            340                 345                 350

Ala Leu His Thr Thr Asn Val Ser Asn Asp Ser Trp Phe Ile Thr Trp
        355                 360                 365

Trp Met Ser Tyr Leu Asn Phe Gln Ile Glu His His Leu Phe Pro Ser
        370                 375                 380

Leu Pro Gln Leu Asn Ala Pro Arg Val Ala Pro Arg Val Arg Ala Leu
385                 390                 395                 400

Phe Glu Lys His Gly Met Ala Tyr Asp Glu Arg Pro Tyr Leu Thr Ala
            405                 410                 415

Leu Gly Asp Thr Phe Ala Asn Leu His Ala Val Gly Gln Asn Ala Gly
            420                 425                 430

Gln Ala Ala Ala Lys Ala Ala
            435

<210> SEQ ID NO 124
<211> LENGTH: 30
<212> TYPE: DNA
<213> ORGANISM: Artificial Sequence
<220> FEATURE:
<223> OTHER INFORMATION: Primer YL15

<400> SEQUENCE: 124
ttttccatgg gacgcggcgg cgaaggtcag                                30

<210> SEQ ID NO 125
<211> LENGTH: 37
<212> TYPE: DNA
<213> ORGANISM: Artificial Sequence
<220> FEATURE:
<223> OTHER INFORMATION: Primer YL16B

<400> SEQUENCE: 125
ttttgcggcc gctaagcggc cttggccgcc gcctggc                        37

<210> SEQ ID NO 126
<211> LENGTH: 10
<212> TYPE: DNA
<213> ORGANISM: Yarrowia lipolytica
<220> FEATURE:
<221> NAME/KEY: misc_feature
<222> LOCATION: (8)..(8)
<223> OTHER INFORMATION: n is a, c, g, or t

<400> SEQUENCE: 126 mammatgnhs                                                      10

What is claimed is:

1. A transformed oleaginous yeast that produces at least 25% of its dry cell weight as oil and that is capable of producing at least one omega-3 polyunsaturated fatty acid, wherein said yeast comprises:
(i) at least one heterologous gene encoding a delta-17 desaturase, and
(ii) at least one heterologous gene that encodes a desaturase or an elongase and that comprises a translation initiation site as set forth in SEQ ID NO:126.

2. The oleaginous yeast according to claim 1, wherein said yeast is selected from the group consisting of *Yarrowia, Candida, Rhodotorula, Rhodosporidium, Cryptococcus, Trichosporon* and *Lipomyces*.

3. The oleaginous yeast according to claim 2, wherein the yeast is *Yarrowia lipolytica*.

4. The oleaginous yeast according to claim 1, wherein the yeast further comprises at least one gene encoding an enzyme selected from the group consisting of delta-12 desaturase, delta-6 desaturase, delta-15 desaturase, delta-9 desaturase, delta-5 desaturase and delta-4 desaturase.

5. The oleaginous yeast according to claim 1, wherein the omega-3 polyunsaturated fatty acid is selected from the group consisting of: alpha-linolenic acid, stearidonic acid, eicosatetraenoic acid, eicosapentaenoic acid, docosapentaenoic acid and docosahexaenoic acid.

6. The oleaginous yeast according to claim 5, wherein the omega-3 polyunsaturated fatty acid is eicosapentaenoic acid.

7. The oleaginous yeast according to claim 1, wherein substrate for said delta-17 desaturase is endogenous to the yeast.

8. The oleaginous yeast according to claim 1, wherein the yeast further comprises heterologous genes encoding a delta-12 desaturase, an elongase, a delta-9 desaturase, and a delta-5 desaturase.

9. The oleaginous yeast according to claim 8, wherein the omega-3 polyunsaturated fatty acid is eicosapentaenoic acid.

10. The oleaginous yeast according to claim 1, wherein the yeast is at a temperature of about 28° C. to about 30° C.

11. The oleaginous yeast according to claim 1, wherein the yeast is at a temperature of about 30° C.

12. The oleaginous yeast according to claim 3, wherein the yeast is at a temperature of about 28° C. to about 30° C.

13. The oleaginous yeast according to claim 3, wherein the yeast is at a temperature of about 30° C.

* * * * *